(12) United States Patent
Jeo et al.

(10) Patent No.: US 10,745,446 B2
(45) Date of Patent: Aug. 18, 2020

(54) PEPTIDE NUCLEIC ACID COMPLEX HAVING IMPROVED CELL PERMEABILITY AND PHARMACEUTICAL COMPOSITION COMPRISING SAME

(71) Applicant: SEASUN THERAPEUTICS, Daejeon (KR)

(72) Inventors: Goonho Jeo, Daejeon (KR); Hye Joo Kim, Daejeon (KR); Ji-Yeon Yu, Chungcheongbuk-do (KR); Chinbayar Batochir, Daejeon (KR); Deokhwe Hur, Gangwon-do (KR); Hee Kyung Park, Daejeon (KR)

(73) Assignee: SEASUN THERAPEUTICS, Daejeon (KR)

( * ) Notice: Subject to any disclaimer, the term of this patent is extended or adjusted under 35 U.S.C. 154(b) by 0 days.

(21) Appl. No.: 16/322,965

(22) PCT Filed: Aug. 9, 2017

(86) PCT No.: PCT/KR2017/008636
§ 371 (c)(1),
(2) Date: Feb. 3, 2019

(87) PCT Pub. No.: WO2018/030789
PCT Pub. Date: Feb. 15, 2018

(65) Prior Publication Data
US 2019/0185519 A1    Jun. 20, 2019

(30) Foreign Application Priority Data
Aug. 9, 2016   (KR) .................. 10-2016-0101374

(51) Int. Cl.
| | |
|---|---|
| C07K 14/00 | (2006.01) |
| C12N 15/113 | (2010.01) |
| C12Q 1/68 | (2018.01) |
| A61K 31/7088 | (2006.01) |
| A61K 31/7125 | (2006.01) |
| A61K 31/713 | (2006.01) |
| A61K 47/54 | (2017.01) |
| A61P 17/06 | (2006.01) |
| A61K 9/06 | (2006.01) |

(52) U.S. Cl.
CPC ............ C07K 14/003 (2013.01); A61K 9/06 (2013.01); A61K 31/7088 (2013.01); A61K 47/54 (2017.08); A61P 17/06 (2018.01); C07K 14/00 (2013.01); C12N 15/113 (2013.01); C12Q 1/68 (2013.01); C12N 2310/11 (2013.01); C12N 2310/314 (2013.01); C12N 2310/315 (2013.01); C12N 2310/3125 (2013.01); C12N 2310/321 (2013.01); C12N 2310/322 (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 5,719,262 A | 2/1998 | Buchardt et al. | |
| 2005/0250148 A1 | 11/2005 | Bevilacqua et al. | |

FOREIGN PATENT DOCUMENTS

| | | |
|---|---|---|
| JP | 2000503671 A | 3/2000 |
| JP | 2008220366 A | 9/2008 |
| JP | 2011504110 A | 2/2011 |
| KR | 1020120079104 A | 7/2012 |
| KR | 1020150053945 A | 5/2014 |
| WO | WO9501369 A1 | 1/1995 |
| WO | WO9803542 A1 | 1/1998 |
| WO | WO2015112438 A1 | 7/2015 |

OTHER PUBLICATIONS

Haaima et al. Angew.-Chem. Int. Ed. Engl. 1996, vol. 35 pp. 1939-1942.*
Dragulescu-Andrasi et al. Chem. Connnnun. 2005, pp. 244-246.*
Manicardi et al. ChemBioChem 2012, vol. 13, pp. 1327-1337.*
Koppelhus, U., et al., "Cellular delivery of peptide nucleic acid (PNA)", "Advanced Drug Delivery Reviews", 2003, pp. 267-280, vol. 55, No. 2, Publisher: Elsevier.
Lim, J., "A Study on the Binding and Synthesis of Biosynthetic Skeleton Based on Beta- and Gamma-/Delta-Amino Acids", "KAIST", 2009, Publisher: chemistry and master's degree paper (Korean).
Lim, J., "A Study on the Binding and Synthesis of Biosynthetic Skeleton Based on Beta- and Gamma-/Delta-Amino Acids", "KAIST", 2009, Publisher: chemistry and master's degree paper (Eng Trans).
Mitra, R., et al., "Aminomethylene Peptide Nucleic Acid (am-PNA): Synthesis, Regio-/Stereospecific DNA Binding, and Differential Cell Uptake of (/,R/S)am-PNA Analogues", "The Journal of Organic Chemistry", 2012, pp. 5696-5704, vol. 77, No. 13, Publisher: American Chemical Society.
(Continued)

*Primary Examiner* — Tracy Vivlemore
(74) *Attorney, Agent, or Firm* — Hultquist, PLLC; Steven J. Hultquist

(57) ABSTRACT

The present invention relates to a nucleic acid complex having a novel structure, which can introduce a bioactive nucleic acid into cells, a composition for treating and diagnosing disease, which comprises the same, and a method of regulating expression of a target gene using the same, and more particularly to a nucleic acid complex comprising a bioactive nucleic acid complementarily bound to a carrier peptide nucleic acid modified to be generally positively charged, a composition for treating and diagnosing disease, which comprises the same, and a method of regulating expression of a target gene using the same.

19 Claims, 44 Drawing Sheets
(30 of 44 Drawing Sheet(s) Filed in Color)
Specification includes a Sequence Listing.

(56) References Cited

OTHER PUBLICATIONS

Buyens, K., et al., "Liposome based systems for systemic siRNA delivery: Stability in blood sets the requirements or optimal carrier design", "Journal of Controlled Release", 2012, pp. 362-370, vol. 158, Publisher: Elsevier.

Couto, L., et al., "Viral vector-mediated RNA interference", "Current Opinion in Pharmacology", 2010, pp. 534-542, vol. 10, Publisher: www.sciencedirect.com; Elsevier.

Joergensen, M., et al., "Efficiency of Cellular Delivery of Antisense Peptide Nucleic Acid by Electroporation Depends on Charge and Electroporation Geometry", "Oligonucleotides", 2011, p. 2011 vol. 21, No. 1, Publisher: Mary Ann Liebert, Inc.; DOI: 10.1089/oli.2010.0266.

Kole, R., et al., "RNA therapeutics: Beyond RNA interference and antisense oligonucleotides", "Nat Rev Drug Discov", Feb. 5, 2016, pp. 125-140, vol. 11, No. 2, Publisher: HHS Public Access.

Morris, KV, et al., "Lentiviral-mediated delivery of siRNAs for antiviral therapy", "Gene Therapy", 2006, pp. 553-558, vol. 13, Publisher: 2006Nature Publishing Group.

Szoka, F., "Comparative Properties and Methods of Preparation of Lipid Vesicles (Liposomes)1", "Ann. Rev. Biophys. Bioeng.", 1980, pp. 467-508, vol. 9, Publisher: Annual Reviews Inc.

Trabulo, S., et al., "Cell-penetrating Peptides as Nucleic Acid Delivery Systems: From Biophysics to Biological Applications", "Current Pharmaceutical Design", 2013, pp. 1-29, vol. 19, No. 00, Publisher: ResearchGate; Bentham Science Publishers.

Wilson, C., et al., "Building oligonucleotide therapeutics using non-natural chemistries", "Current Opinion in Chemical Biology", 2006, pp. 607-614, vol. 10, Publisher: www.sciencedirect.com; Elsevier.

Yousefi, A., et al., "Trends in polymeric delivery of nucleic acids to tumors", "Journal of Controlled Release", 2013 pp. 209-218, vol. 170, Publisher: SciVerse ScienceDirect; Elsevier.

Shiraishi, T., et al., "Peptide Nucleic Acid (PNA) Cell Penetrating Peptide (CPP) Conjugates as Carriers for cellular Delivery of Antisense Oligomers", "Artificial DNA: PNA and XNA", 2011, pp. 90-99, vol. 2, No. 3.

Sugiyama, T., et al., "Chiral Peptide Nucleic Acids with a Substituent in the N-(2-Aminoethy)glycine Backbone", "Molecules", 2013, pp. 287-310, vol. 18.

Tilani, N., et al., "Evaluting the Effect of Ionic Strength on Duplex Stability for PNA Having Negatively or Positively Charged Side Chains", "PLOS One", Mar. 2013, Page(s) e:58670; 1-8, vol. 8, No. 3.

Tilani, N., et al., "Differential DNA and RNA Sequence Discrimination by PNA Having Charged Side Chains", "Bioorganic and Medicinal Chemistry Letters", 2014, pp. 2360-2363, vol. 24.

Vernille, J.P., et al., "Peptide Nucleic Acid (PNA) Amphiphiles: Synthesis, Self-Assembly, and Duplex Stability", "Bioconjugate Chem.", 2004, pp. 1314-1321, vol. 15.

\* cited by examiner (A)

(B)

(A)

(B)

(C)

(D)

(A)

HeLa (B)

SW480

(C)

SK-BR-3

SW480

SK-BR-3

PEPTIDE NUCLEIC ACID COMPLEX HAVING IMPROVED CELL PERMEABILITY AND PHARMACEUTICAL COMPOSITION COMPRISING SAME

CROSS-REFERENCE TO RELATED APPLICATIONS

This application is a U.S. national phase under the provisions of 35 U.S.C. § 371 of International Patent Application No. PCT/KR17/08636 filed Aug. 9, 2017, which in turn claims priority of Korean Patent Application No. 10-2016-0101374 filed Aug. 9, 2016. The disclosures of such International Patent Application No. PCT/KR17/08636 and Korean Patent Application No. 10-2016-0101374 are hereby incorporated herein by reference in their respective entireties, for all purposes.

TECHNICAL FIELD

The present invention relates to a nucleic acid complex having a novel structure, which can introduce a bioactive nucleic acid into cells, a composition for treating and diagnosing disease, which comprises the same, and a method of regulating expression of a target gene using the same, and more particularly to a nucleic acid complex comprising a bioactive nucleic acid complementarily bound to a carrier peptide nucleic acid modified to be generally positively charged, a composition for treating and diagnosing disease, which comprises the same, and a method of regulating expression of a target gene using the same.

BACKGROUND ART

Conventionally, the exploration of new drugs is based on screening various compounds through computer research, and the majority of screened compounds target proteins.

Unlike traditional drugs, nucleic acid drugs inhibit the expression of target-specific messenger RNA (mRNA), making it possible to address research areas in which diseases could not be treated by conventional drugs that target proteins (Kole R. et al., Nature Rev. Drug Discov. 2012; 11; 125-140, Wilson C. et al., Curr. Opin. Chem. Bio. 2006; 10: 607-614.).

Despite the excellent effects and various applications of gene expression regulation based on oligo-nucleic acids, there are a number of obstacles to overcome in the development of nucleic acid-based therapeutic agents. For example, oligo-nucleic acids are at risk of damage by nuclease and the like, and the passage of oligo-nucleic acids through the cell membrane by passive diffusion is impossible due to the electrical properties (charges) and size of these oligo-nucleic acids. To overcome these problems, efforts have been continuously made to ensure biological stability through nucleic acid modification. For modified artificial nucleic acids, it becomes possible to increase their affinity for target nucleic acids without loss of biological activity.

Peptide nucleic acid (PNA), a kind of modified artificial nucleic acid, is an artificial nucleic acid having a (2-aminoethyl)-glycine peptide backbone introduced therein, and has the property of strongly binding to RNA and DNA, each having a nucleotide sequence complementary thereto. In particular, the peptide nucleic acid is resistant to nuclease and has high biological stability, and thus studies on therapeutic agents based on various oligo-nucleic acids have been conducted. However, the peptide nucleic acid has a disadvantage in that it is difficult to introduce into cells, because it is electrically neutral in nature (Joergensen M. et al., Oligonucleotides 2011, 21; 29-37.).

Owing to the performance and advantages of nucleic acids as drugs, various clinical trials using nucleic acids are in progress. Despite the increasing applications of nucleic acid-based therapeutic acids, the use of carriers for intracellular introduction is extremely limited. For example, clinical trials have been performed using a strategy (method) that delivers oligo-nucleic acid-based drugs into cells or tissues by use of nanoparticles, cationic liposomes and polymeric nanoparticles. However, most of these clinical trials do not include delivery systems, and rely mainly on direct introduction of nucleic acids by parenteral administration routes, including intramuscular injection, intraocular administration, subcutaneous injection and the like.

In addition, the cell membrane permeability of oligo-nucleic acids themselves is considerably low, and in particular, DNA or RNA is negatively charged. For this reason, these oligo-nucleic acids cannot pass through the hydrophobic phospholipid bilayer of the cell membrane, and thus are difficult to deliver into cells through simple diffusion. The use of a virus carrier such as retrovirus or AAV (adeno-associated virus) makes it possible to introduce oligo-nucleic acids into cells, but has risks, such as unintended immune activity and the possible recombination of oncogenes (Couto L. B. et al., Curr. Opin. Pharmacol. 2010, 5; 534-542.).

For this reason, the development of nucleic acid carriers based on non-viral oligo-nucleic acids having low cytotoxicity and low immune activity is of increasing importance. As a result, techniques of introducing nucleic acids using cationic lipids, liposomes, stable nucleic acid lipid particles (SNALPs), polymers and cell-penetrating peptides have been developed (Zhi D. et al., Bioconjug. Chem. 2013, 24; 487-519, Buyens K. et al., J. Control Release, 2012, 158; 362-70, ROSSI, J. J. et al., Gene Ther. 2006, 13: 583-584, Yousefi A. et al., J. Control Release, 2013, 170; 209-18, Trabulo S. et al., Curr. Pharm. Des. 2013, 19; 2895-923.).

These nucleic acid delivery techniques have functional moieties by direct binding, include a complex formation step, and have problems associated with the endosomal escape efficiency of liposome structures, in vivo toxicity, and the like. Consequently, it is required to improve the function of introducing oligo-nucleic acids and overcome problems associated with production procedures and side effects.

Under this technical background, the present inventors have made extensive efforts to develop a new structure having low cytotoxicity, an ability to allow a bioactive nucleic acid to permeate into cells, and an increased ability to regulate gene expression, and as a result, have found that a nucleic acid complex comprising a bioactive nucleic acid complementarily bound to a carrier peptide nucleic acid modified to be generally positively charged has a surprisingly increased cell permeability, and expression of a target gene can be very efficiently regulated using the nucleic acid complex, thereby completing the present invention.

DISCLOSURE OF INVENTION

The present invention has been made to solve the above-described problems, and it is an object of the present invention to provide a nucleic acid complex comprising a bioactive nucleic acid complementarily bound to a carrier peptide nucleic acid modified to be generally positively charged, a composition for treating and diagnosing disease, which comprises the same, and a method of regulating expression of a target gene using the same.

Another object of the present invention is to provide a method for treating disease, which comprises administering a nucleic acid complex according to the present invention and/or a pharmaceutical composition comprising the same to a patent in need of treatment.

To achieve the above object, the present invention provides a nucleic acid complex having a structure represented by the following structural formula (1):

[A≡C$^{(+)}$],                                      [Structural formula (1)]

wherein

A represents a bioactive nucleic acid having either a sequence capable of binding to a target gene or a target gene sequence;

C represents a carrier peptide nucleic acid capable of binding to the bioactive nucleic acid;

'≡' represents complementary binding between the bioactive nucleic acid and the carrier peptide nucleic acid;

the bioactive nucleic acid represented by A is generally negatively charged or neutral;

C$^{(+)}$ indicates that the carrier peptide nucleic acid is generally positively charged; and the carrier peptide nucleic acid comprises one or more peptide nucleic acid monomers modified such that the carrier peptide nucleic acid is generally positively charged.

The particle size of the nucleic acid complex represented by structural formula (1) may be controlled by suitably controlling the charge balance between the bioactive nucleic acid and the carrier peptide nucleic acid.

Specifically, as the positive charges of the carrier peptide nucleic acid increase, the particle size of the nucleic acid complex becomes smaller, but if the positive charges of the carrier peptide nucleic acid exceed a certain level, then the particle size of the nucleic acid complex becomes larger. In addition, the particle size of the nucleic acid complex is determined by proper charge balance between the bioactive nucleic acid and the carrier peptide nucleic acid with the charges of the bioactive peptide nucleic acid of the complex.

The number of positive charges of the carrier peptide nucleic acid according to the present invention is 1 to 7 (indicating that 2 to 5 positively charged monomers are included), preferably 2 to 5, most preferably 2 to 3, and the number of net negative charges of the bioactive nucleic acid for charge balance is 0 to 5, preferably 0 to 3.

The particle size of the nucleic acid complex according to the present invention is 5 to 300 nm, preferably 10 to 80 nm, most preferably 15 to 70 nm.

Thus, the present invention also provides a method of controlling the particle size of a nucleic acid complex represented by structural formula (1), which comprises controlling the charge balance of the nucleic acid complex.

The present invention also provides a composition for preventing and treating disease, which comprises the nucleic acid complex represented by structural formula (1), a composition for diagnosing disease, which comprises the nucleic acid complex represented by structural formula (1), and a composition for regulating expression of a target gene, which comprises the nucleic acid complex represented by structural formula (1).

The present invention also provides a kit for diagnosing disease, which comprises the nucleic acid complex represented by structural formula (1).

The present invention also provides a method of regulating expression of a target gene using a complex, the method comprising the steps of: (a) forming the complex by binding of a bioactive nucleic acid to a carrier peptide nucleic acid; and (b) introducing the complex into target cells by bringing the complex into contact with the target cells.

The present invention also provides a method for treating disease, which comprises administering a nucleic acid complex according to the present invention and/or a pharmaceutical composition comprising the same to a patient in need of treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(A): a bioactive nucleic acid alone;

(B): a nucleic acid complex comprising a bioactive peptide nucleic acid bound parallel to a carrier peptide nucleic acid.

Figure 2A:
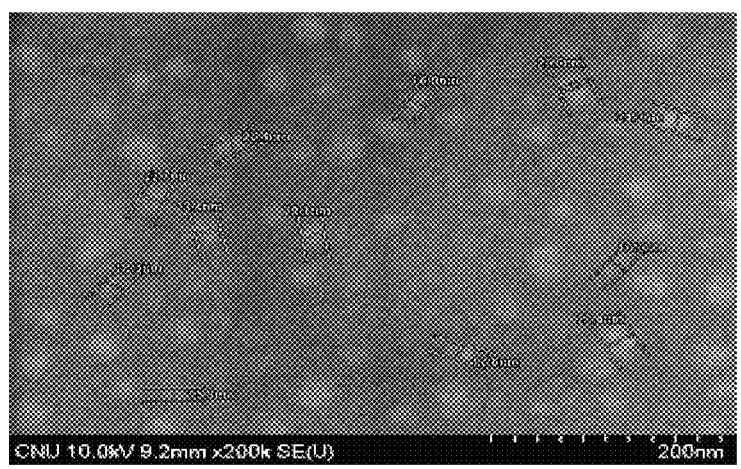
Figure 2A:
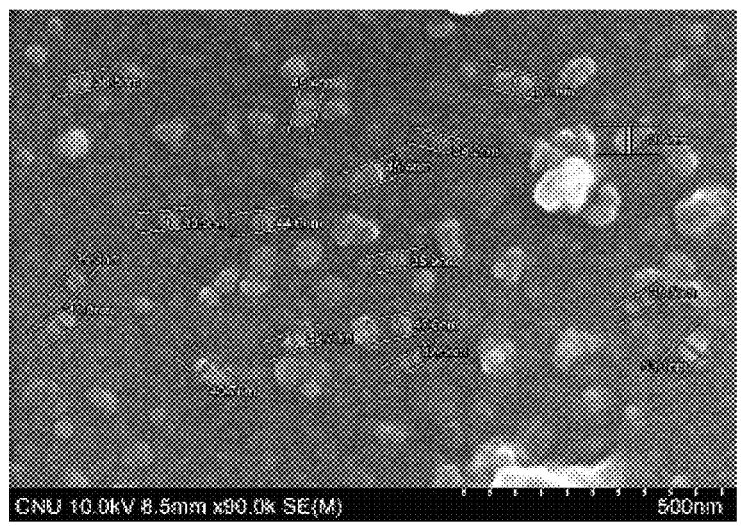
Figure 2B:
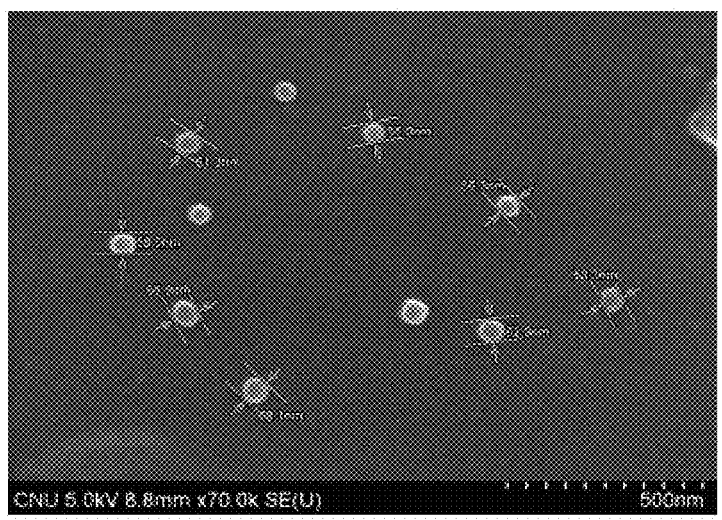
Figure 2B:
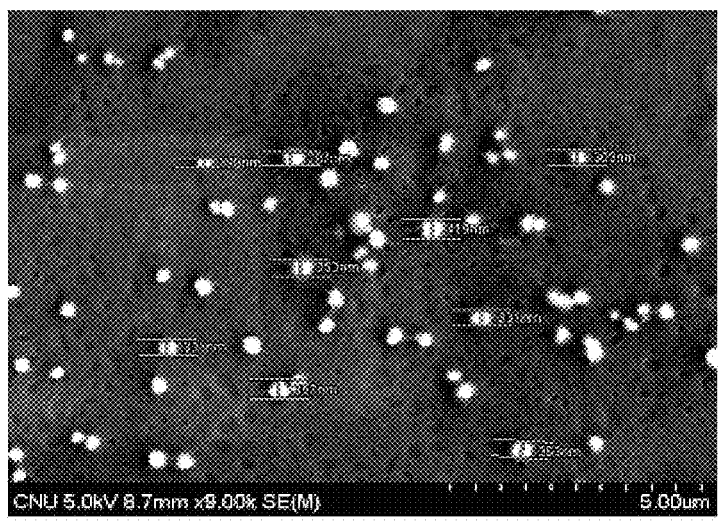

FIGS. 2a and 2b are SEM photographs showing the results of observing the changes in morphology and size of complex particles with a change in the electrical properties of the bioactive peptide nucleic acid and carrier peptide nucleic acid of the nucleic acid complex represented by structural formula (1).

(A): PNA Duplex 1 (a complex of a bioactive peptide nucleic acid (SEQ ID NO: 6) and a carrier peptide nucleic acid (SEQ ID NO: 32));

(B): PNA Duplex 2 (a complex of a bioactive peptide nucleic acid (SEQ ID NO: 5) and a carrier peptide nucleic acid (SEQ ID NO: 32));

(C): PNA Duplex 3 (a complex of a bioactive peptide nucleic acid (SEQ ID NO: 1) and a carrier peptide nucleic acid (SEQ ID NO: 37));

(D): PNA Duplex 4 (a complex of a bioactive peptide nucleic acid (SEQ ID NO: 1) and a carrier peptide nucleic acid (SEQ ID NO: 23)).

Figure 3A:
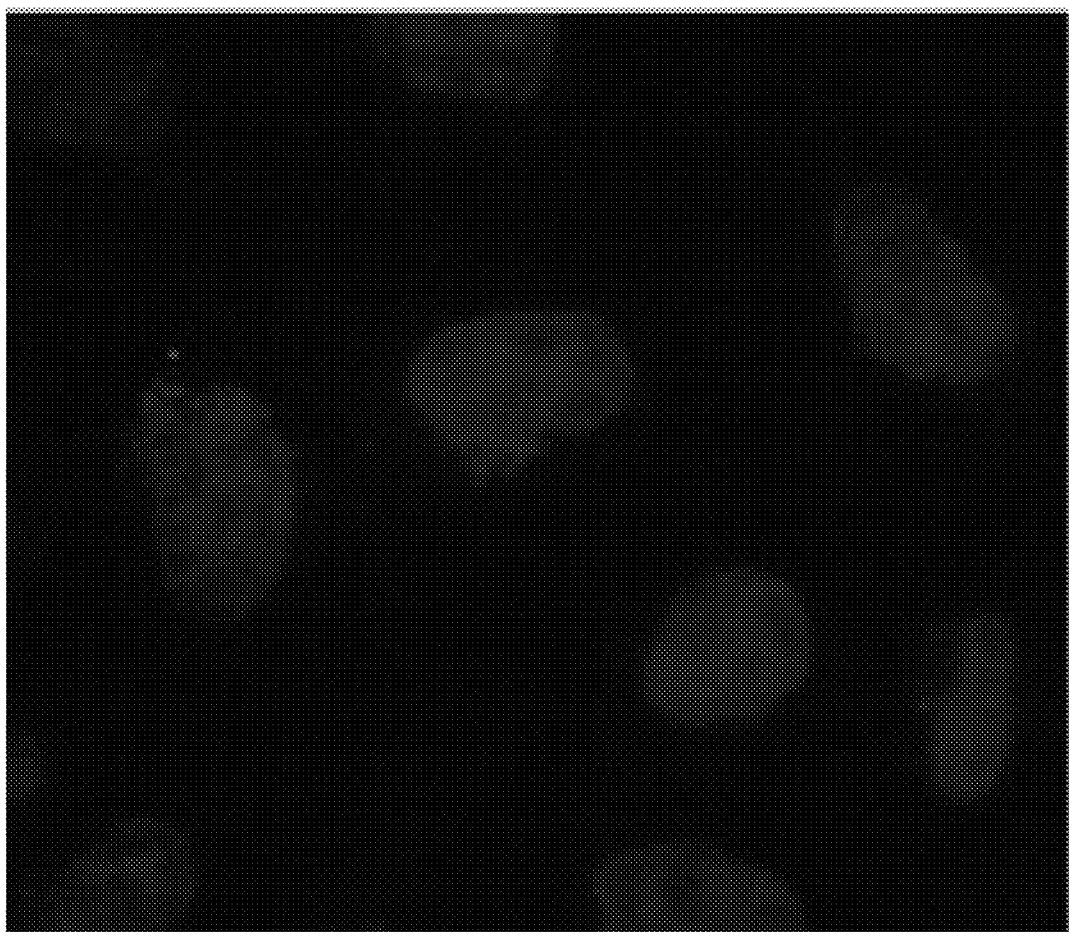
Figure 3B:
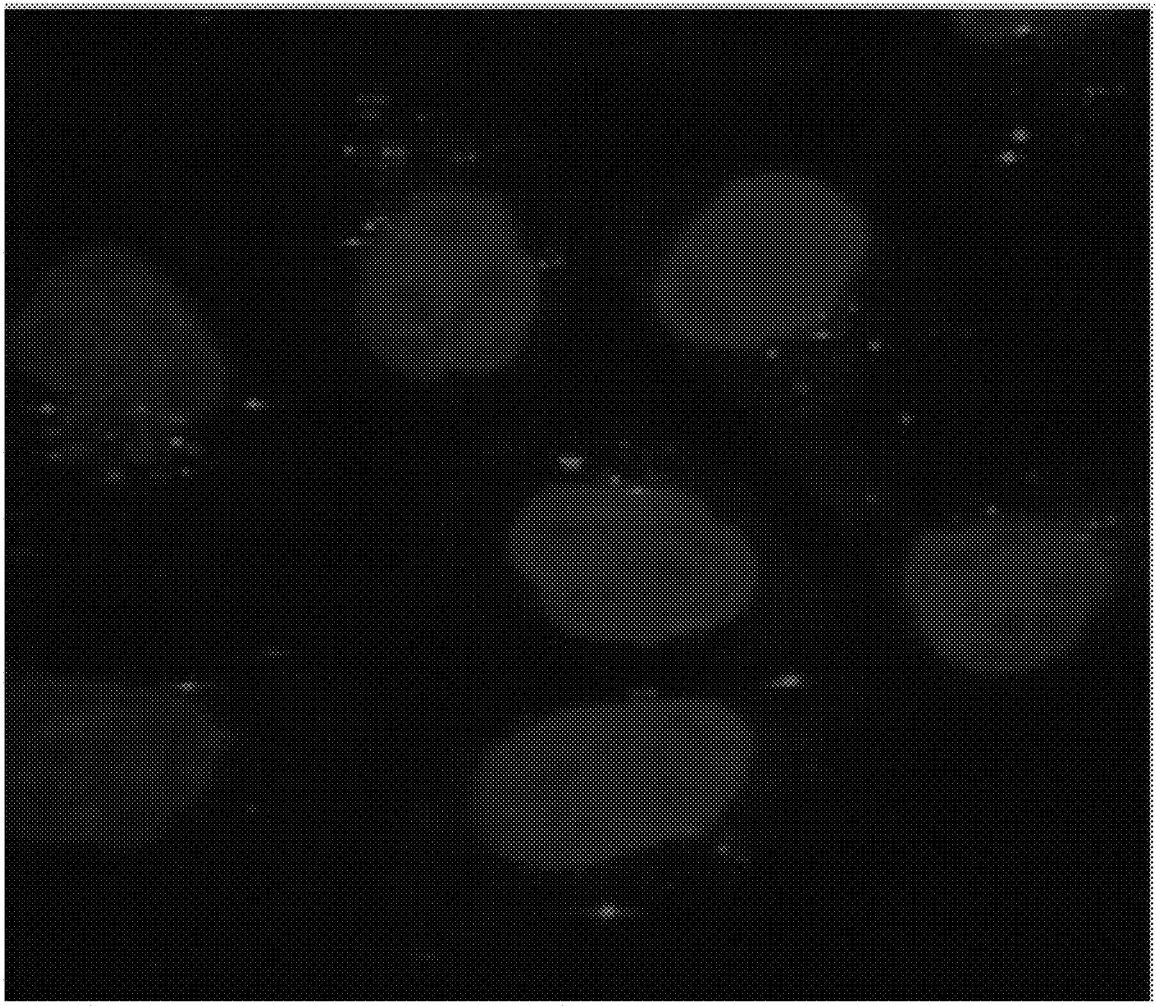
Figure 3C:
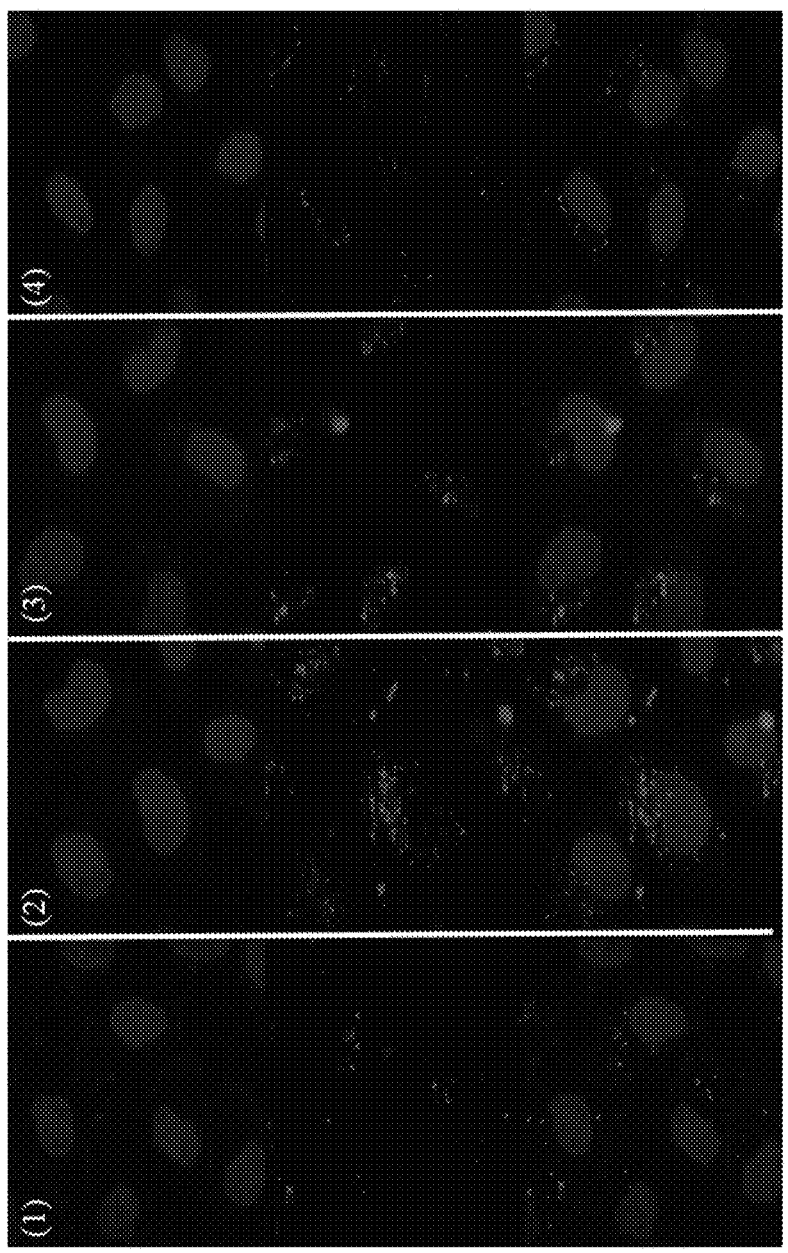

FIGS. 3a to 3c are photographs taken under a confocal microscope to analyze the cell permeability of a nucleic acid complex of the present invention according to the binding between a bioactive peptide nucleic acid and a carrier peptide nucleic acid and the electrical properties thereof.

(a): the case in which a complex comprising a non-charged bioactive peptide nucleic acid (SEQ ID NO: 13) and a carrier peptide nucleic acid (SEQ ID NO: 38) was used;

(b): the case in which a complex comprising a charged bioactive peptide nucleic acid (SEQ ID NO: 13) and a carrier peptide nucleic acid (SEQ ID NO: 40) was used; and (c): the case in which a complex comprising a bioactive peptide nucleic acid having various charges and a carrier peptide nucleic acid (SEQ ID NO: 40) having three positive charges was used;

(1): the case in which a complex comprising a bioactive peptide nucleic acid (SEQ ID NO: 15) and a carrier peptide nucleic acid (SEQ ID NO: 40) was used;

(2): the case in which a complex comprising a bioactive peptide nucleic acid (SEQ ID NO: 16) and a carrier peptide nucleic acid (SEQ ID NO: 40) was used;

(3): the case in which a complex comprising a bioactive peptide nucleic acid (SEQ ID NO: 14) and a carrier peptide nucleic acid (SEQ ID NO: 40) was used; and (4): the case in which a complex comprising a bioactive peptide nucleic acid (SEQ ID NO: 17) and a carrier peptide nucleic acid (SEQ ID NO: 40) was used.

Figure 4:
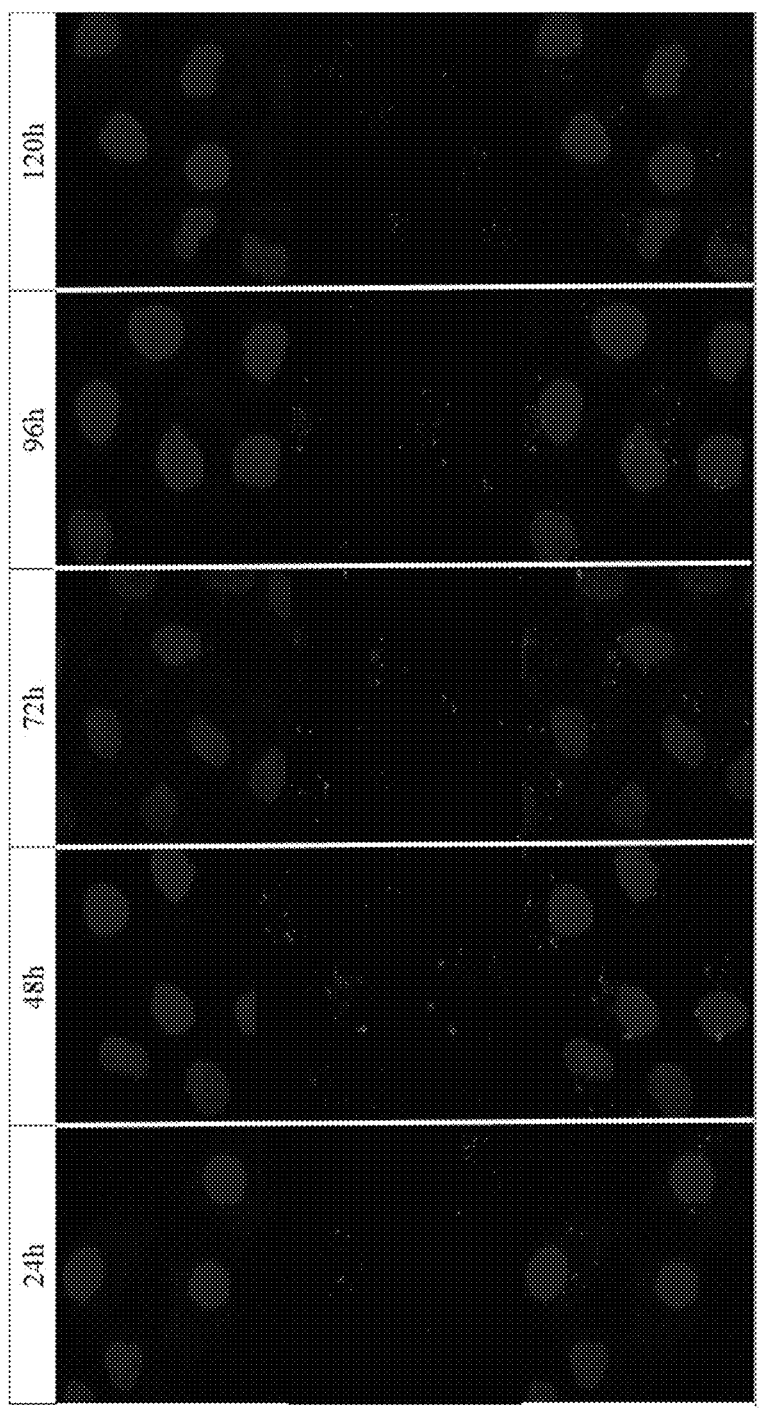
Figure 5A:
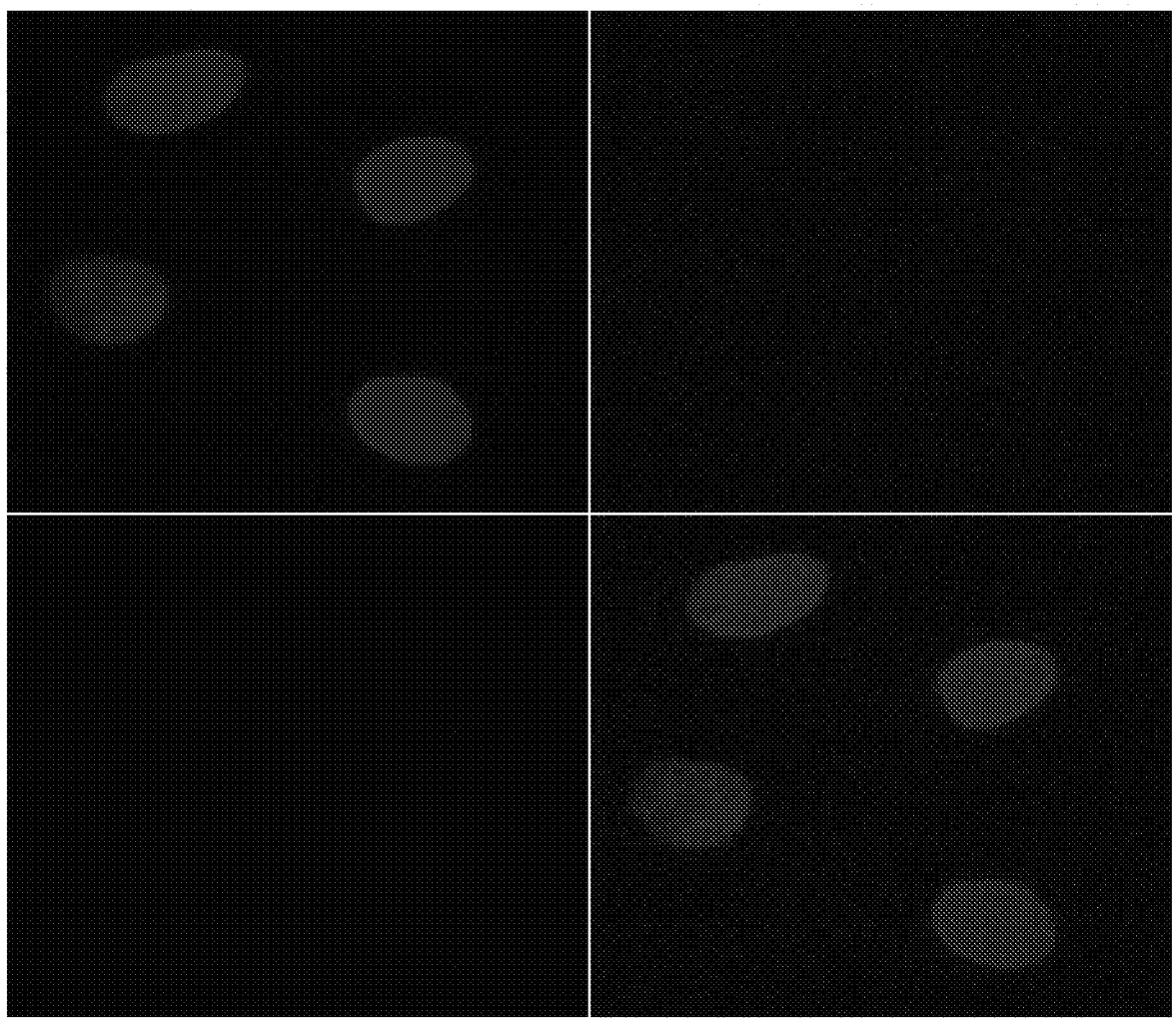
Figure 5B:
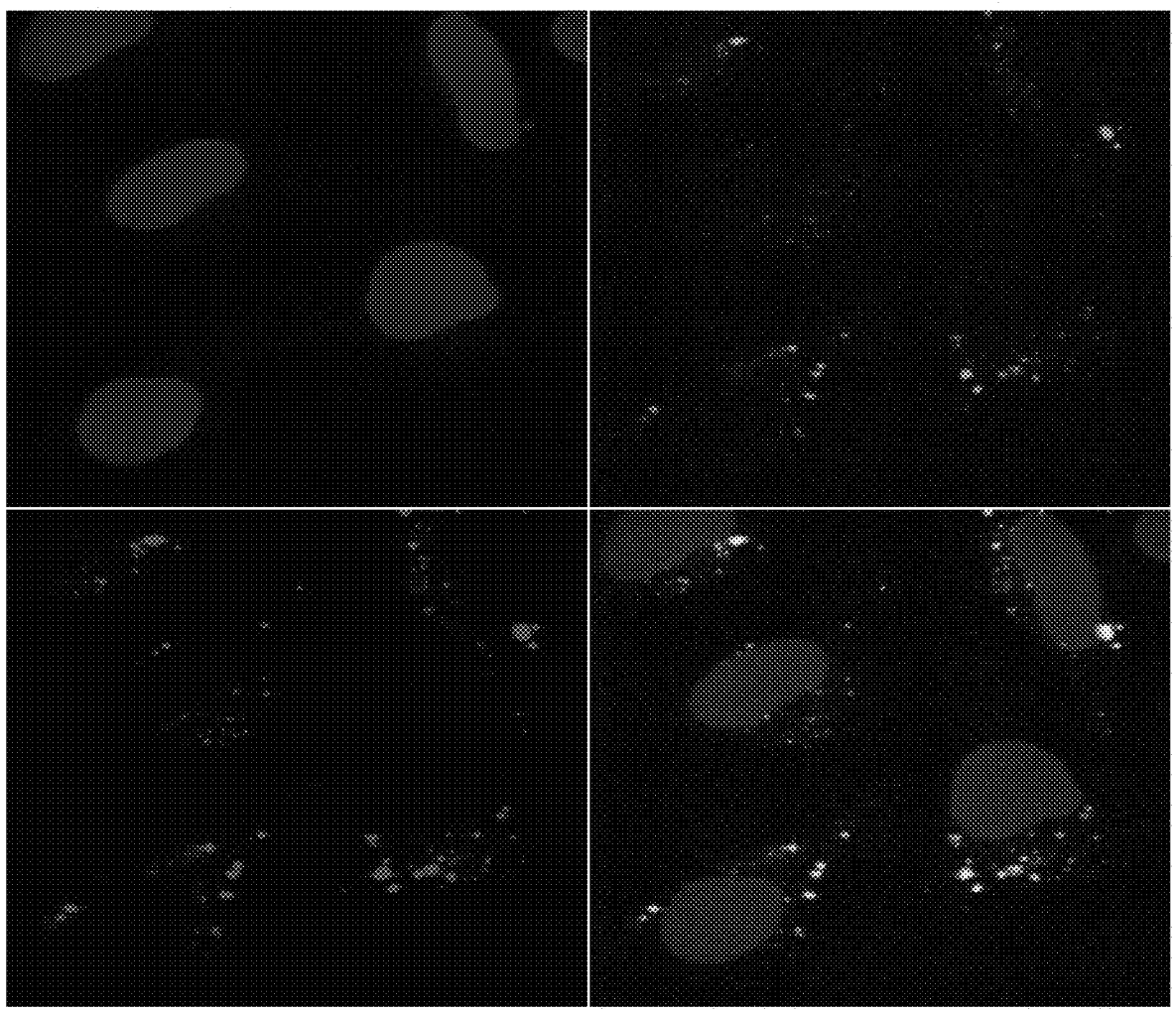
Figure 5C:
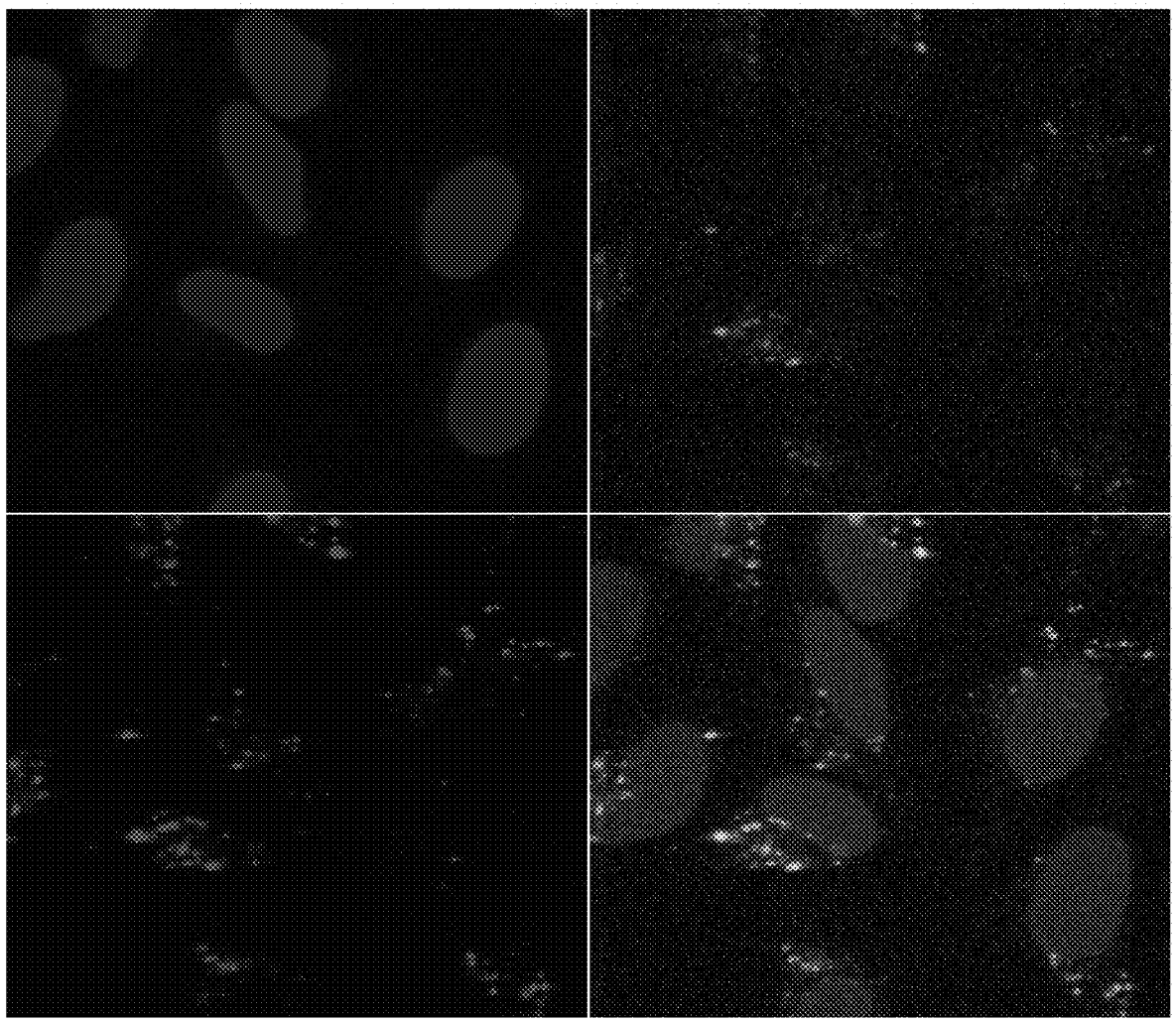
Figure 5D:
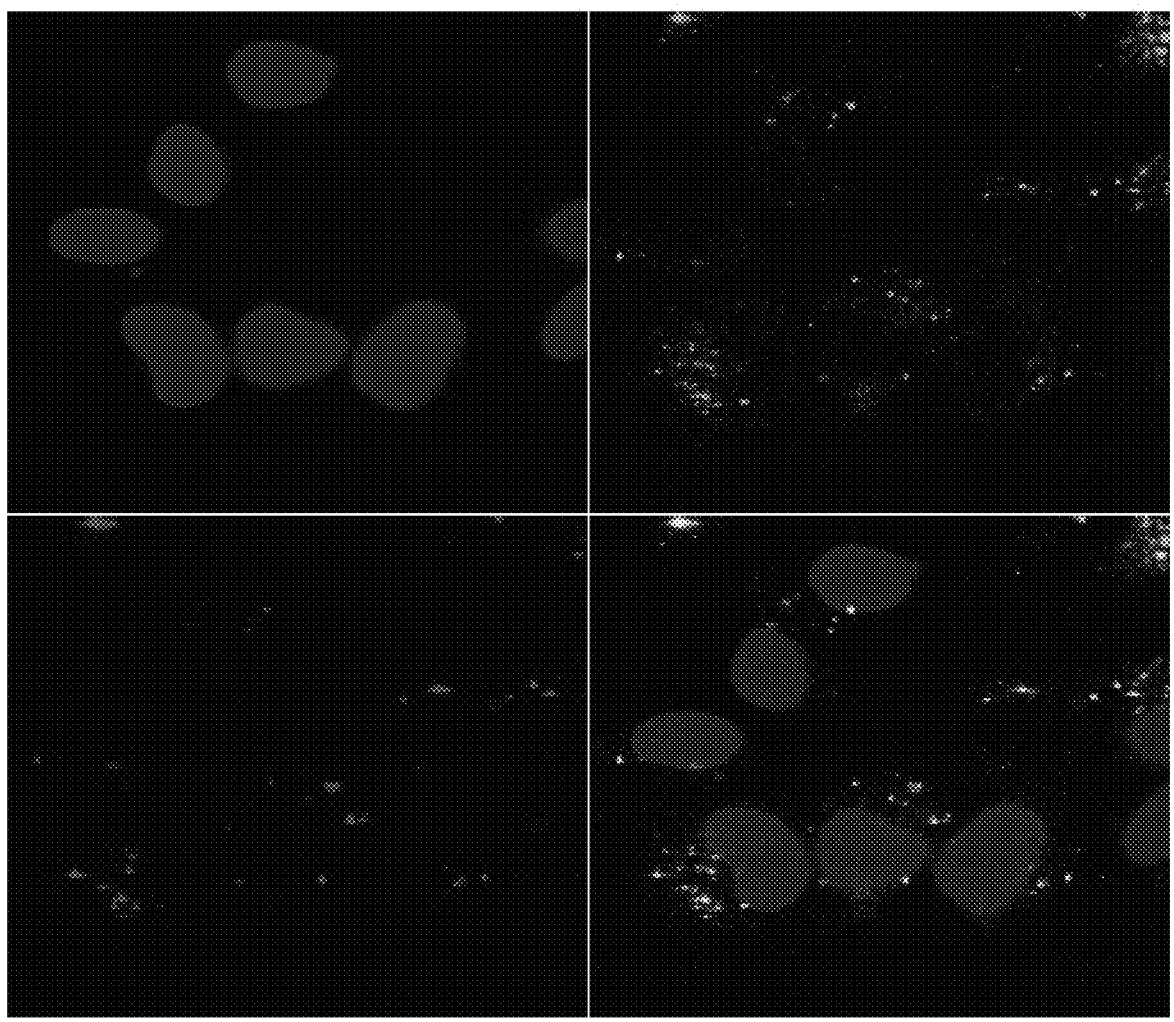
Figure 5E:
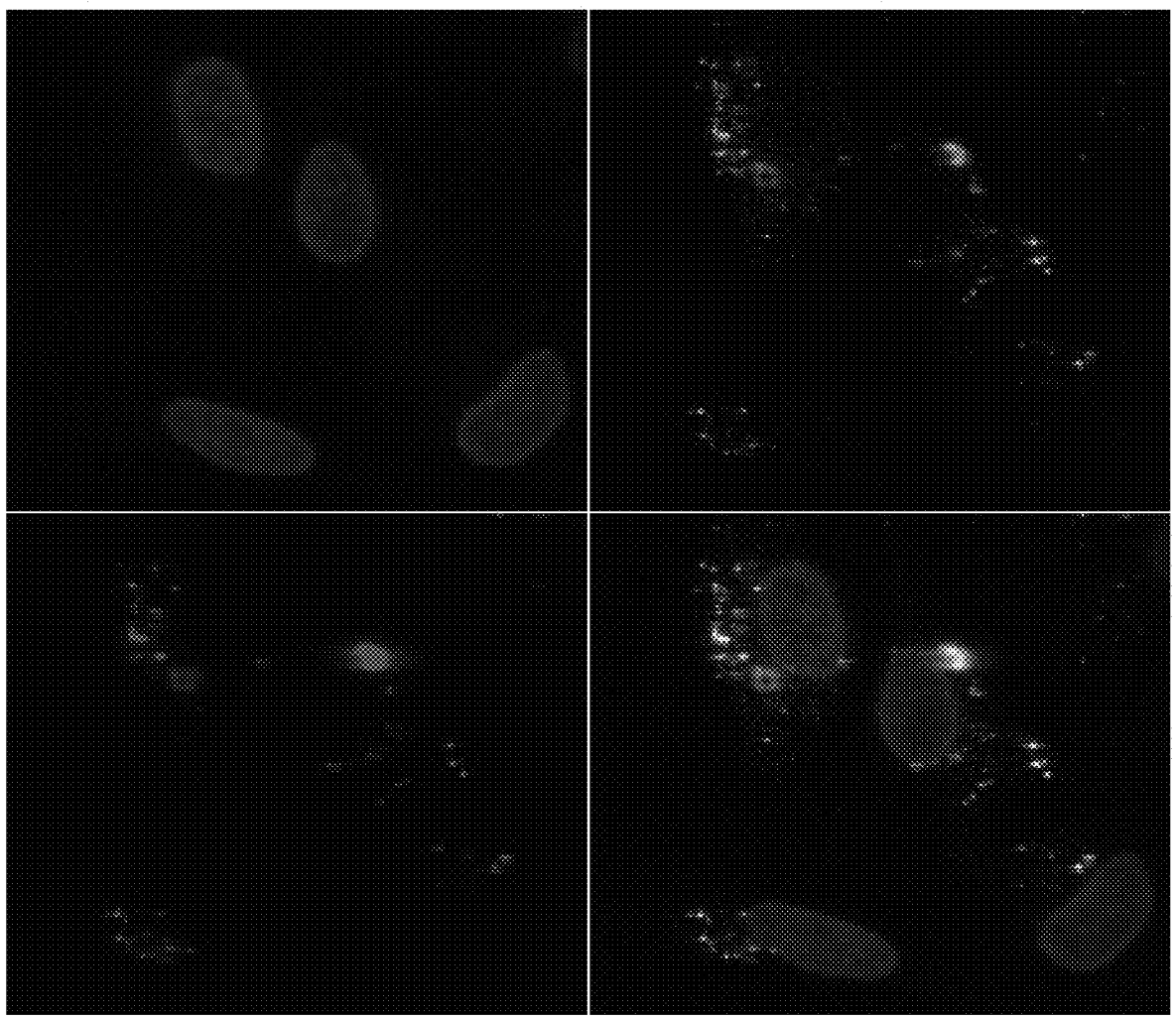
Figure 5F:
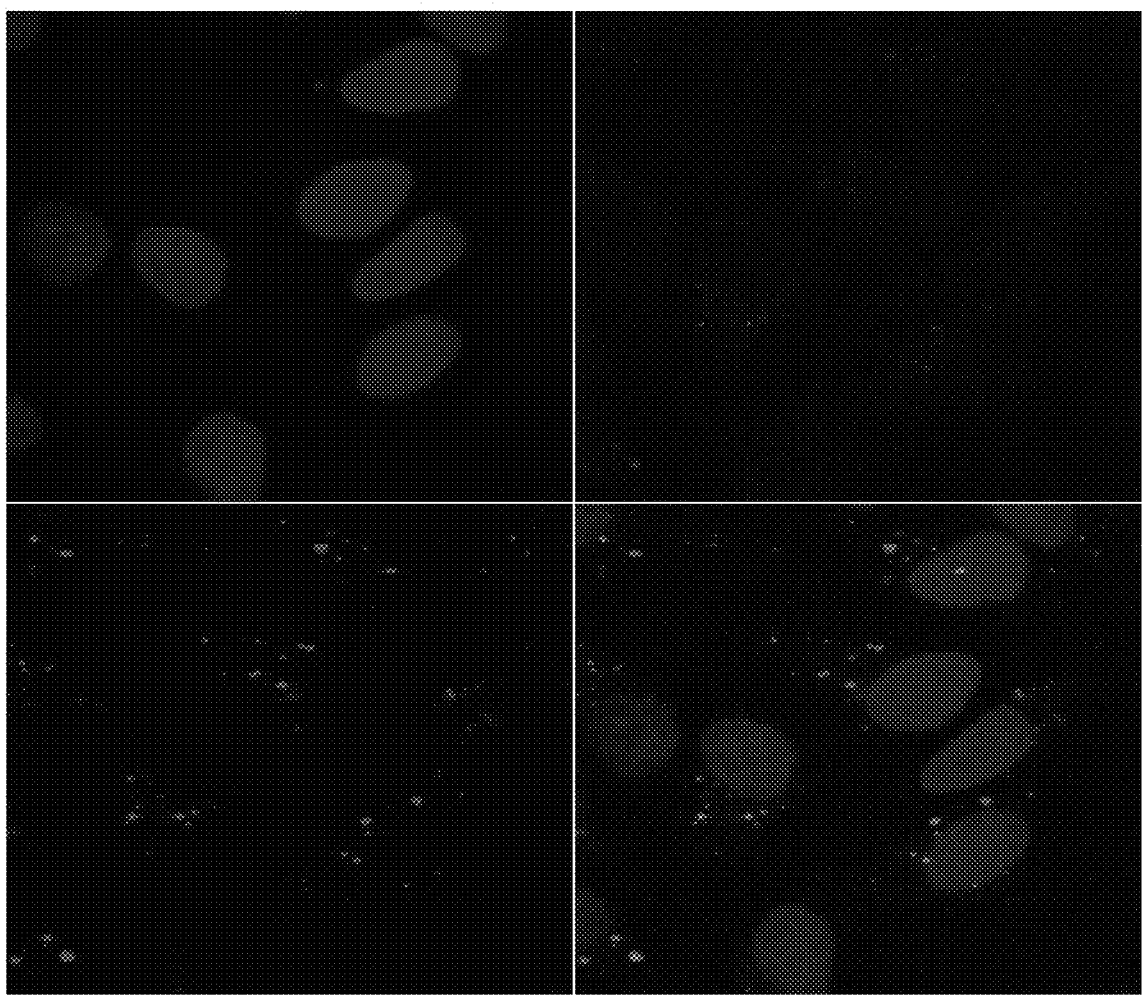
Figure 6A:
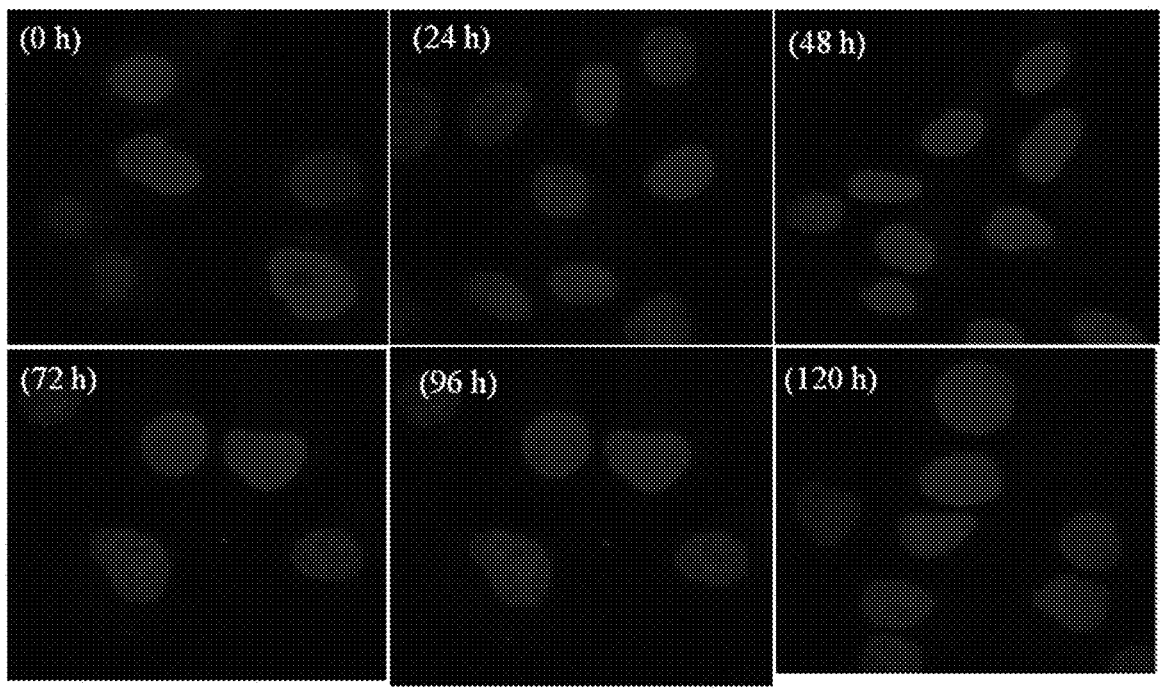
Figure 6B:
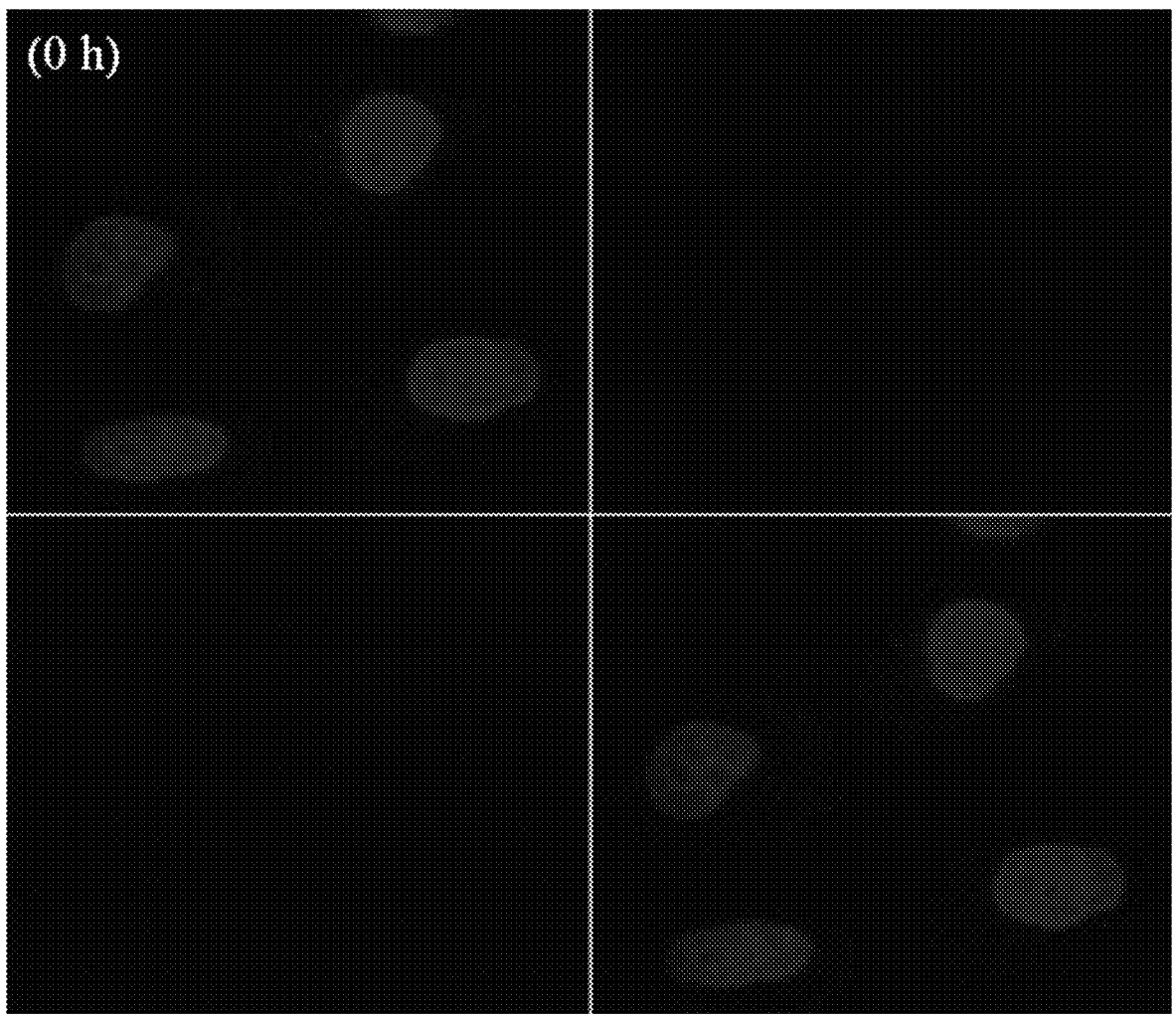
Figure 6C:
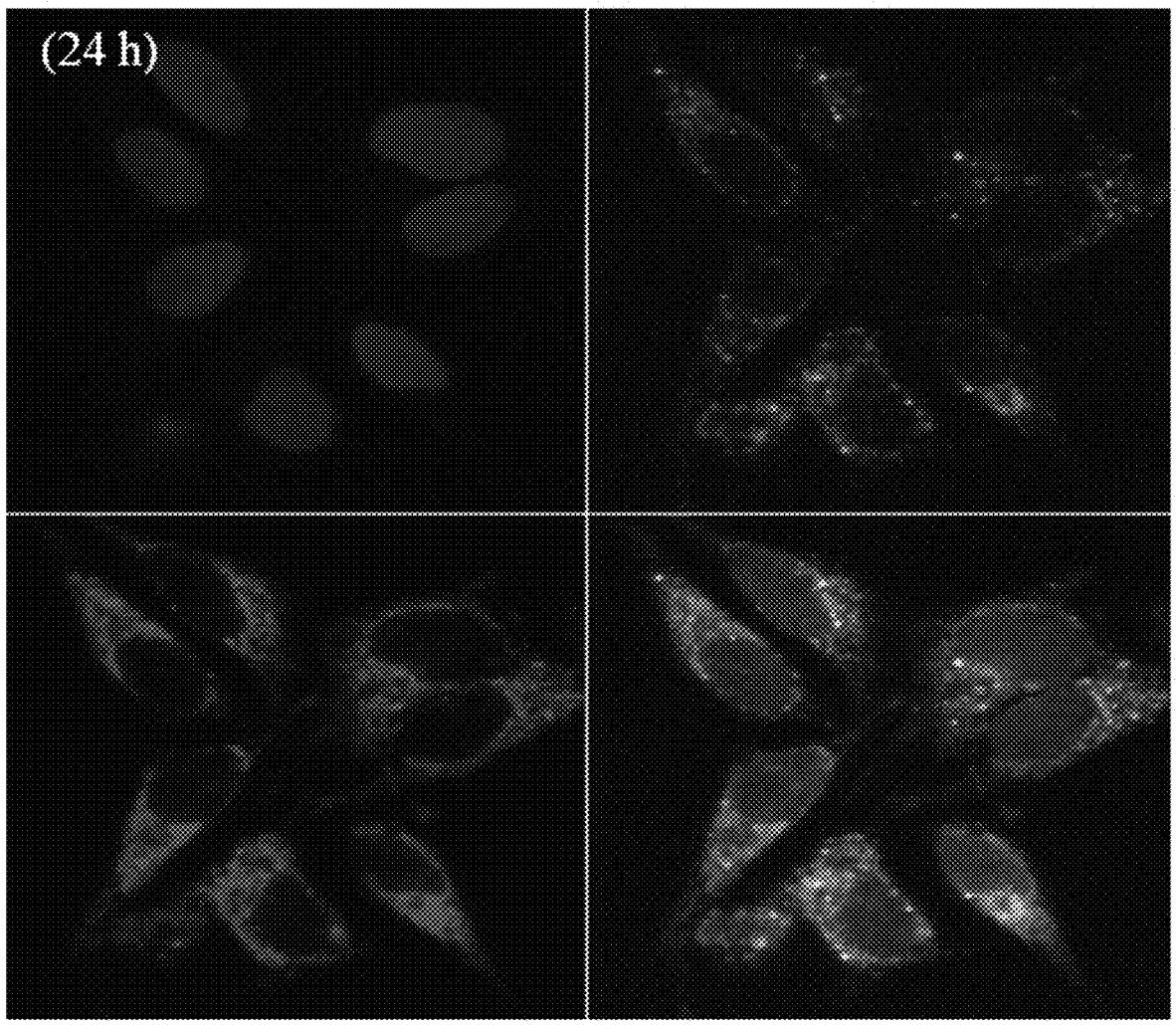
Figure 6D:
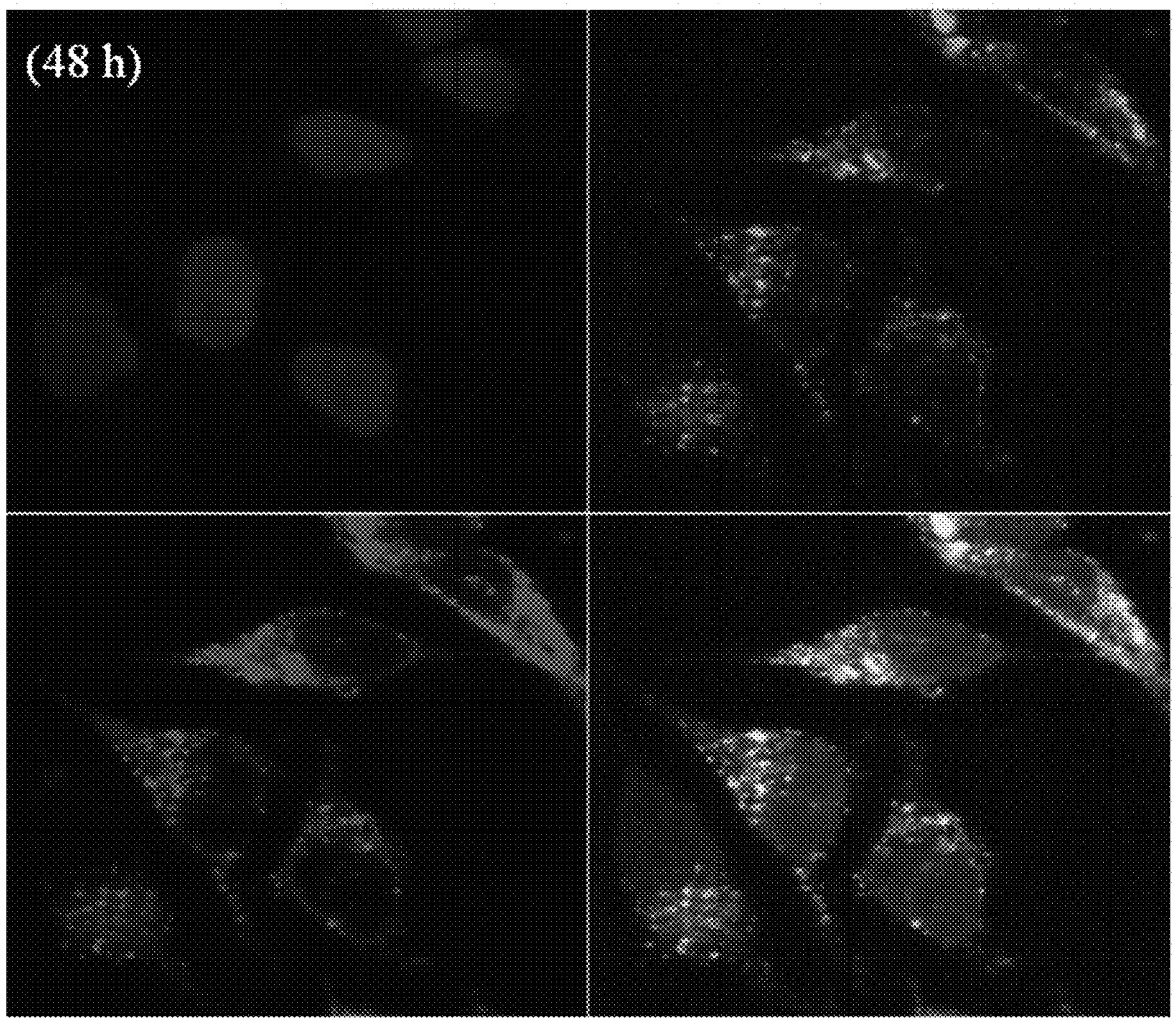
Figure 6E:
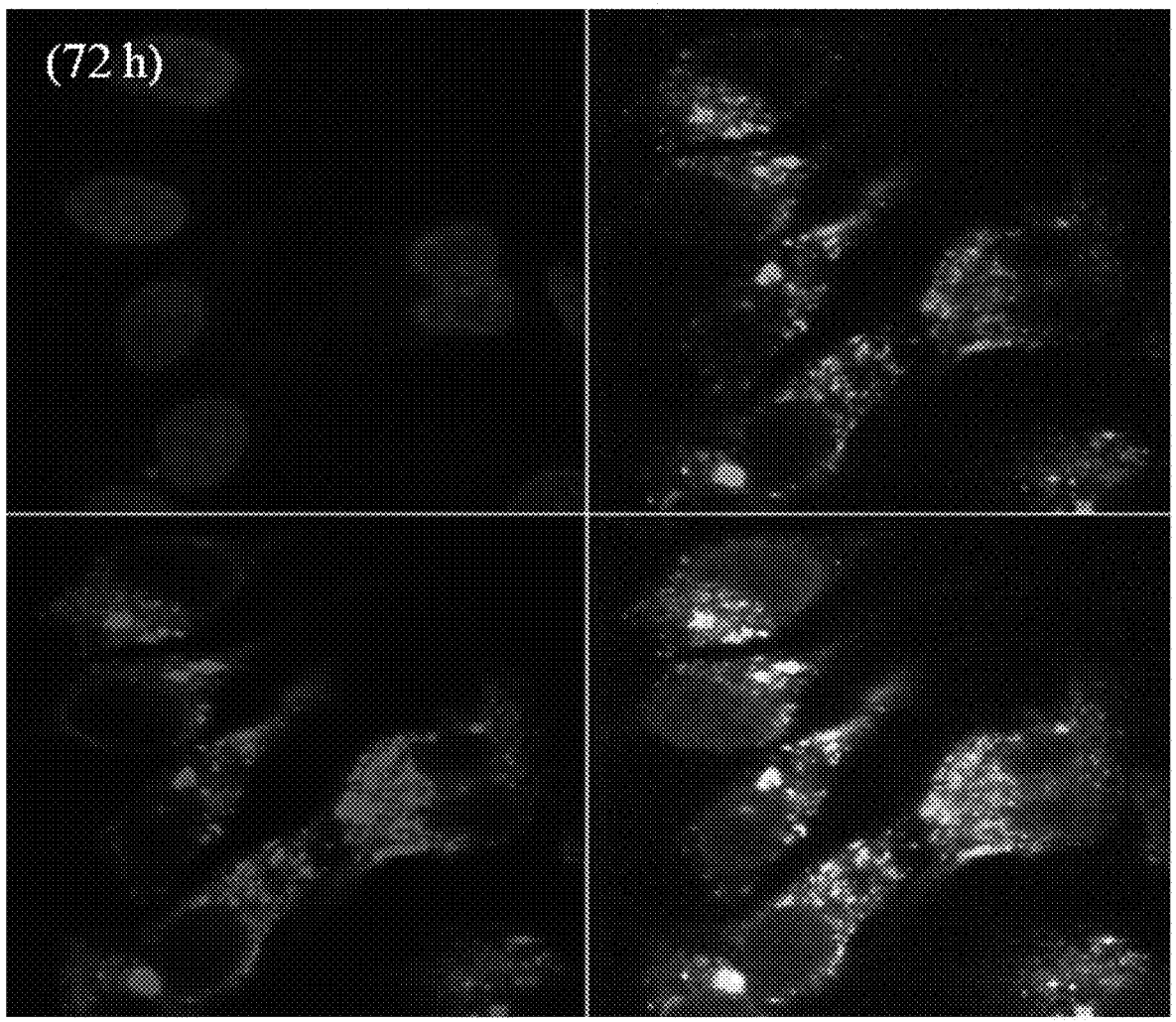
Figure 6F:
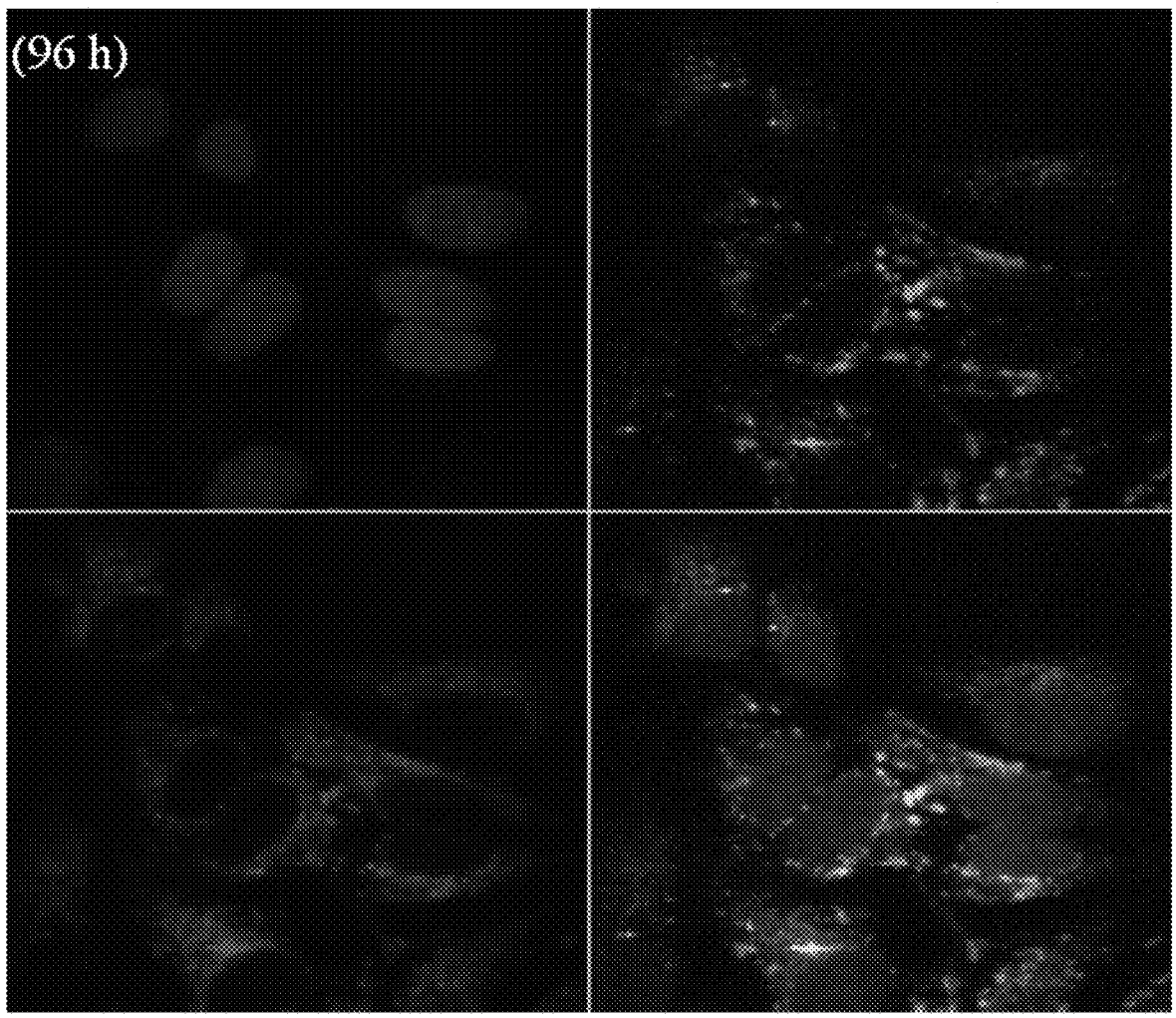
Figure 6G:
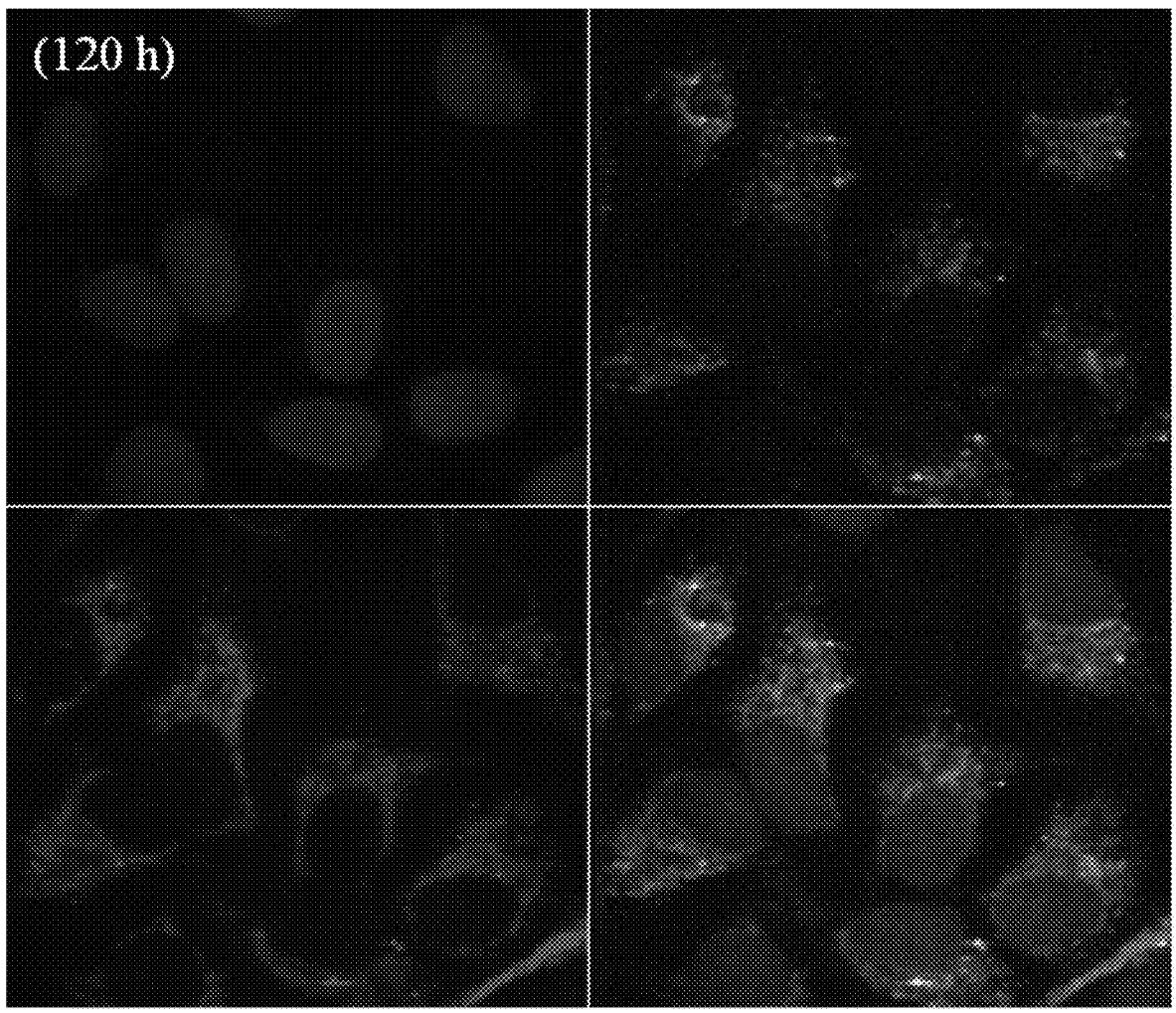

FIG. 4 shows the results of observing the intracellular presence or absence of a bioactive peptide nucleic acid complex with the passage of time when PNA was used as a carrier peptide nucleic acid in the nucleic acid complex represented by structural formula (1).

FIGS. 5a to 5f show the results of observing whether the nucleic acid complex represented by structural formula (1), which comprises a bioactive peptide nucleic acid and a carrier peptide nucleic acid, would be separated in cells with the passage of time.

(a): a control complex;
(b): a figure showing that a complex comprising a bioactive peptide nucleic acid (SEQ ID NO: 14) and a carrier peptide nucleic acid (SEQ ID NO: 39) maintains a complex form in cells after 24 hours;
(c): a figure showing that a complex comprising a bioactive peptide nucleic acid (SEQ ID NO: 14) and a carrier peptide nucleic acid (SEQ ID NO: 39) maintains a complex form or is separated in cells after 48 hours;
(d): a figure showing that a complex comprising a bioactive peptide nucleic acid (SEQ ID NO: 14) and a carrier peptide nucleic acid (SEQ ID NO: 39) is separated into the carrier peptide nucleic acid and the bioactive nucleic acid in cells after 72 hours;
(e): a figure showing that a complex comprising a bioactive peptide nucleic acid (SEQ ID NO: 14) and a carrier peptide nucleic acid (SEQ ID NO: 39) is separated into the carrier peptide nucleic acid and the bioactive nucleic acid in cells after 96 hours; and
(f): a figure showing that a complex comprising a bioactive peptide nucleic acid (SEQ ID NO: 13) and a carrier peptide nucleic acid (SEQ ID NO: 39) is separated into the carrier peptide nucleic acid and the bioactive nucleic acid in cells after 120 hours, and then remains in the cells.

FIGS. 6a to 6g show the results of confocal microscopy performed to examine intracellular permeation efficiency when a single siRNA was used alone and when a complex represented by structural formula (1) was used which comprises a single siRNA and a PNA as a carrier peptide nucleic acid (SEQ ID NO: 39).

(a): the case in which a single siRNA was used; and
(b) to (g): the case in which a complex comprising a single siRNA and carrier peptide nucleic acid (SEQ ID NO: 39) was used.

Figure 7:
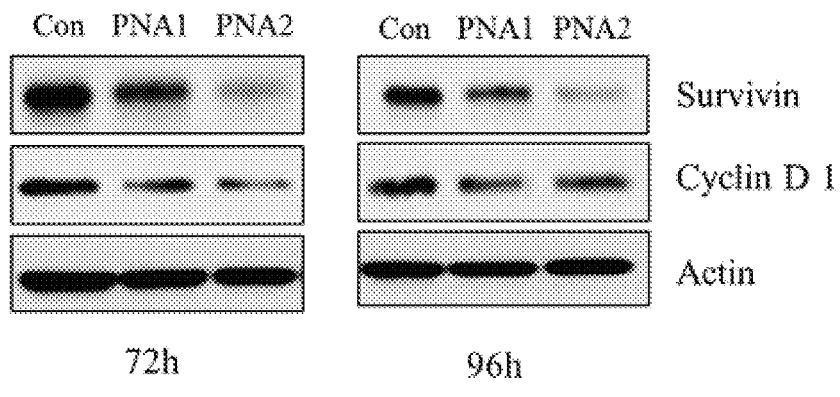
Figure 7:
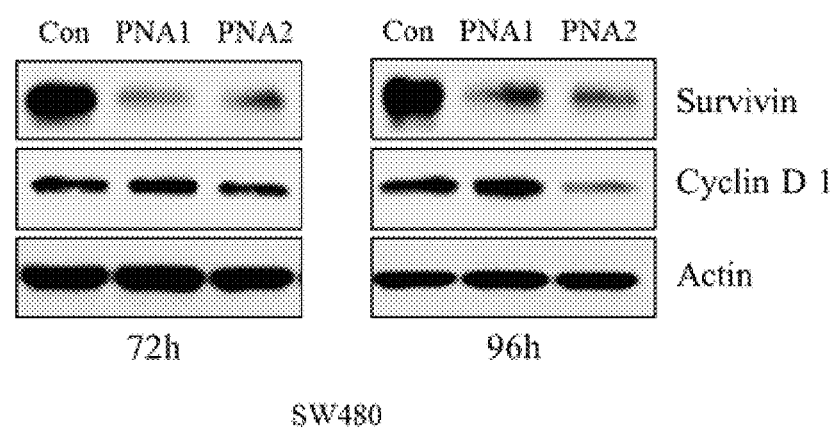
Figure 7:
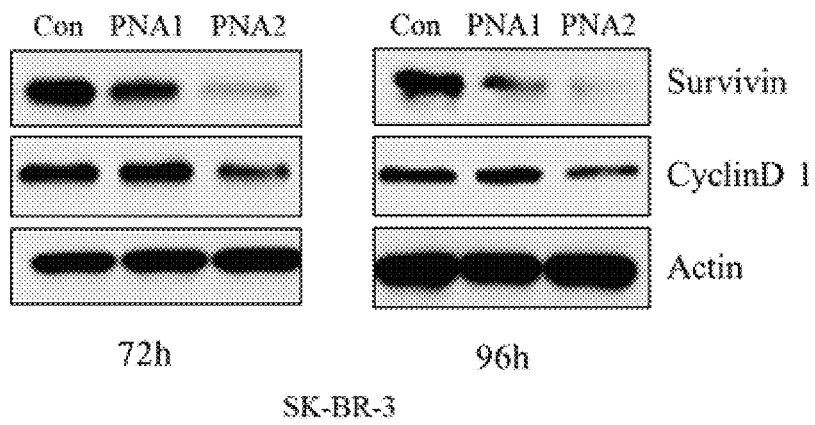
Figure 8A:
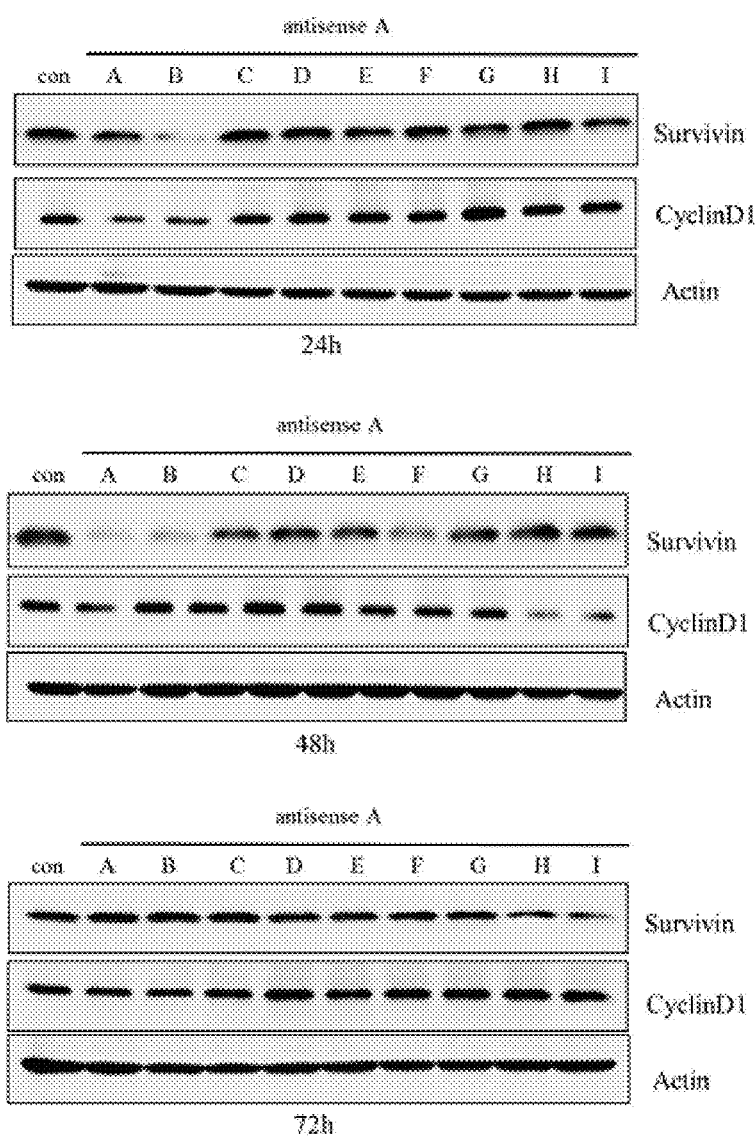
Figure 8B:
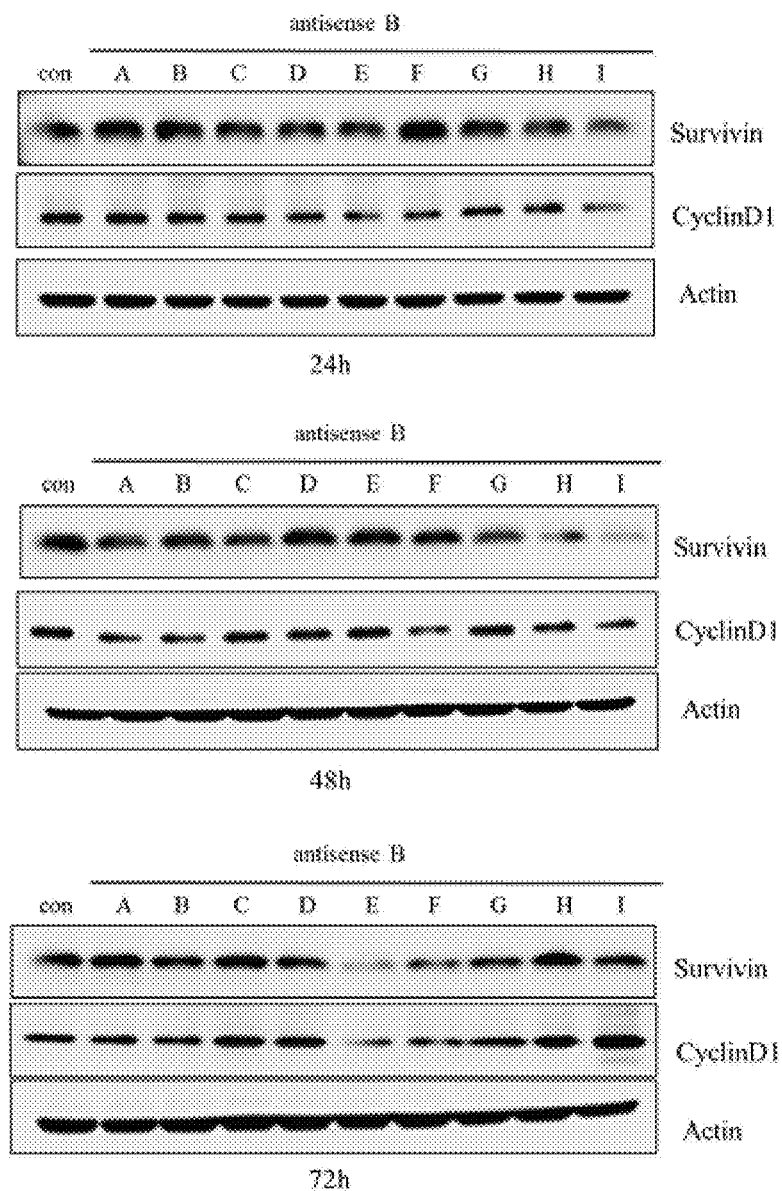
Figure 8C:
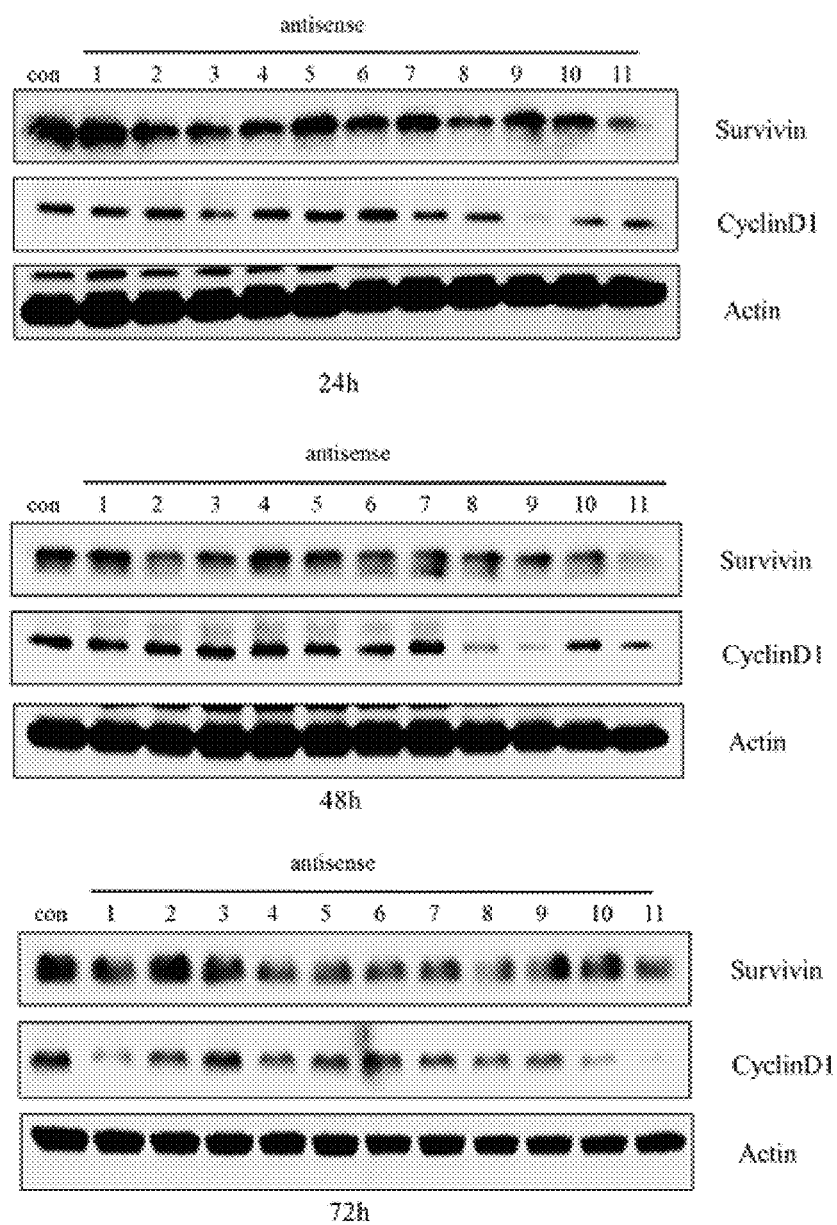
Figure 8D:
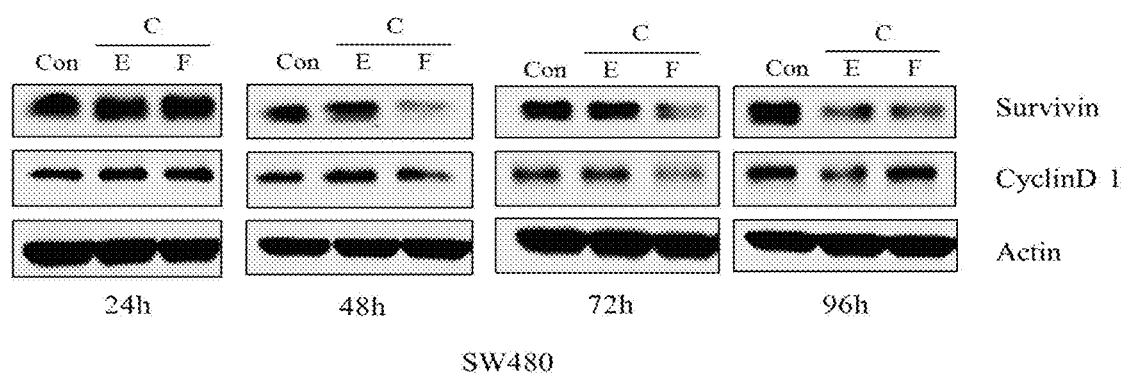
Figure 8E:
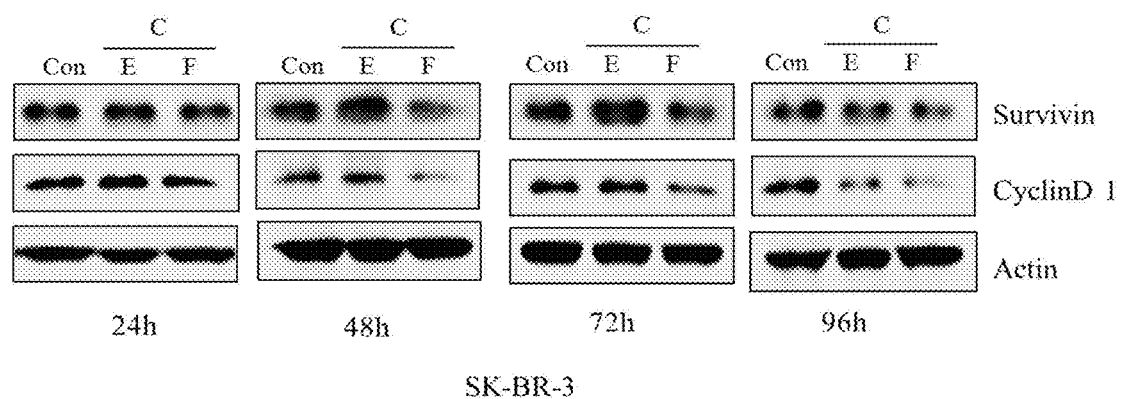

FIG. 7 shows that expression of survivin and downstream proteins in various cancer cell lines is inhibited by the nucleic acid complex represented by structural formula (1), which comprises a survivin-specific bioactive peptide nucleic acid.

(A): the results of an experiment of using the HeLa cell line;
(B): the results of an experiment of using the SW480 cell line; and
(C): the results of an experiment of using the SK-BR-3 cell line.

FIGS. 8a to 8e show that expression of survivin and its downstream proteins in various cancer cell lines is inhibited by the nucleic acid complex represented by structural formula (1), which comprises a survivin-specific bioactive peptide nucleic acid.

(a): the results of an experiment performed in the SW480 cell line using a complex comprising a non-charged bioactive peptide nucleic acid (SEQ ID NO: 1) and a peptide nucleic acid having various charges;

(b): the results of an experiment performed in the SW480 cell line using a complex comprising a bioactive peptide nucleic acid (SEQ ID NO: 2) and a peptide nucleic acid having various charges;
(c): the results of an experiment performed in the SW480 cell line using a complex comprising a bioactive peptide nucleic acid (SEQ ID NO: 6) and a peptide nucleic acid having various charges;
(d): the results of an experiment performed in the SW480 cell line using a complex comprising a bioactive peptide nucleic acid (SEQ ID NO: 12) and a peptide nucleic acid having various charges; and
(e): the results of an experiment performed in the SK-BR-3 cell line using a complex comprising a bioactive peptide nucleic acid (SEQ ID NO: 12) and a peptide nucleic acid having various charges.

Figure 9A:
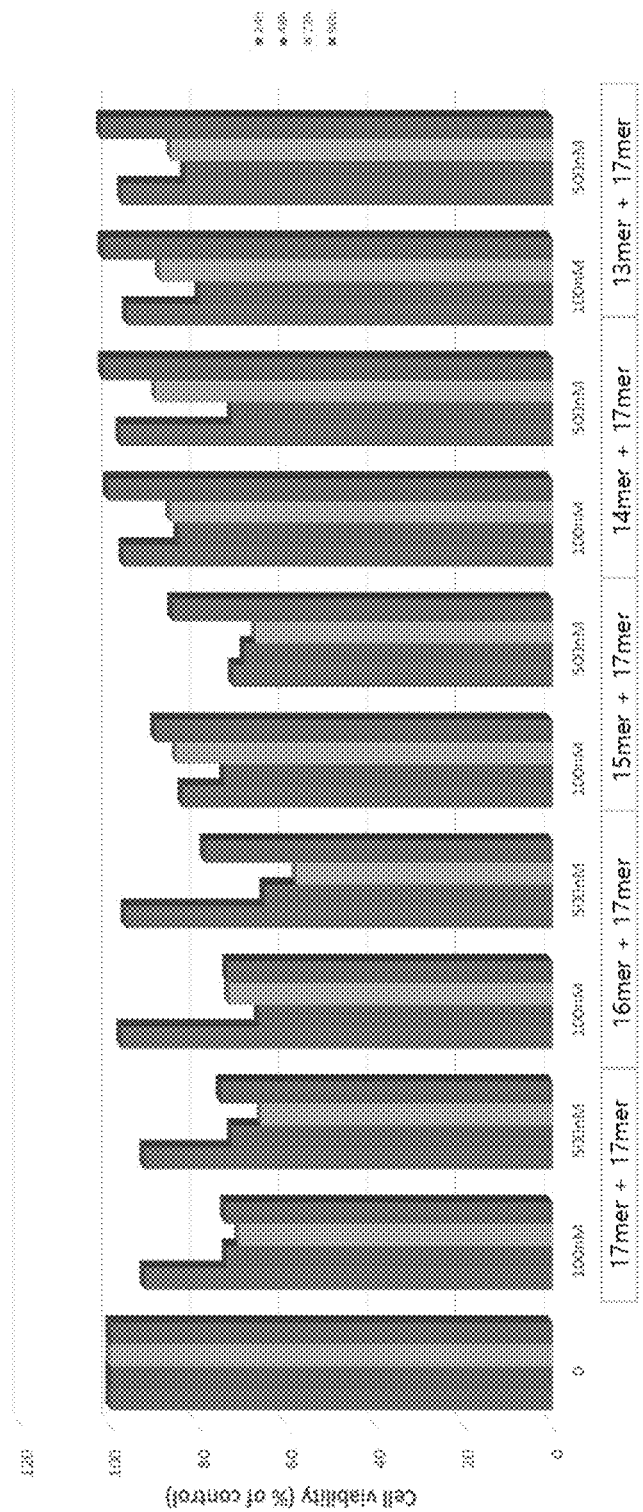
Figure 9B:
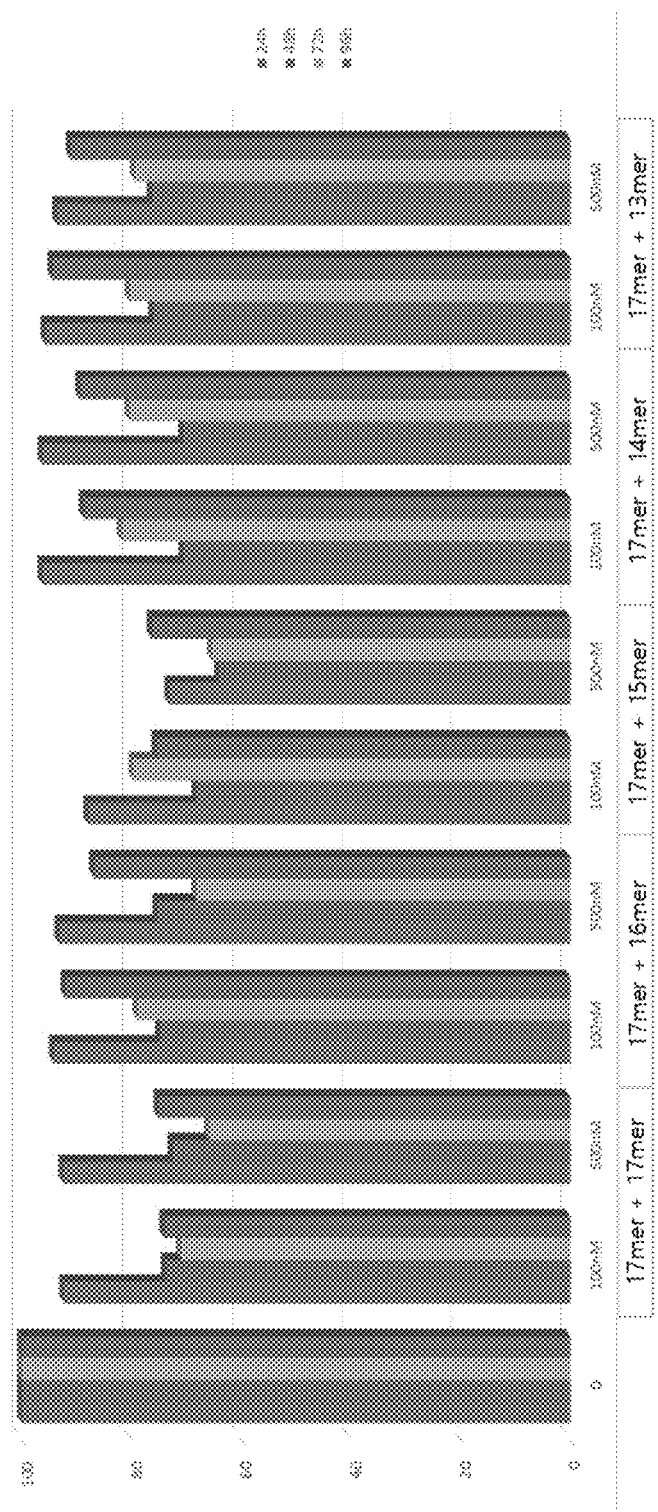

FIGS. 9a and 9b shows the change in cell viability with changes in the lengths of a bioactive peptide nucleic acid and a carrier peptide nucleic acid in the nucleic acid complex represented by structural formula (1).

(a): the change in cell viability with a change in the length of a carrier peptide nucleic acid; and
(b): the change in cell viability with a change in the length of a bioactive peptide nucleic acid.

Figure 10A:
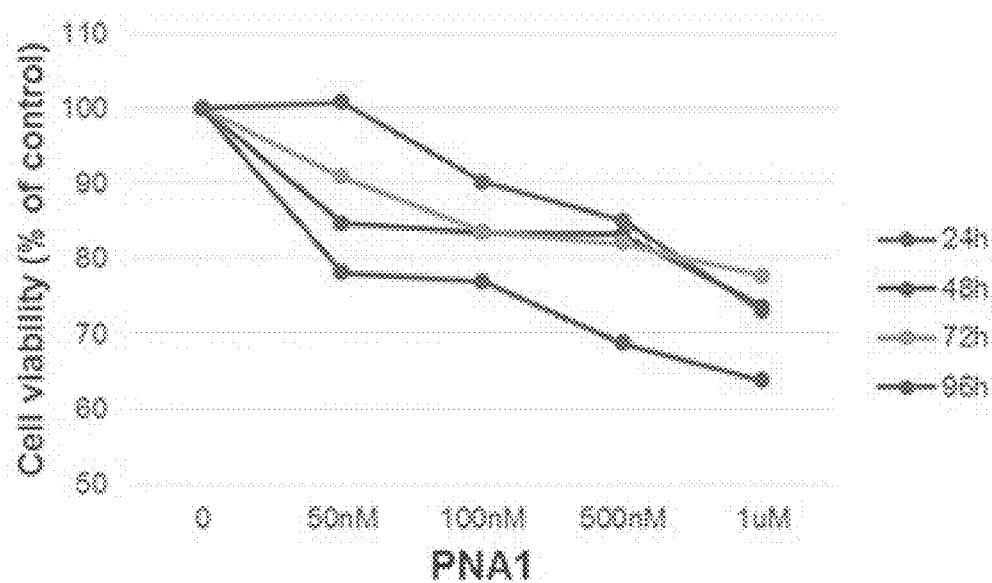
Figure 10A:
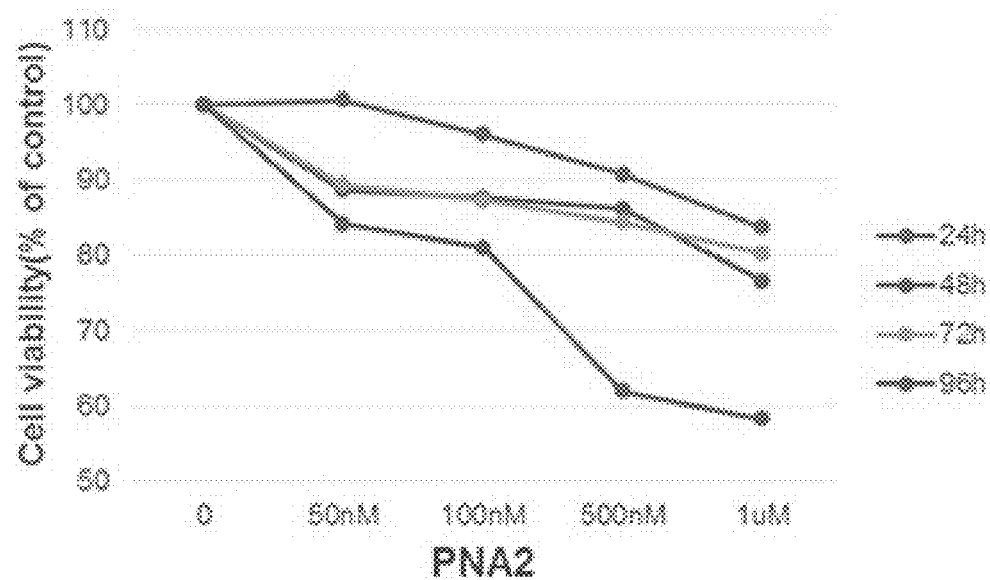
Figure 10B:
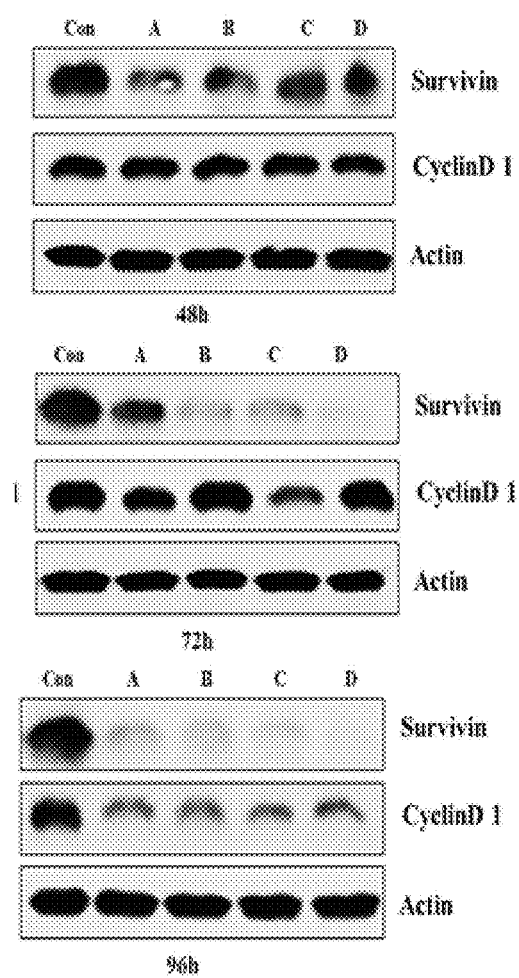
Figure 11A:
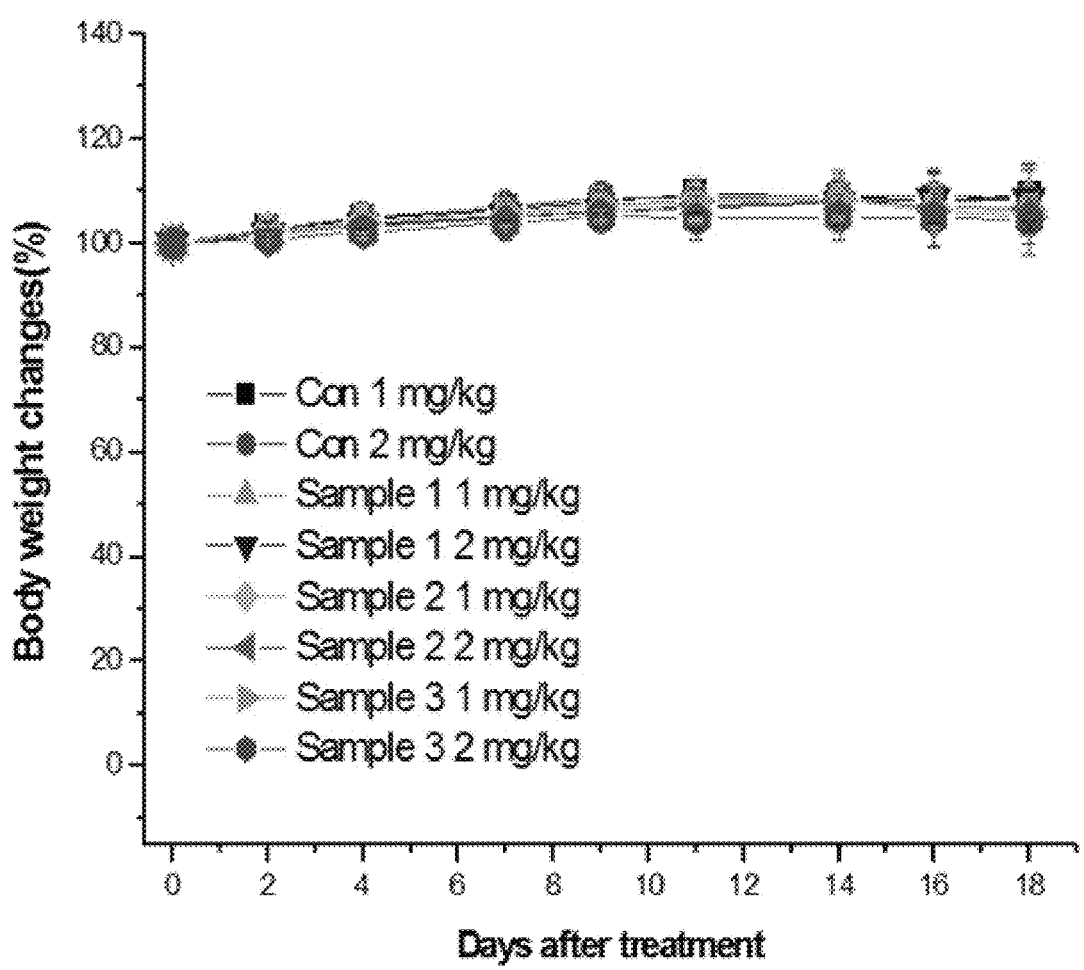
Figure 11B:
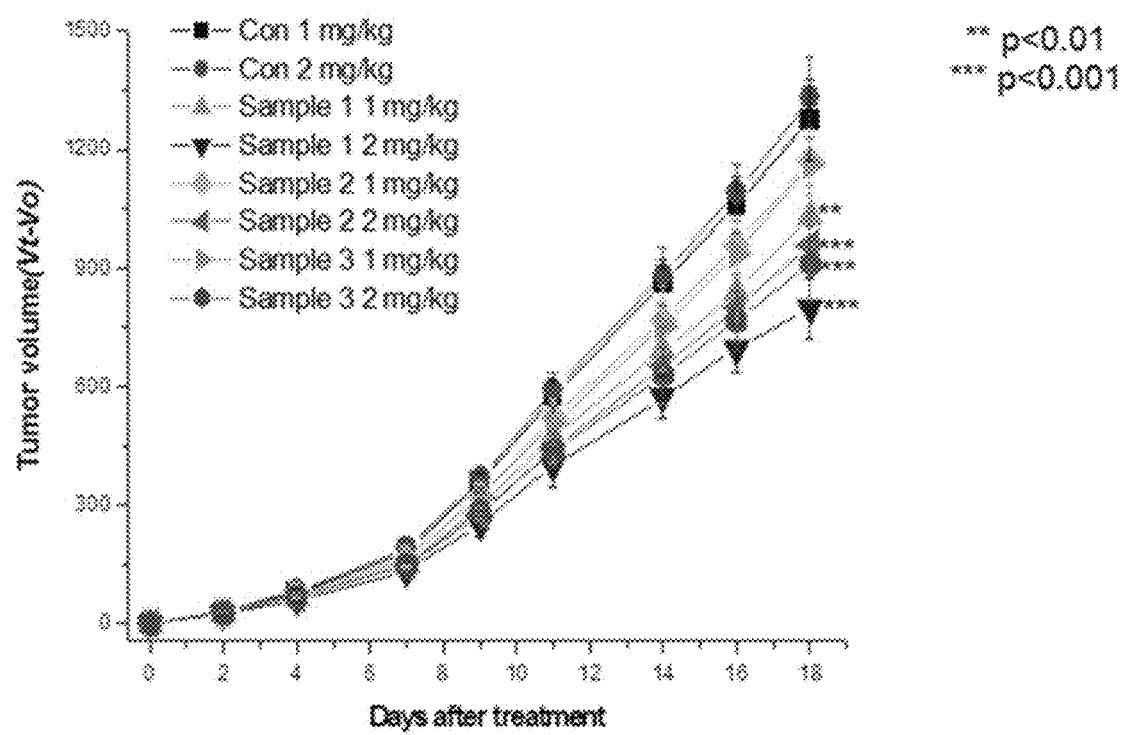
Figure 11C:
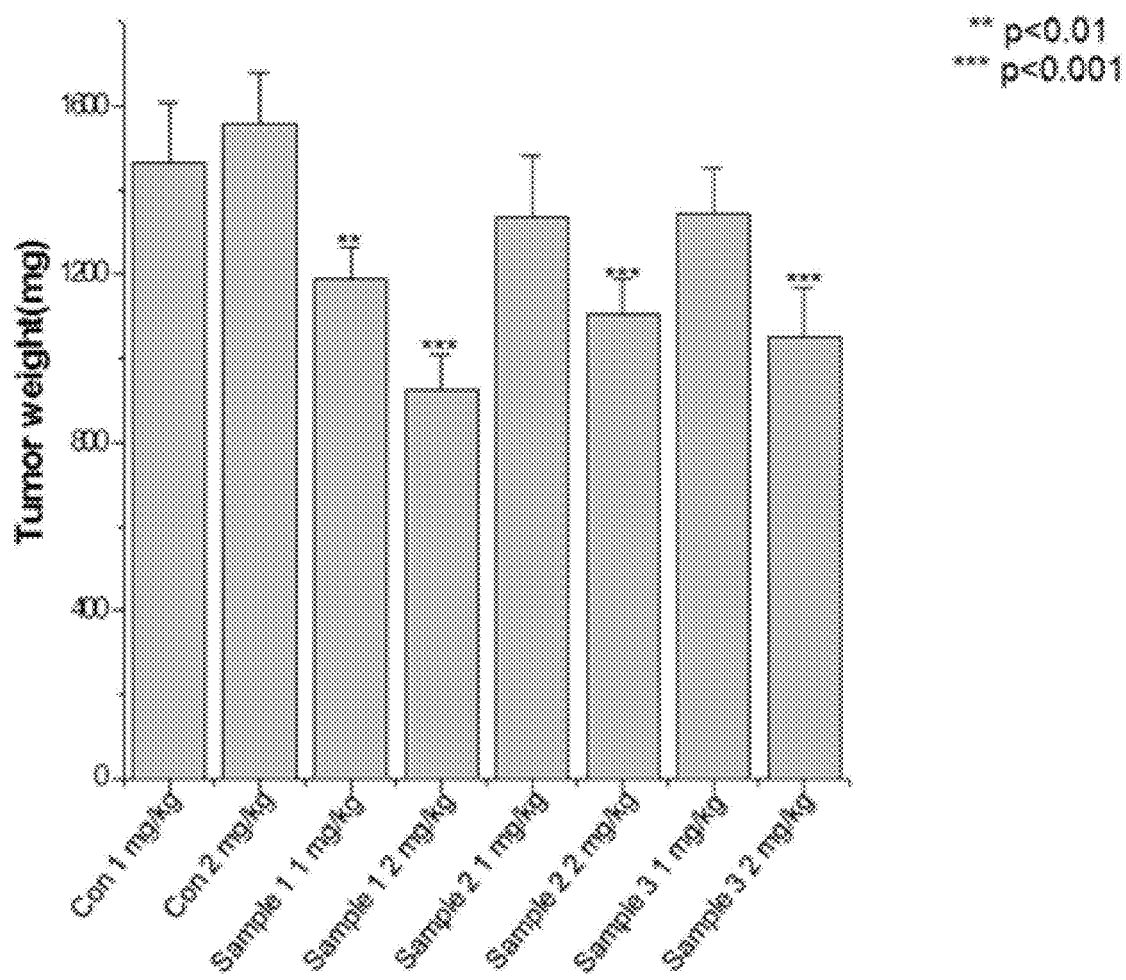
Figure 11D:
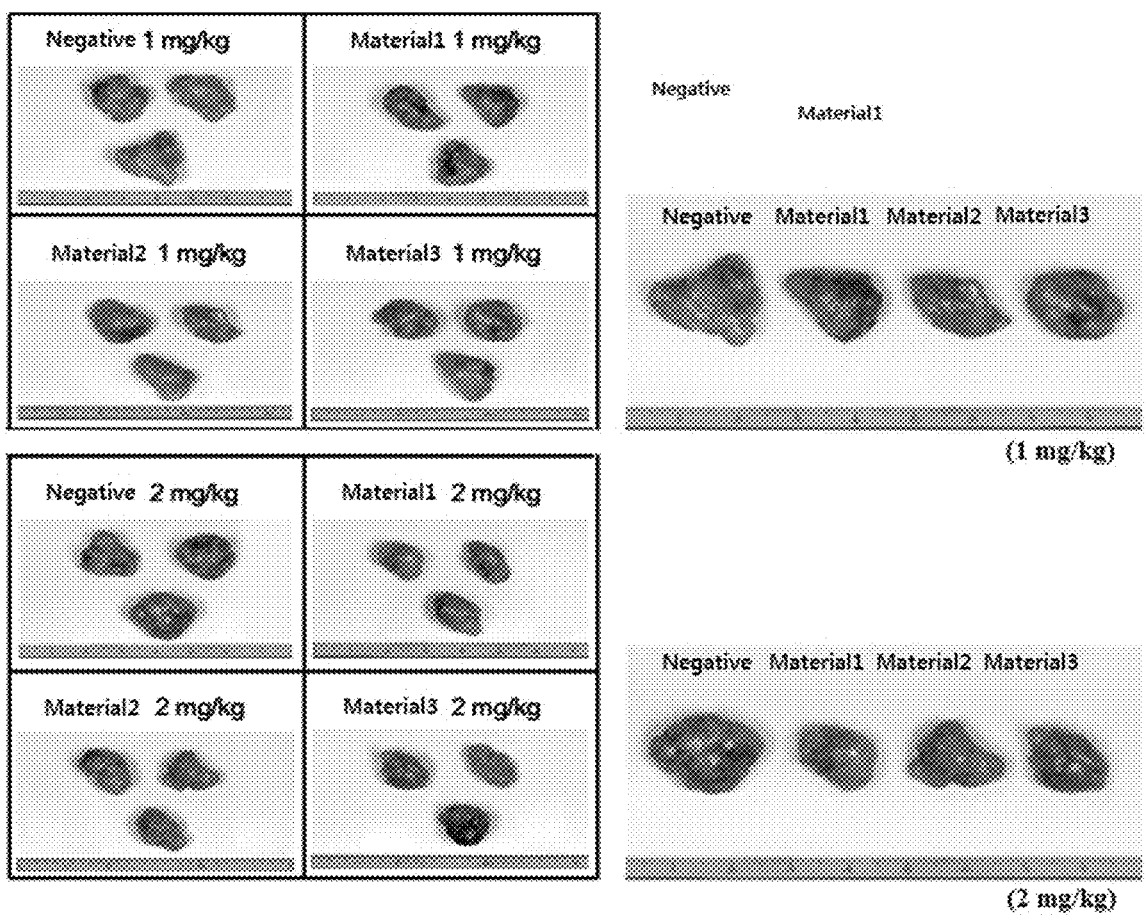
Figure 11E:
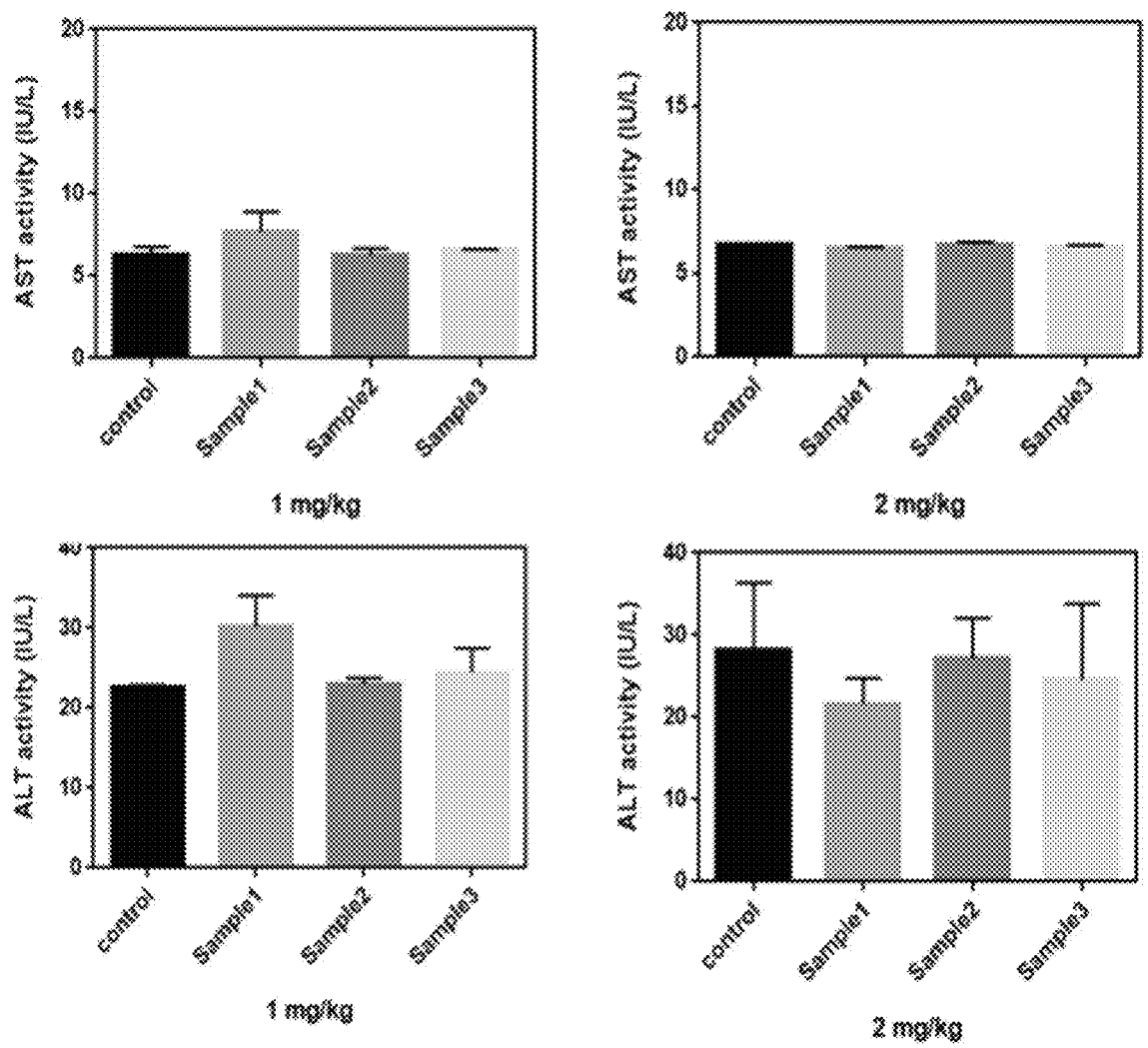

FIGS. 10a and 10b show the change in cell viability of a human colorectal cancer cell line by the nucleic acid complex represented by structural formula (1), which comprises a survivin-specific bioactive peptide nucleic acid, and show that expression of survivin and its downstream proteins in the cell line is inhibited by the nucleic acid complex.

(a): a change in cell viability; and
(b): a change in expression of survivin and its downstream proteins.

FIGS. 11a to 11e show the results of evaluating the tumor growth inhibitory effect of the nucleic acid complex represented by structural formula (1), which comprises a survivin-specific bioactive peptide nucleic acid, in mice transplanted with a human colorectal cancer cell line.

(a): changes in mouse body weight;
(b): changes in tumor volume;
(c): changes in tumor weight;
(d): changes in tumor appearance; and
(e): changes in hepatotoxicity marker.

Figure 12A:
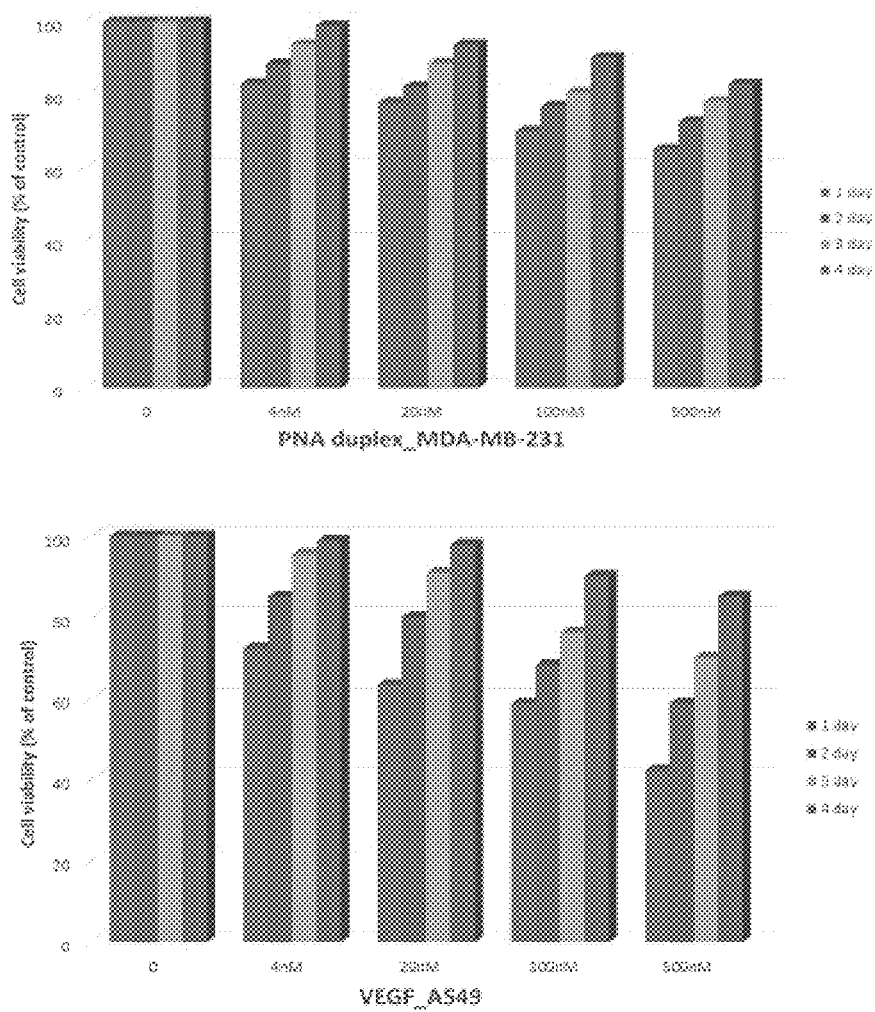
Figure 12B:
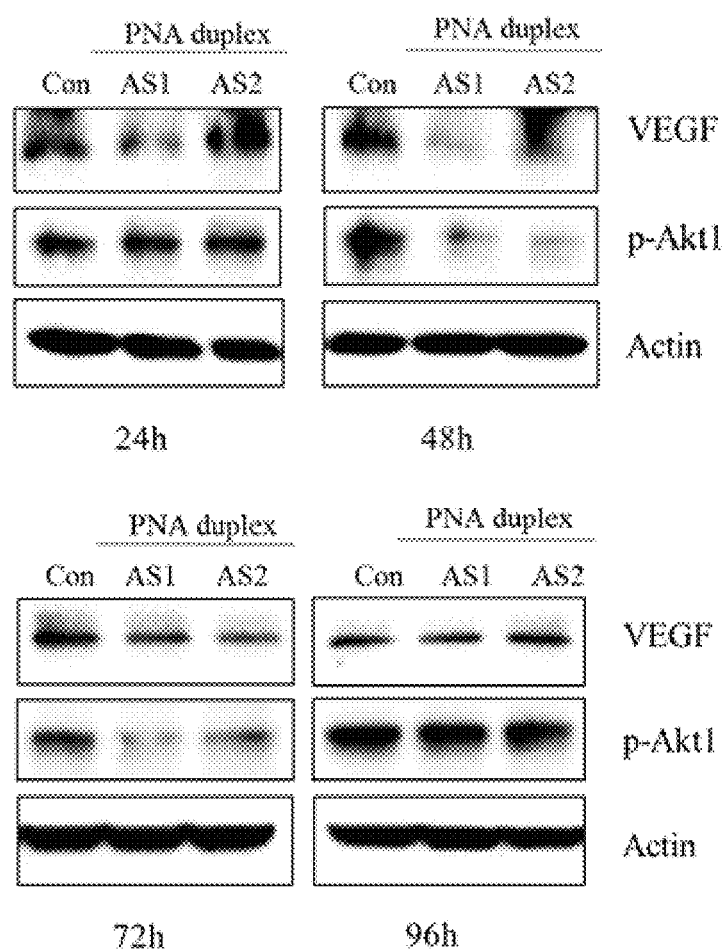
Figure 12C:
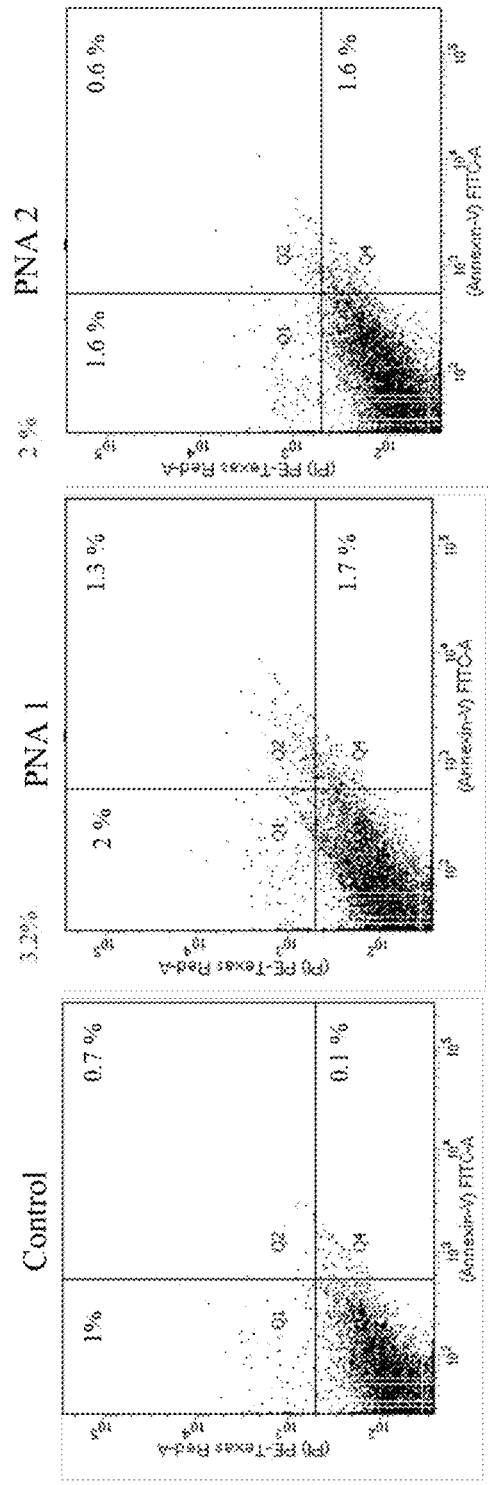

FIGS. 12a to 12c shows that the use of the nucleic acid complex represented by structural formula (1), which comprises a VEGF-specific bioactive peptide nucleic acid, changes the cell viability of a human breast cancer cell line and lung cancer cell line, inhibits expression of VEGF and its downstream proteins, and induces apoptosis.

(a): changes in cell viability;
(b): changes in expression of VEGF and its downstream proteins; and
(c): analysis of apoptosis induced by VEGF inhibition.

Figure 13:
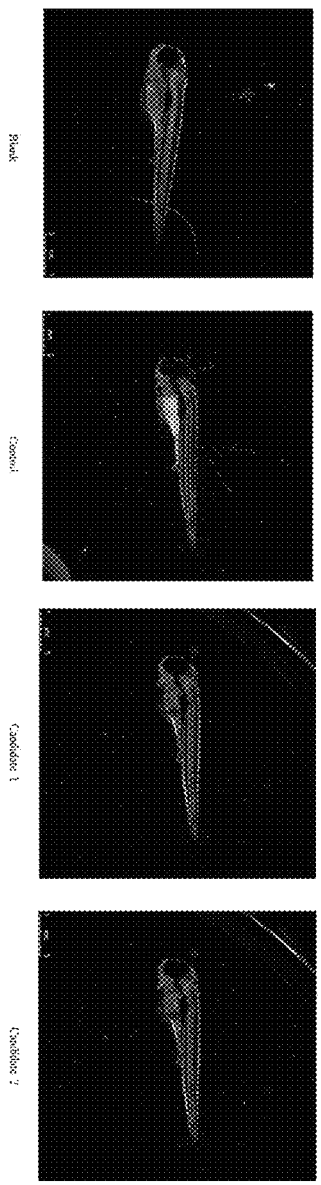

FIG. 13 shows the results of evaluating the anticancer pharmacological effect of the nucleic acid complex represented by structural formula (1), which comprises a VEGF-specific bioactive peptide nucleic acid, by use of zebra fishes as models.

Figure 14A:
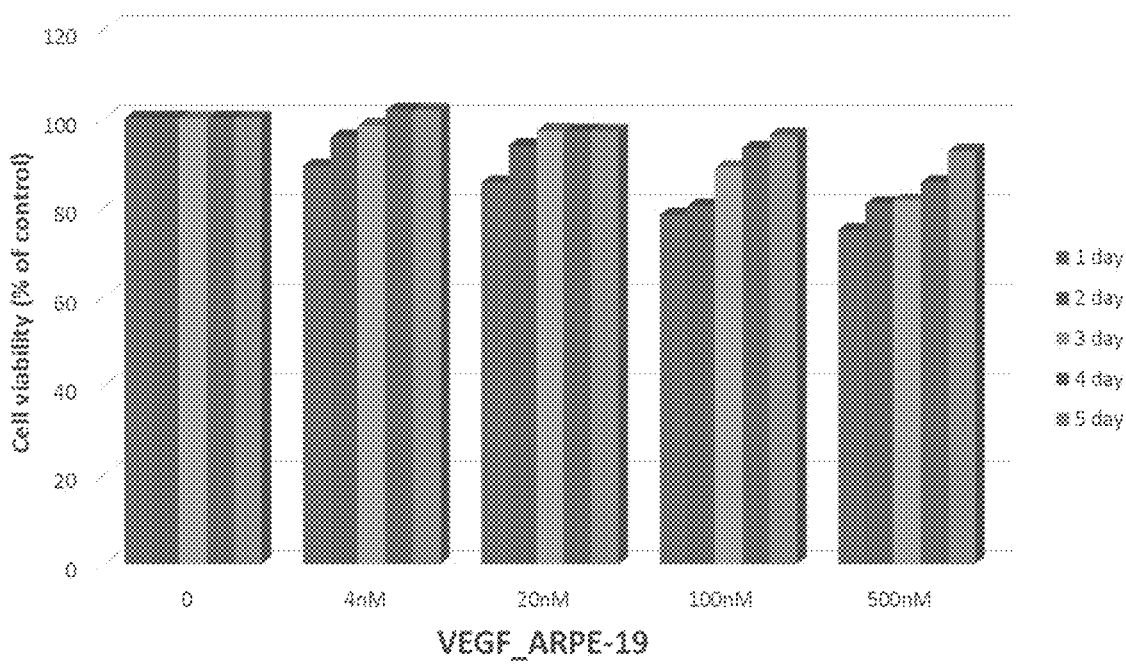
Figure 14B:
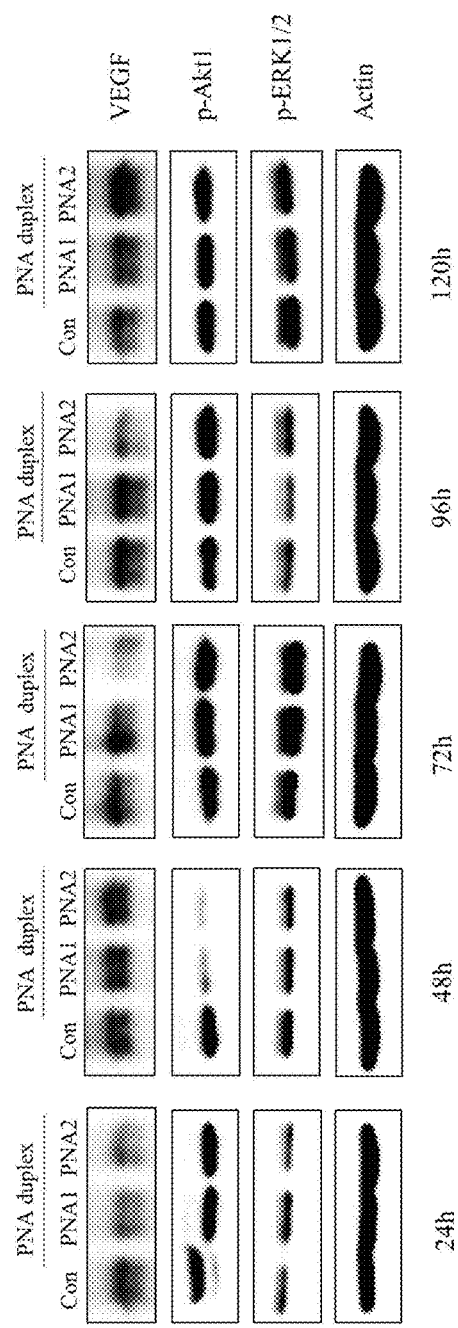

FIGS. 14a and 14b show that the use of the nucleic acid complex represented by structural formula (1), which comprises a VEGF-specific bioactive peptide nucleic acid, exhibits the effect of inhibiting the cell viability of human retinal pigment epithelium cells and inhibiting expression of VEGF and its downstream proteins in the cells.

(a): changes in cell viability; and
(b): changes in expression of VEGF and its downstream proteins.

Figure 15A:
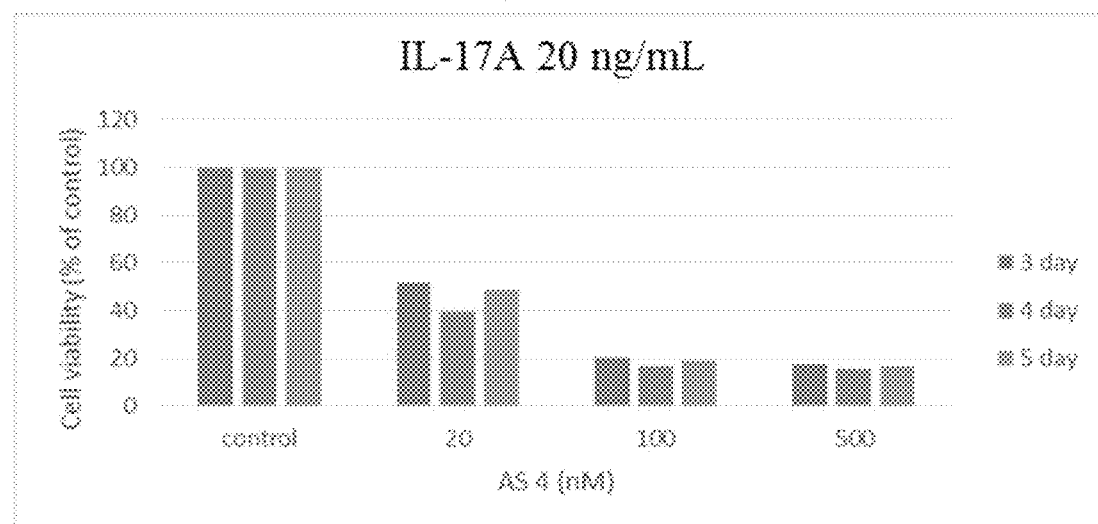
Figure 15B:
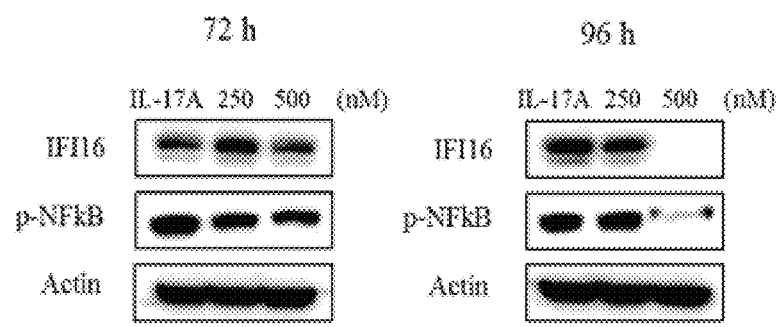
Figure 15B:
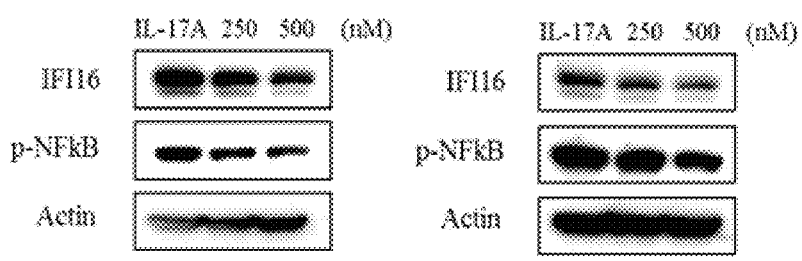

FIGS. 15a and 15b show that the use of the nucleic acid complex represented by structural formula (1), which comprises an IFI16-specific bioactive peptide nucleic acid, exhibits the effects of inhibiting the cell viability of human epidermal keratinocytes and inhibiting expression of IFI16 and its downstream proteins in the cells.

(a): changes in cell viability; and (b): changes in expression of IFI16 and its downstream proteins.

Figure 16A:
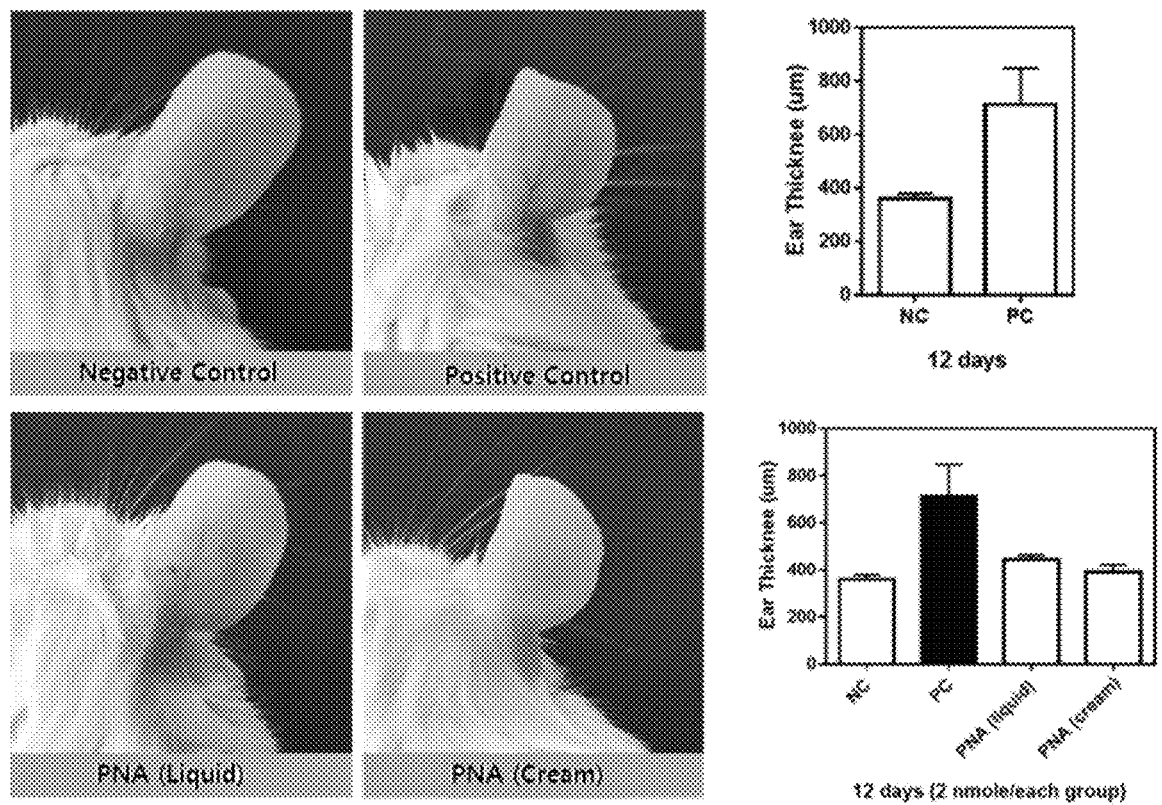
Figure 16B:
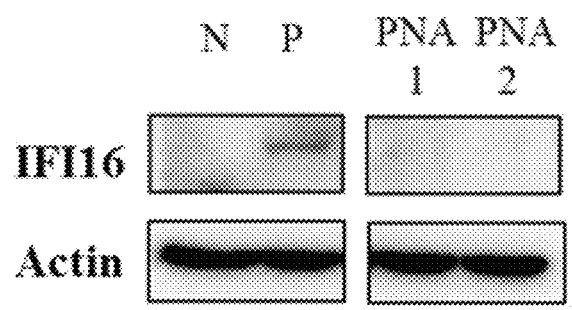
Figure 16C:
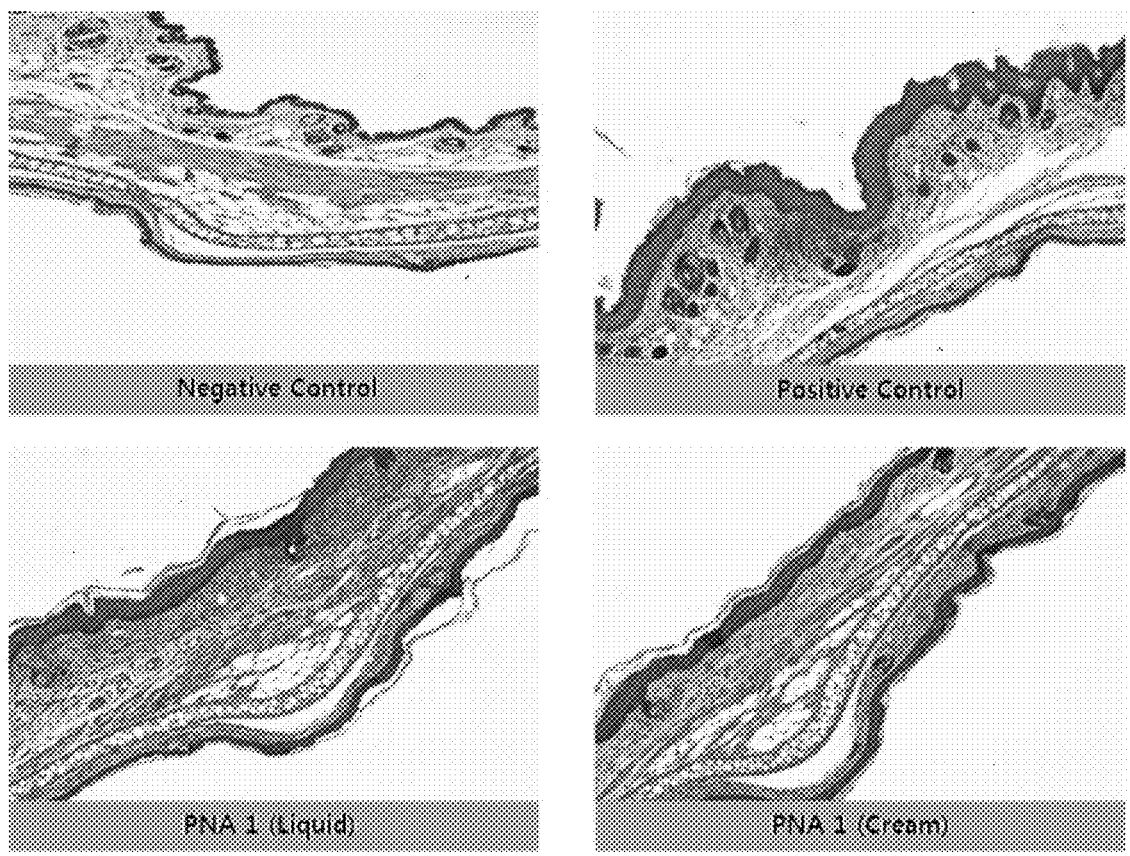

FIGS. 16a to 16c show the results of evaluating the effect of the nucleic acid complex represented by structural formula (1), which comprises an IFI16-specific bioactive peptide nucleic acid, on psoriasis-induced mouse models.

(a): photographs showing ear thickness changes and the results of measurement of ear thickness;

(b): changes in expression of IFI16 and its downstream proteins; and (c): biopsy results showing changes in epidermal keratinocytes in ear tissue.

Figure 17:
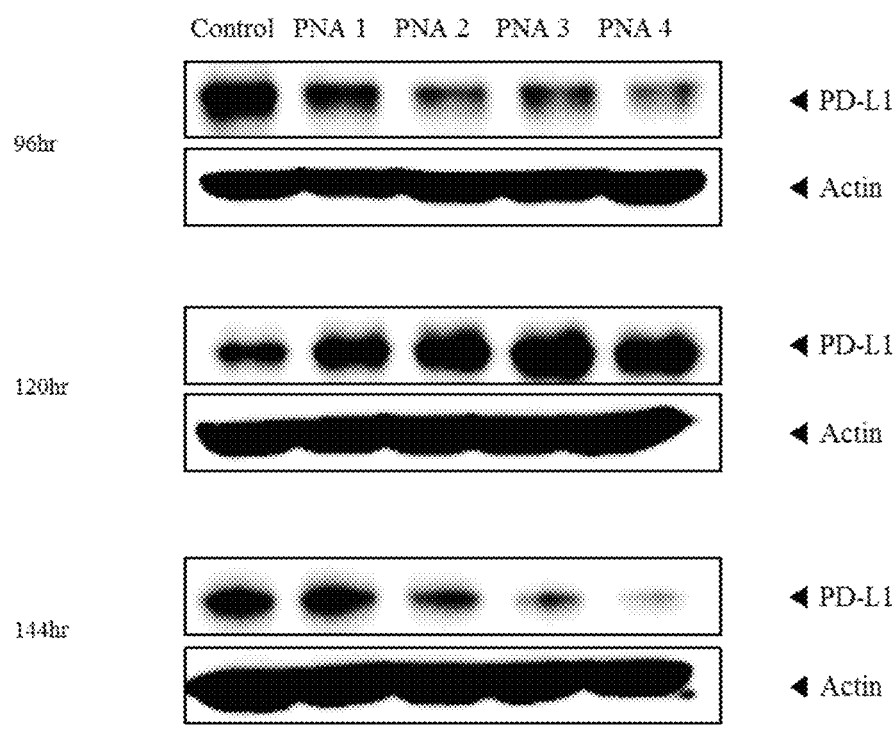

FIG. 17 shows the results of evaluating the effect of the nucleic acid complex represented by structural formula (1), which comprises a PD-L1-specific bioactive peptide nucleic acid, on the inhibition of PD-L1 and its downstream protein in a human breast cancer cell line.

Figure 18:
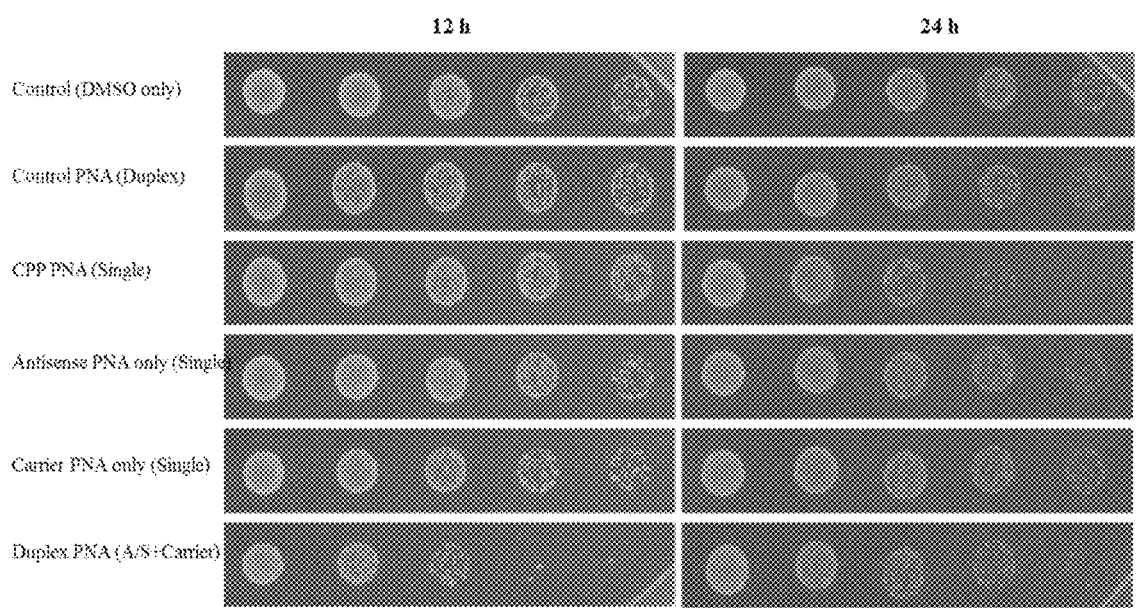

FIG. 18 shows the results of an experiment performed to examine whether the use of the nucleic acid complex represented by structural formula (1), which comprises an acpP-specific bioactive peptide nucleic acid, inhibits the growth of bacteria.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

Hereinafter, the present invention will be described in detail.

The present invention is directed to a nucleic acid complex having a structure represented by the following structural formula (1):

[A≡C$^{(+)}$],         [Structural formula (1)]

Wherein

A represents a bioactive nucleic acid having either a sequence capable of binding to a target gene or a target gene sequence;

C represents a carrier peptide nucleic acid capable of binding to the bioactive nucleic acid;

'≡' represents complementary binding between the bioactive nucleic acid and the carrier peptide nucleic acid;

the bioactive nucleic acid represented by A is generally negatively charged or neutral;

C$^{(+)}$ indicates that the carrier peptide nucleic acid is generally positively charged; and the carrier peptide nucleic acid comprises one or more peptide nucleic acid monomers modified such that the carrier peptide nucleic acid is generally positively charged.

As used herein, the term "bioactive nucleic acid" refers to a nucleic acid having a complementary sequence capable of binding to a target gene whose expression is to be reduced, particularly a complementary sequence capable of binding to the mRNA of this target gene, or comprising a sequence that promotes expression of a target gene to be expressed. Specifically, it refers to a nucleic acid which is involved in gene expression regulation, such as inhibiting or promoting expression of the gene of interest. It may be a nucleic acid having a sequence complementary to a target gene whose expression is to be decreased or increased, or may be a nucleic acid having a sequence complementary of the sequence of a single-stranded RNA, such as pre-mRNA, miRNA, mRNA, or the like.

In particular, the "bioactive nucleic acid" in the present invention may bind to a target gene or a nucleotide sequence comprising the same in vitro or in vivo, thereby activating or inhibiting the characteristic function of the target gene (e.g., transcript expression or protein expression) or regulating splicing of pre-mRNA (e.g., exon skipping), wherein the nucleotide sequence may be a gene regulatory sequence, or a gene coding sequence, or a splicing regulatory sequence. The gene regulatory sequence may be selected from among a promoter, a transcriptional enhancer, a 5' untranslated region, a 3' untranslated region, a viral packaging sequence, and a selection marker. The gene coding sequence may be an exon or an intron, and the gene coding sequence may be located within 10, 5, 3 or 1 kb or 500, 300 or 200 bp from the transcription initiation site of the gene. For example, it may be located upstream or downstream of the initiation site. Furthermore, the splicing regulatory sequence may comprise a sequence associated with exon skipping, cryptic splicing, pseudo-splice site activation, intron retention, or alternative splicing deregulation.

As used herein, the term "carrier peptide nucleic acid" refers to a nucleic acid whose bases partially or completely bind complementarily to the bioactive nucleic acid, thereby imparting functionality. Carrier peptide nucleic acids that may be used in the present invention include not only a peptide nucleic acid (PNA), but also modified nucleic acids similar thereto. The carrier peptide nucleic acid is preferably a peptide nucleic acid, but is not limited thereto.

In the present invention, each of the bioactive nucleic acid and the carrier peptide nucleic acid may comprise 2 to 50, preferably 5 to 30, more preferably 10 to 25, most preferably 15 to 17 nucleic acid monomers.

Moreover, the bioactive nucleic acid may be composed of natural nucleic acid bases and/or modified nucleic acid monomers, and the carrier peptide nucleic acid may have a nucleotide sequence which is partially or completely complementary to the bioactive nucleic acid.

In particular, the carrier peptide nucleic acid may comprise one or more universal bases, and the carrier peptide nucleic acid may also be completely composed of universal bases.

In the present invention, the bioactive nucleic acid may be selected from the group consisting of DNA, RNA, and modified nucleic acids, i.e., PNA (peptide nucleic acid), PMO (phosphorodiamidate morpholino oligonucleotide), LNA (locked nucleic acid), GNA (glycol nucleic acid), TNA (threose nucleic acid), antisense oligonucleotide, aptamer, siRNA (small interfering RNA), shRNA (short hairpin RNA), ribozyme, and DNAzyme. Preferably, bioactive nucleic acid may be selected from the group consisting of DNA, RNA, and modified nucleic acids, i.e., PNA (peptide nucleic acid), PMO (phosphorodiamidate morpholino oligonucleotide), LNA (locked nucleic acid), GNA (glycol nucleic acid), and TNA (threose nucleic acid).

In the present invention, if a monomer used in the bioactive nucleic acid is PNA, then the bioactive nucleic acid is called bioactive peptide nucleic acid, and if other monomer is used, then the bioactive nucleic acid is called in the same manner.

In the present invention, the bioactive nucleic acid and the carrier peptide nucleic acid may further comprise one or more functional groups selected from the group consisting of phosphodiester, 2'0-methyl, 2' methoxy-ethyl, phosphoramidate, methylphosphonate), and phosphorothioate.

In the present invention, each of the bioactive nucleic acid and the carrier peptide nucleic acid of the nucleic acid complex may be generally positively charged (cationic), negatively charged (anionic) or neutral in the electrical property.

The term "generally" as used when expressing the electrical property does not mean the electrical property of individual bases, but means the overall electrical properties of the bioactive nucleic acid or the carrier peptide nucleic acid when viewed externally.

For example, if the number of negatively charged monomers in the bioactive nucleic acid is larger even though some monomers in the bioactive nucleic acid are positively charged, then the bioactive nucleic acid is negative charged when "generally" viewing the electrical property.

If the number of positively charged bases and/or backbones in the carrier peptide nucleic acid is larger even though some bases and/or backbones in the carrier peptide nucleic acid are negatively charged, then the carrier peptide nucleic acid is positively charged when "generally" viewing the electrical property.

In this regard, in the nucleic acid complex represented by structural formula (1) according to the present invention, it is preferred that the bioactive nucleic acid be negatively charged or neutral when generally viewing the electrical property, and the carrier peptide nucleic acid be positively charged when generally viewing the electrical property.

The electrical property of each of the bioactive nucleic acid and the carrier peptide nucleic acid may be imparted using a modified peptide nucleic acid monomer. The modified peptide nucleic acid monomer may comprise one or more positively charged amino acids selected from the group consisting of lysine (Lys, K), arginine (Arg, R), histidine (His, H), diamino butyric acid (DAB), ornithine (Orn), and an amino acid analogue, as positively charged carrier peptide nucleic acids. In addition, the modified peptide nucleic acid monomer may comprise one or more negatively charged amino acids selected from the group consisting of glutamic acid (Glu, E) that is a negatively charged amino acid, and an amino acid analogue, as negatively charged carrier peptide nucleic acids.

Preferably, the carrier peptide nucleic acid may comprise one or more gamma- or alpha-backbone-modified peptide nucleic acid monomers so as to be generally positively charged. In particular, the gamma- or alpha-backbone-modified peptide nucleic acid monomers may comprise one or more positively charged amino acids selected from the group consisting of lysine (Lys, K), arginine (Arg, R), histidine (His, H), diamino butyric acid (DAB), ornithine (Orn), and an amino acid analogue in its backbone so as to be electrically positive.

The modification of the peptide nucleic acid monomers for imparting charges may be performed using nucleobase-modified peptide nucleic acid monomers besides the backbone modification.

Preferably, the carrier peptide nucleic acid may comprise an amine, triazole or imidazole moiety in its nucleobase so as to be electrically positive, or may comprise carboxylic acid in its nucleobase so as to be electrically negative.

In addition, the modified nucleic acid monomers of the carrier peptide nucleic acid may further comprise negative charges in the backbone or nucleobase, but the modified peptide nucleic acid monomers preferably comprises a larger number of positively charged monomers than negatively charged monomers such that the carrier peptide nucleic acid is generally positively charged.

Preferably, the nucleic acid complex represented by structural formula (1) according to the present invention may be generally positively charged.

In the nucleic acid complex represented by structural formula (1) according to the present invention, one or more substances selected from the group consisting of a hydrophobic moiety, a hydrophilic moiety, a target antigen-specific antibody, an aptamer, a quencher, and a fluorescent/luminescent marker may be bound to the bioactive nucleic acid and/or the carrier peptide nucleic acid. Preferably, one or more substances selected from the group consisting of the hydrophobic moiety, the hydrophilic moiety, the target antigen-specific antibody, the aptamer, and the fluorescent/luminescent marker for imaging may be bound to the carrier peptide nucleic acid.

In the present invention, the binding of one or more substances selected from the group consisting of the hydrophobic moiety, the hydrophilic moiety, the target antigen-specific antibody, the aptamer, the quencher, the fluorescent marker, and the luminescent marker to the bioactive nucleic acid and/or the carrier peptide nucleic acid may be performed by a single covalent bond or a linker-mediated covalent bond, but is not limited thereto (see table 1). Preferably, cell permeation, solubility, stability, delivery and imaging-related substances (e.g., hydrophobic moiety, etc.) bound to the nucleic acid carrier is present independently of the bioactive nucleic acid that regulates expression of a target gene.

In the present invention, complementary binding of the nucleic acid may largely be classified into antiparallel binding and parallel binding. Complementary binding of the nucleic acid is configured such that it is released in the presence of a sequence targeted by the bioactive nucleic acid (a sequence complementary to the bioactive nucleic acid).

Antiparallel binding and parallel binding is determined according to 5'-directionality and 3'-directionality in DNA-DNA or DNA-PNA binding. Antiparallel binding is a general DNA-DNA or DNA-PNA binding method. Taking the nucleic acid complex of structural formula (1) according to the present invention as an example, antiparallel binding means that the bioactive nucleic acid in the 5' to 3' direction and the carrier peptide nucleic acid in the 3' to 5' direction are bound to each other, and parallel binding shows a somewhat lower binding affinity than antiparallel binding, and means that the bioactive nucleic acid and the carrier peptide nucleic acid are bound to each other in the 5' to 3' direction or the 3' to 5' direction.

Preferably, in the nucleic acid complex represented by structural formula (1) according to the present invention, the binding affinity (melting temperature (Tm)) between the bioactive nucleic acid and the carrier peptide nucleic acid may be lower than the binding affinity between the bioactive nucleic acid and a gene targeted by the bioactive nucleic acid, particularly the mRNA of the target gene.

As a specific example for allowing the binding affinity (melting temperature (Tm)) between the bioactive nucleic acid and the carrier peptide nucleic acid to be lower than the binding affinity between the bioactive nucleic acid and a gene targeted by the bioactive nucleic acid, particularly the mRNA of the target gene, the bioactive nucleic acid and the carrier peptide nucleic acid may be bound to each other by parallel binding or partial specific binding so that the binding affinity (melting temperature (Tm)) between the bioactive nucleic acid and the carrier peptide nucleic acid is lower than the binding affinity between the bioactive nucleic acid and a gene targeted by the bioactive nucleic acid, particularly the mRNA of the target gene, but is not limited thereto.

As another example, the carrier peptide nucleic acid may have a linker, a universal base, and at least one peptide nucleobase selected from peptide nucleobases which are not complementary to the corresponding bases of the bioactive nucleic acid so that the binding affinity (melting temperature (Tm)) between the bioactive nucleic acid and the carrier peptide nucleic acid is lower than the binding affinity between the bioactive nucleic acid and a gene targeted by the bioactive nucleic acid, particularly the mRNA of the target gene (see table 1), The universal base that can be used in the present invention may be one or more selected from the group consisting of natural bases, including adenine, guanine, cytosine, thymine, and uracil, and inosine PNA, indole PNA, nitroindole PNA, and abasic, which are bases that bind without selectivity and have lower binding affinity than complementary binding affinity. Preferably, inosine PNA may be used as the universal base.

The present invention provides a combination of binding form and electrical property of nucleic acids for regulating the function of the nucleic acid complex, can control the particle size and the time of action through the combination of binding form and electrical property of nucleic acids, and can increase cell permeability, solubility and specificity.

In particular, the particle size of the nucleic acid complex can be controlled by controlling the charges of the bioactive peptide nucleic acid and the carrier peptide nucleic acid, and the particle size of the nucleic acid complex can be decreased through a proper charge balance between a suitable number of positive charges of the carrier peptide nucleic acid and charges of the bioactive peptide nucleic acid.

Meanwhile, the time point at which the bioactive peptide nucleic acid binds to a target sequence in the presence of a target gene (the time of strand displacement of the bioactive nucleic acid to the target sequence, and the time of target specific release and binding of the bioactive nucleic acid) can be controlled by controlling the binding affinity between the carrier peptide nucleic acid and the bioactive peptide nucleic acid.

TABLE 1

Examples of binding between bioactive nucleic acid and carrier peptide nucleic acid

| Type | | Complex structure | Features |
|---|---|---|---|
| I | Carrier peptide nucleic acid | 5'-[NNNNN*NNNNNNNNN*NNNNN]-3' | Partial match 1 (Substitution) |
| | Bioactive nucleic acid | 3'-[NNNNNNNNNNNNNNNNNNNNN]-5' | |
| II | Carrier peptide nucleic acid | 5'-[NNNNNNNNNNNNNNNNNNNN]-3' | Partial match 2 (Insertion/Deletion) |
| | Bioactive nucleic acid | 3'-[NNNNNNNNNNNNNNNNNNNNN]-5' | |
| III | Carrier peptide nucleic acid | 5'-[NNNNNNNN$$$NN$NNNNNNN]-3' | Universal base |
| | Bioactive nucleic acid | 3'-[NNNNNNNNNNNNNNNNNNNNN]-5' | |
| IV | Carrier peptide nucleic acid | 5'-[NNNNNNNNNN=NNNNNNNNN]-3' | Linker |
| | Bioactive nucleic acid | 3'-[NNNNNNNNNNNNNNNNNNNNN]-5' | |
| V | Carrier peptide nucleic acid | 5-[NNNNNNNNNNNNNNNNNNNNN]-3' | Parallel binding |
| | Bioactive nucleic acid | 5'-[NNNNNNNNNNNNNNNNNNNNN]-3' | |

In Table 1 above, N represents nucleobases (ATGC); * represents a sequence which is not complementary to an antisense nucleic acid sequence; $ represents an universal base; =represents a linker; and 5'- and 3'- represent the directionalities of nucleic acid (bases).

In other words, in the nucleic acid complex of structural formula (1) according to the present invention, the time of strand displacement of the bioactive nucleic acid to a target gene and the target specific release and binding of the bioactive nucleic acid may be controlled by the non-specific bases of the carrier peptide nucleic acid for non-specific binding of the complex, universal bases, the presence or absence of a linker, and the number and position of the bases, and may also be controlled by a combination of these conditions with parallel or antiparallel binding which is complementary binding in the complex.

The nucleic acid complex represented by structural formula (1) according to the present invention may be prepared by hybridizing the bioactive nucleic acid and the carrier peptide nucleic acid under proper conditions.

As used herein, the term "hybridization" means that complementary single-stranded nucleic acids form a double-stranded nucleic acid. Hybridization can occur when the complementarity between two nucleic acid strands is perfect match or when some mismatched residues exist. The degree of complementarity necessary for hybridization may vary depending on hybridization conditions, particularly may be controlled by binding temperature.

The bioactive nucleic acid and the carrier peptide nucleic acid according to the present invention may have a reporter and a fluorescence quencher attached to both ends. The fluorescence quencher can quench the fluorescence of the reporter. The reporter may be one or more selected from the group consisting of FAM (6-carboxyfluorescein), Texas red, HEX (2', 4', 5', 7'-tetrachloro-6-carboxy-4,7-dichlorofluorescein), and Cy5. The quencher may be one or more selected from the group consisting of TAMRA (6-carboxytetramethyl-rhodamine), BHQ1, BHQ2 and Dabcyl, but is not limited thereto.

In the present invention, the carrier peptide nucleic acid can form a complementary hydrogen bond with the bioactive nucleic acid and deliver the bioactive nucleic acid into cells, and the bioactive nucleic acid can bind to a target gene and regulate expression of the target gene.

As used herein, the term 'target gene' refers to a nucleic acid sequence (nucleotide sequence) to be activated, inhibited or labeled, and is not different from and is used interchangeably with the term 'target nucleic acid'.

If the target nucleic acid (nucleotide sequence) comprising the target gene contacts (binds) the complex in vitro or in vivo, then the bioactive nucleic acid is separated from the carrier peptide nucleic acid and exhibits biological activity.

In another aspect, the present invention is directed to a composition for regulating expression of a target gene, a composition for preventing or treating diseases, and a composition for diagnosing disease, which comprise the nucleic acid complex represented by structural formula (1).

The present invention is also directed to a method for preventing or treating disease, which comprises administering the nucleic acid complex represented by structural formula (1) to a patent in need of treatment of prevention.

The present invention is also directed to a method of regulating expression of a target gene, which comprises using the nucleic acid complex represented by structural formula (1).

The diseases that can be prevented, treated, or diagnosed using the nucleic acid complex represented by structural formula (1) may be determined depending on a target gene to which the bioactive nucleic acid in the nucleic acid complex represented by structural formula (1) binds. Preferably, the diseases are cancers or tumors, but are not limited thereto.

The term "composition for treatment" may be used interchangeably with a pharmaceutical composition", and the composition comprises, as an active ingredient, a nucleic acid complex comprising a bioactive nucleic acid and a carrier bioactive nucleic acid bound thereto.

The composition for treatment according to the present invention may be formulated in an oral or parenteral dosage form according to standard pharmaceutical practices. This formulation may contain an additive such as a pharmaceutically acceptable carrier, an excipient, a supplement, or a diluent besides the active ingredient.

The term "physiologically acceptable" means the property that does not impair the biological activity and physical properties of a compound.

The term "carrier" is defined as a compound which facilitates the addition of the complex into cells or tissues. For example, dimethylsulfoxide (DMSO) is a carrier which is commonly used to facilitate the penetration of a number of organic compounds into the cells or tissues of organisms.

The term "diluent" is defined as a compound that not only stabilizes the biologically active form of the target compound, but also a compound that is diluted in water in which it was dissolved. Salts dissolved in buffer solution are used as diluents in the related art. A commonly used buffer solution is phosphate buffered saline solution because it mimics the condition of salts in human solution. Since the buffer salts can control the pH of solution at low concentration, biological activity of compounds are rarely altered by buffer diluents.

The compounds containing the complex used herein can be administered to a human patient per se, or in pharmaceutical compositions where they are mixed with other active ingredients, as in combination therapy, or suitable carriers or excipients.

Pharmaceutical compositions suitable for use in the present invention include compositions where the active ingredients are contained in an amount effective to achieve its intended purpose. More specifically, a therapeutically effective amount means an amount of a compound effective to prevent, stabilize, alleviate or ameliorate symptoms of disease, or prolong the survival of the subject being treated. Determination of a therapeutically effective amount is well within the capability of those skilled in the art, especially in light of the detailed disclosure provided herein.

As used herein, the term "preventing" or "treatment" refers to all actions that exhibit anticancer activity and inhibit the growth of cancer or delay the development of cancer by administering (or applying) a pharmaceutical composition comprising the complex or a pharmaceutically acceptable salt thereof. As used herein, the term "treating" or "treatment" refers to all actions that alleviate or perfectly cure cancer by administering (or applying) a pharmaceutical composition comprising the complex or a pharmaceutically acceptable salt thereof.

The diseases that can be prevented or treated by a composition comprising the nucleic acid complex of the present invention are not particularly limited. Examples of the diseases may preferably include, but are not limited to, tumors or cancers, inflammatory diseases, age-related macular degeneration, deafness, and skin diseases.

Diseases that can be treated by a composition for treatment comprising the nucleic acid complex of the present invention are determined by a target gene to which the bioactive nucleic acid contained in the nucleic acid complex binds. Examples of a target gene for cancer therapy, to which the bioactive nucleic acid contained in the nucleic acid complex binds, include Survivin, VEGF, Androgen receptor, KRAS, Clusterin, TGFßR2, ERBB3, Transglutaminase 2, ABCB1, Hsp27, STAT3, PD-L1, and the like.

A gene that targets inflammatory diseases is DE4B or Pellino-1, a gene that targets rare diseases and severe diseases is SMN2, ApoB-100, ICAM-1, ApoCIII, TTR, HTT, GHr, SOD1, ANGPTL3, PKK, miR-21, TMPRSS6, FMR1, or Connexin 26, a gene that targets cardiovascular diseases is Factor XI, Apo(a), or ApoCIII, AG, a gene that targets metabolic diseases is GCGR, ANGPTL3, miR-103/107, or DGAT2, and a gene that targets skin diseases is IFI16, TLR6, or TIEG1, but examples of the genes are not limited thereto.

The composition for treatment according to the present invention may be formulated alone or together with a suitable pharmaceutically acceptable carrier or excipient as described below, into a parenteral or oral dosage form by a known method. Specific examples of such a formulation include oral formulations such as an injectable formulation, a soft capsule formulation, a hard capsule formulation, a tablet formulation, and a syrup formulation, or agents for external applications.

Preferably, the composition for treatment comprising the nucleic acid complex according to the present invention may be prepared and used in a parenteral dosage form. Examples of suitable parenteral dosage forms include, but are not limited to, solution or freeze-dried formulations suitable for subcutaneous injection, intravenous injection, intramuscular injection or intra-thoracic injection.

In still another aspect, the nucleic acid complex according to the present invention may be administered via skin delivery route. The formulation for skin delivery may be selected from the group consisting of aqueous solution, cream, and ointment, but is not limited thereto, and all types of formulations for skin delivery, which are known in the related art, can be used.

In order to formulate the composition for treatment according to the present invention in a parenteral dosage form, the composition comprises the nucleic acid complex of the present invention, and may be one selected from among physiological saline, sterile water, Ringer's solution, buffered saline, dextrose solution, maltodextrin solution, glycerol, ethanol, and a mixture of two or more thereof. If necessary, the composition may contain other conventional additives such as an antioxidant, a buffer, and a bacteriostatic agent. In addition, a diluent, a dispersing agent, a surfactant, a binder and a lubricant may additionally be added to the composition to be prepared into an injectable formulation such as an aqueous solution, a suspension or an emulsion. Particularly, the composition is preferably provided as a lyophilized formulation. For the preparation of a lyophilized formulation, a conventional method known in the technical field to which the present invention pertains may be used, and a stabilizer for lyophilization may also be added. Furthermore, the composition can preferably be formulated according to diseases or components by a suitable method known in the art or by a method disclosed in Remington's Pharmaceutical Science, Mack Publishing Company, Easton Pa.

In addition, the composition for treatment according to the present invention may be formulated in oral dosage forms, including powder, tablet, capsule, liquid, injectable solution, ointment and syrup formulations. In this case, one or more pharmaceutically acceptable excipients may be added to the composition.

In still another aspect, the present invention is directed to a composition for treating cancer, which comprises the nucleic acid complex according to the present invention. Tumor or cancers that can be treated by the composition according to the present invention are not particularly limited, but include both solid cancers and blood cancers. Preferably, the tumors or cancers include all kinds of cancers in which a target gene (e.g., surviving (a new target for anti-cancer therapy. Cancer Treat Rev. 35(7):553-62, 2009) is expressed. More preferably, the cancer may be selected from the group consisting of liver cancer, hepatocellular carcinoma, gastric cancer, breast cancer, lung cancer, ovarian cancer, bronchial cancer, nasopharyngeal cancer, laryngeal cancer, pancreatic cancer, bladder cancer, colorectal cancer, colon cancer, uterine cervical cancer, brain cancer, prostate cancer, bone cancer, skin cancer, thyroid cancer, parathyroid cancer, renal cancer, esophageal cancer, biliary tract cancer, testis cancer, rectal cancer, head and neck cancer, ureteral cancer, osteosarcoma, neurocytoma, melanoma, fibrosarcoma, rhabdomyosarcoma, astrocytoma, neuroblastoma and neuroglioma.

Preferably, a target gene, to which the bioactive nucleic acid contained in the nucleic acid complex for treating cancer according to the present invention binds, may be any one or more selected from the group consisting of Survivin, VEGF, Androgen receptor, KRAS, Clusterin, TGFßR2, ERBB3, Transglutaminase 2, ABCB1, Hsp27, STAT3, and PD-L, but is not limited thereto.

Preferably, the composition for treating cancer according to the present invention comprises: a survivin-specific bioactive peptide nucleic acid having a sequence of any one of SEQ ID NOs: 1 to 18; and a carrier peptide nucleic acid complementary thereto. The carrier peptide nucleic acid may preferably have any one sequence selected from among SEQ ID NOs: 19 to 40, and a portion of the sequence may be substituted with universal bases.

In addition, the composition for treating cancer according to the present invention comprises: a VEGF-specific bioactive peptide nucleic acid represented by SEQ ID NO: 41 or a PD-L1-specific bioactive peptide nucleic acid represented by SEQ ID NO: 49; and a carrier peptide nucleic acid complementary thereto. The carrier peptide nucleic acid may preferably have a sequence of SEQ ID NO: 42, 43 (VEGF) or 50 (PD-L1), and a portion of the sequence may be substituted with universal bases.

In still another aspect, the present invention is directed to a composition for treating age-related macular degeneration, which comprises the nucleic acid complex according to the present invention. A target gene, to which the bioactive nucleic acid contained in the nucleic acid complex for treating age-related macular degeneration binds, may be VEGF, but is not limited thereto.

Preferably, the composition for treating age-related macular degeneration according to the present invention comprises: a VEGF-specific bioactive peptide nucleic acid represented by SEQ ID NO: 41; and a carrier peptide nucleic acid complementary thereto. The carrier peptide nucleic acid may preferably have a sequence of SEQ ID NO: 42 or 43, and a portion of the sequence may be substituted with universal bases.

In still another aspect, the present invention is directed to a composition for preventing or treating skin diseases, which comprises the nucleic acid complex according to the present invention. Examples of the skin diseases include, but are not limited to, psoriasis, pigmentation-related skin diseases, and atopic diseases. A target gene, to which the bioactive nucleic acid contained in the nucleic acid complex binds, may be any one or more selected from the group consisting of IFI16, TLR6, and TIEG1, but is not limited thereto.

Preferably, the present invention is directed to a composition for treating psoriasis. The composition for treating psoriasis according to the present invention comprises: an IFI16-specific bioactive peptide nucleic acid having a sequence of any one of SEQ ID NOs: 44 to 47; and a carrier peptide nucleic acid complementary thereto. The carrier peptide nucleic acid may preferably have a sequence of SEQ ID NO: 48, and a portion of the sequence may be substituted with universal bases.

A composition for preventing or treating skin diseases may be prepared into formulations such as aqueous solution, cream, gel, paste, lotion, and ointment, but is not limited thereto.

In yet another aspect, the present invention is directed to a composition for treating inflammable diseases, which comprises the nucleic acid complex according to the present invention. A target gene, to which the bioactive nucleic acid contained in the nucleic acid complex for treating inflammable diseases binds, may be any one or more selected from the group consisting of PDE4B and Pellino-1, is not limited thereto.

In yet another aspect, the present invention is directed to a composition for treating rare diseases and severe diseases, which comprises the nucleic acid complex according to the present invention. A target gene, to which the bioactive nucleic acid contained in the nucleic acid complex for treating rare diseases and severe diseases binds, may be any one or more selected from the group consisting of SMN2, ApoB-100, ICAM-1, ApoCIII, TTR, HTT, GHr, SOD1, ANGPTL3, PKK, miR-21, TMPRSS6, FMR1, and Connexin 26, is not limited thereto.

Preferably, the rare diseases and severe diseases according to the present invention are deafness, and a target gene, to which the bioactive nucleic acid contained in the nucleic acid complex binds, may be Connexin 26.

The complex of the present invention may be administered (or applied) via a carrier such as liposome. The liposome may aid in targeting the complex toward a specific tissue, such as lymphoid tissue, or specifically targeting the complex toward infected cells, and may also help to increase the half-life of the composition comprising the complex. Examples of the liposome include emulsions, foams, micelles, insoluble monolayers, liquid crystals, phospholipid dispersions, lamellar layers, and the like. In these preparations, the complex to be delivered is incorporated as part of a liposome, alone or in conjunction with a molecule which binds to, e.g., a receptor prevalent among lymphoid cells, such as monoclonal antibodies which bind to the CD45 antigen, or with other therapeutic compositions. Thus, liposomes either filled or decorated with a desired complex of the invention of the invention can be directed to the site of lymphoid cells.

Liposomes for use in the present invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes. For example, methods as disclosed in literatures [Szoka, et al., Ann. Rev. Biophys. Bioeng., 9:467, 1980), and U.S. Pat. Nos. 4,235,871, 4,501,728, 4,837,028, and 5,019,369] can be used.

In one embodiment, the present invention provides a method of treating and suppressing (or alleviating) disease by administering (or applying) the complex or a composition comprising the complex to a subject.

A disease which can be treated using the complex of the present invention is determined according to the characteristics of the bioactive nucleic acid used, and is not particularly limited.

Examples of diseases which can be treated using the complex of the present invention include cancer, abnormal blood vessel growth-related disease such as macular degeneration, skin diseases, inflammatory diseases, autoimmune diseases, and the like, but are not limited thereto.

A composition comprising the complex according to the present invention may be administered (or applied) in a pharmaceutically effective amount in order to treat cancer diseases or suppress (or alleviate) cancer symptoms. The dose/application amount of the pharmaceutical composition of the present invention may vary depending on various factors such as the kind of pigmentation-related skin diseases, an age, a body weight, characteristics and degree of symptoms of a patient, the kind of current treatment method, a treatment frequency, an administration (application) form and route, and the like, and may be easily determined by those of ordinary skill in the related art. The composition of the present invention may be administered (applied) together with the pharmacological or physiological ingredient, or sequentially administered (applied). In addition, the composition of the present invention may also be administered (applied) in combination with conventional additional therapeutic agents, and sequentially or simultaneously with the conventional therapeutic agent. The administration (application) may be single dose administration (application) or multi-dose administration (application).

As used herein, the term "subject" refers to a mammal suffering from a condition or disease which can be alleviated, suppressed or treated by administering (applying) the complex of the present invention, or being at risk of developing this condition or disease. Preferably, it refers to a human being.

In addition, the dose (application amount) of the compound of the invention to the human body may vary depending on the age, body weight, gender, administration (application) form, health condition, and disease severity of a patient. Based on an adult patient weighing 70 kg, it is generally 0.001 to 1,000 mg/day, preferably 0.01 to 500 mg/day. Depending on the judgment of a doctor or a pharmacist, it may be administered (applied) once or several times a day at a predetermined time interval.

For any compound or a mixture comprising the same used in the methods described herein, the therapeutically effective amount or dose can be estimated initially from cell culture assays. For example, a dose can be formulated in animal models to achieve a circulating plasma concentration range that includes the IC50 (half maximal inhibitory concentration) or the EC50 (half maximal effective concentration) as determined in cell culture. Such information can be used to more accurately determine useful doses in humans.

Toxicity and therapeutic efficacy of the complex described herein or a mixture comprising the same can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}$ (or $IC_{50}$)/$LD_{50}$. Compounds that exhibit large therapeutic indices are preferred. The data obtained from these cell culture assays can be used in formulating a range of doses for use in humans. The dosages of these compounds lay preferably within a range of circulating concentrations that include the $ED_{50}$ (or $IC_{50}$) with little or no toxicity.

In yet another aspect, the present invention is directed to a kit for diagnosing cancer or tumor, which comprises the complex of the present invention.

In the present invention, a sample for diagnosing cancer or tumor may be derived from specific tissues or organs of mammals, including humans. Representative examples of tissues include connective tissue, muscle, or nerve tissue. Representative examples of organs include eyes, brain, lung, liver, spleen, bone marrow, thymus, heart, lymph, blood, bone, cartilage, pancreas, kidney, gallbladder, stomach, small intestine, testis, ovary, uterus, rectum, nervous system, and gland and internal blood vessels.

The sample includes any cell, tissue or fluid that is derived from a biological origin, or any other medium that can be well analyzed by the present invention. The sample also includes a sample obtained from foods produced for consumption of humans and/or animals. In addition, the to-be-analyzed sample includes a body fluid sample, which includes, but not limited to, blood, serum, plasma, lymph, breast milk, urine, feces, ocular fluid, saliva, semen, brain extracts (e.g., grinded brain), spinal fluid, appendix, spleen, and tonsil tissue extracts.

The kit of the present invention may optionally include reagents required for performing a target nucleic acid amplification reaction (e.g., PCR reaction), such as buffer, DNA polymerase cofactor, and deoxyribonucleotide-5-triphosphate. Alternatively, the kit may also include an antibody that inhibits the activities of various polynucleotide molecules, a reverse transcriptase, buffers and reagents, and a DNA polymerase. In addition, in the kit, the optimal amount of the reagent used in a specific reaction can be easily determined by those skilled in the art who have acquired the disclosure set forth herein. Typically, the kit of the invention may be manufactured as a separate package or compartment containing the above mentioned ingredients.

Figure 1:
FIG. 1 shows a comparison of particle size between a single-stranded bioactive nucleic acid and a nucleic acid complex represented by structural formula (1), which comprises a bioactive nucleic acid bound parallel to a carrier peptide nucleic acid.
Figure 1:
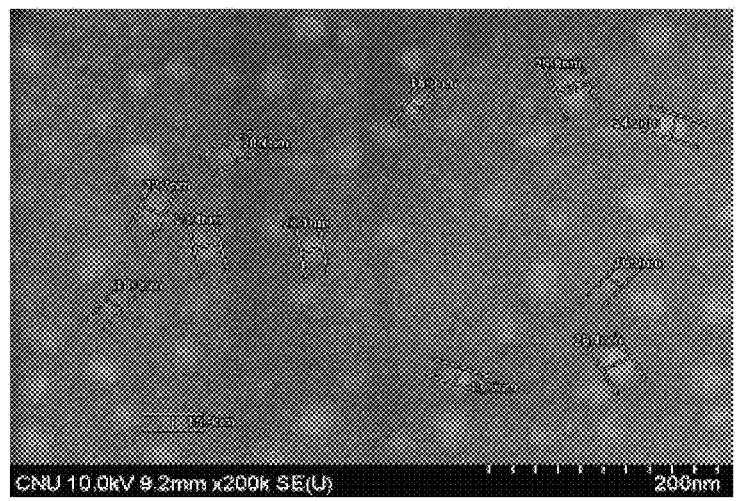

In an example of the present invention, the particle size of the nucleic acid complex formed by binding was analyzed. As a result, as shown in FIG. 1, it was confirmed that the particle size of the nucleic acid complex was reduced to several tens of nm compared to a single-stranded nucleic acid (see Example 2).

In another example of the present invention, the cell permeability of the nucleic acid complex was analyzed. As a result, as shown in FIGS. 2a and 2b, it was confirmed that intracellular Cy3 fluorescence (marker) was the highest due to intracellular introduction of a charged nucleic acid complex, and a complex in which a non-charged bioactive peptide nucleic acid and carrier peptide nucleic acid did not form a duplex showed low intracellular permeability (see Example 3).

In still another example of the present invention, the efficiency of inhibition of expression of a target gene in a tumor cell line by the nucleic acid complex was analyzed. As a result, as shown in FIGS. 3a to 3c, the analysis of expression patterns of the target protein and its downstream proteins indicated that expression of survivin and its downstream proteins in the test group treated with the nucleic acid complex was inhibited (see Example 4).

In yet another example of the present invention, it was confirmed that the time point at which expression of the target gene survivin protein was controlled by controlling the binding affinity of the nucleic acid complex, and an experiment performed in a tumor cell line using nucleic acid complexes comprising survivin- and VEGF-specific bioactive nucleic acids indicated that the nucleic acid complexes exhibited anticancer activity (see Examples 5 to 8).

In still another example of the present invention, it was confirmed that the use of the complex structure could inhibit the growth of bacteria and fungi (see Example 12).

The carrier peptide nucleic acid (i.e., modified carrier peptide nucleic acid) according to the present invention overcomes a precipitation problem caused by the self-aggregation property of a conventional non-modified naked-PNA, and can increase cell permeability, solubility and intracellular diffusion effects.

Therefore, in still another aspect, the present invention is directed to a method of regulating expression of a target gene using a complex, the method comprising the steps of: (a) forming the complex by binding of a bioactive nucleic acid to a carrier peptide nucleic acid; and (b) introducing the complex into target cells by bringing the complex into contact with the target cells.

In the present invention, the target cells may be the above-described cancer or tumor cells, but are not limited thereto. In the present invention, after the complex is introduced into the cells in step (b) and moves, the bioactive nucleic acid may bind to a target nucleic acid having a nucleotide sequence complementary thereto and may be separated from the carrier peptide nucleic acid, and the bioactive nucleic acid may bind to the target gene and regulate expression of the target gene.

According to the present invention, the bioactive nucleic acid and the carrier peptide nucleic acid of the complex maintain complementary binding therebetween in the absence of a target nucleic acid (target sequence), whereas in the presence of a target nucleic acid complementary to the nucleotide sequence of the bioactive nucleic acid, the bioactive nucleic acid is separated from the carrier peptide nucleic acid and binds to the target nucleic acid by "strand displacement of the bioactive nucleic acid to the target sequence" and "target-specific release and binding". The time of the release and binding can be controlled by controlling the hydrogen bonding strength between nucleobases of the bioactive nucleic acid according to the complementarity between the nucleotide sequence of the carrier peptide nucleic acid and the nucleotide sequence of the target sequence.

Therefore, according to a preferred embodiment of the present invention, the target-specific release and binding may be achieved by: i) constructing "single nucleotide polymorphism (SNP)" or "a sequence shorter than the bioactive nucleic acid" as a carrier peptide nucleic acid structure having a partial specific sequence; ii) replacing a portion of the carrier peptide nucleic acid sequence with universal bases; iii) replacing a portion of the carrier peptide nucleic acid sequence with a linker; or vi) providing a carrier peptide nucleic acid structure which bind parallel to the bioactive nucleic acid such that the binding affinity between the carrier peptide nucleic acid and the bioactive nucleic acid is lower than the binding affinity between the target nucleic acid and the bioactive nucleic acid. These methods may be used in combination of two or more, and the parallel binding method is preferably used.

The universal base that can be used in the present invention may be one or more selected from the group consisting of natural bases, including adenine, guanine, cytosine, thymine, and uracil, and inosine PNA, indole PNA, nitroindole PNA, and abasic, which are bases that bind without selectivity and have lower binding affinity than complementary binding affinity. Preferably, inosine PNA may be used as the universal base.

There is an advantage in that the time of separation between the bioactive nucleic acid and the carrier peptide nucleic acid and the time of binding between the bioactive nucleic acid and the target gene of the bioactive nucleic acid can be controlled by controlling the binding affinity between the bioactive nucleic acid and the carrier peptide nucleic acid.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1: Bioactive Nucleic Acid and Carrier Peptide Nucleic Acid, and Production of Complex Using Them In order to verify the efficacy of the nucleic acid complex represented by structural formula (1) according to the present invention, survivin was used as a target gene. Survivin is a protein that is expressed commonly in most neoplastic tumors or transgenic cell lines, tested until now, and is expected to be an important target in anticancer therapy (survivin: a new target for anti-cancer therapy. Cancer Treat Rev. 35(7):553-62, 2009).

To suppress survivin, antisense PNA and RNA were used as bioactive nucleic acids against survivin.

The antisense PNA and RNA against survivin according to the present invention have the sequences set forth in SEQ ID NOs: 1 to 18. The peptide nucleic acid-based bioactive nucleic acids used in this Example were labeled with Cy3 for imaging at the 3' end, and the nucleotide sequences, monomer modifications and structures thereof are shown in Table 2 below.

All the peptide nucleic acids used in the present invention were synthesized using a HPLC purification method by PANAGENE (Korea).

Carrier peptide nucleic acids used in the present invention to deliver the survivin gene-targeting bioactive nucleic acid into cells have sequences set forth in SEQ ID NOs: 19 to 40. The nucleotide sequences, monomer modifications and structures of the carrier peptide nucleic acids used in this Example are shown in Table 2 below.

For analysis of the particle size, cell permeability and target gene expression inhibitory efficiency of the complexes, combinations of the bioactive nucleic acids and carrier peptide nucleic acids shown in Table 2 below were used for the production of the complexes.

TABLE 2

Sequences of bioactive nucleic acids for inhibition of survivin activity and carrier peptide nucleic acids

| Classification | SEQ ID NO | Nucleotide sequences | Monomer modification |
|---|---|---|---|
| Bioactive nucleic acids | SEQ ID NO: 1 | 5'-CTITCCTAAGACATTGC-O-K-3' | |
| | SEQ ID NO: 2 | 5'-TCCT$^{(-)}$TTCCTAAGACAT$^{(-)}$TGC-O-K-3' | - - |
| | SEQ ID NO: 3 | 5'-CTT$^{(-)}$TCCTA$^{(+)}$AGACAT$^{(-)}$TGC-O-K-3' | -+- |
| | SEQ ID NO: 4 | 5'-CTT$^{(-)}$TC CTA$^{(-)}$AGACAT$^{(-)}$T-O-K-3' | - - - |
| | SEQ ID NO: 5 | 5'-CTT$^{(-)}$TC C$^{(+)}$TAAG$^{(+)}$ACAT$^{(-)}$T-O-K-3' | -++- |
| | SEQ ID NO: 6 | 5'-CTT$^{(-)}$TC$^{(+)}$CTA$^{(-)}$AGA$^{(+)}$CAT$^{(-)}$TGC-O-K-3' | -+-+- |
| | SEQ ID NO: 7 | 5'-TTC$^{(-)}$TC$^{(+)}$AGT$^{(-)}$GGG$^{(+)}$GCA$^{(-)}$GTG-O-K-3' | -+-+- |
| | SEQ ID NO: 8 | 5'-TC$^{(-)}$TC$^{(+)}$AGT$^{(-)}$GGG$^{(+)}$GCA$^{(-)}$GTG-O-K-3' | -+-+- |
| | SEQ ID NO: 9 | 5'-TC$^{(-)}$TC$^{(+)}$AGT$^{(-)}$GGG$^{(+)}$GCA$^{(-)}$GT-O-K-3' | -+-+- |
| | SEQ ID NO: 10 | 5'-C$^{(-)}$TC$^{(+)}$AGT$^{(-)}$GGG$^{(+)}$GCA$^{(-)}$GT-O-K-3' | -+-+- |
| | SEQ ID NO: 11 | 5'-C$^{(-)}$TC$^{(+)}$AGT$^{(-)}$GGG$^{(+)}$GCA$^{(-)}$G-O-K-3' | -+-+- |
| | SEQ ID NO: 12 | 5'-CT$^{(-)}$TTC$^{(+)}$CT$^{(-)}$AA$^{(+)}$GA$^{(-)}$CA$^{(+)}$TT$^{(-)}$GC-O-K-3' | -+-+-+- |
| | SEQ ID NO: 13 | 5'-CTTTCCTAAGACATTGC-O-K(Cy3)-3' | |
| | SEQ ID NO: 14 | 5'-CTT$^{(-)}$TC$^{(+)}$CTA$^{(-)}$AGA$^{(+)}$CAT$^{(-)}$TGC-O-K(Cy3)-3' | -+-+- |
| | SEQ ID NO: 15 | 5'-CTTTCCTA$^{(-)}$AGACATTGC-O-K (Cy3)-3' | - |
| | SEQ ID NO: 16 | 5'-CTT$^{(-)}$TCCTA$^{(+)}$AGACAT$^{(-)}$TGC-O-K (Cy3)-3' | -+- |
| | SEQ ID NO: 17 | 5'-TCCT$^{(-)}$TTCCTAAGACAT$^{(-)}$TGC-O-K(Cy3)-3' | - - |
| | SEQ ID NO: 18 | 5'-TCCT$^{(-)}$TTCCTAA$^{(-)}$GACAT$^{(-)}$TGC-O-K(Cy3)-3' | - - - |
| Carrier peptide nucleic acids | SEQ ID NO: 19 | 5'-GAAAGGATTCTGTAACG-O-K-3' | |
| | SEQ ID NO: 20 | 5'-GAAAGGAT$^{(+)}$TCTGTAACG-O-K-3' | + |
| | SEQ ID NO: 21 | 5'-GAAAGGAT$^{(+)}$T-O-TGTAACG-O-K-3' | + |
| | SEQ ID NO: 22 | 5'-GAAAG-O-AT$^{(+)}$TC-O-GTAACG-O-K-3' | + |

TABLE 2-continued

Sequences of bioactive nucleic acids for inhibition of survivin activity and carrier peptide nucleic acids

| Classification | SEQ ID NO | Nucleotide sequences | Monomer modification |
|---|---|---|---|
| | SEQ ID NO: 23 | 5'-GAA$^{(+)}$AGGATTCTGTA$^{(+)}$ACG-O-K-3' | ++ |
| | SEQ ID NO: 24 | 5'-GAA$^{(+)}$AGGATT-O-TGTA$^{(+)}$ACG-O-K-3' | ++ |
| | SEQ ID NO: 25 | 5'-GAA$^{(+)}$AG-O-ATTC-O-GTA$^{(+)}$ACG-O-K-3' | ++ |
| | SEQ ID NO: 26 | 5'-GAA$^{(+)}$AGGAT$^{(-)}$TCTGTA$^{(+)}$ACG-O-K-3' | +−+ |
| | SEQ ID NO: 27 | 5'-GAA$^{(+)}$AGGAT$^{(-)}$T-O-TGTA$^{(+)}$ACG-O-K-3' | +−+ |
| | SEQ ID NO: 28 | 5'-GAA$^{(+)}$AG-O-AT$^{(-)}$TC-O-GTA$^{(+)}$ACG-O-K-3' | +−+ |
| | SEQ ID NO: 29 | 5'-GAA$^{(-)}$AGGATTCTGTA$^{(-)}$ACG-O-K-3'' | −− |
| | SEQ ID NO: 30 | 5'-GAA$^{(-)}$AGGATT-O-TGTA$^{(-)}$ACG-O-K-3'' | −− |
| | SEQ ID NO: 31 | 5'-GAA$^{(-)}$AG-O-ATTC-O-GTA$^{(-)}$ACG-O-K-3'' | −− |
| | SEQ ID NO: 32 | 5'-GAA$^{(+)}$AGGAT$^{(+)}$TCTGTA$^{(+)}$ACG-O-K | +++ |
| | SEQ ID NO: 33 | 5'-AG$^{(+)}$AGTCAC$^{(+)}$CCCGT$^{(+)}$CAC-O-K-3'' | +++ |
| | SEQ ID NO: 34 | 5'-AG$^{(+)}$AGTCAC$^{(+)}$CCCGT$^{(+)}$CA-O-K-3'' | +++ |
| | SEQ ID NO: 35 | 5'-G$^{(+)}$AGTCAC$^{(+)}$CCCGT$^{(+)}$CA-O-K-3'' | +++ |
| | SEQ ID NO: 36 | 5'-G$^{(+)}$AGTCAC$^{(+)}$CCCGT$^{(+)}$C-O-K-3'' | +++ |
| | SEQ ID NO: 37 | 5'-GAA$^{(+)}$AGG$^{(+)}$ATT$^{(+)}$CTGT$^{(+)}$AA$^{(+)}$CG-O-K | +++++ |
| | SEQ ID NO: 38 | 5'-GAAAGGATTCTGTAACG-O-K(Cy3)-3' | |
| | SEQ ID NO: 39 | 5'-GAA$^{(+)}$AGGAT$^{(+)}$TCTGTA$^{(+)}$ACG-O-K (Alexa488)-3' | +++ |
| | SEQ ID NO: 40 | 5'-GAA$^{(+)}$AGGAT$^{(+)}$TCTGTA$^{(+)}$ACG-O-K(Cy3)-3' | +++ |

For monomer modification, a peptide nucleic acid backbone modified to be positively charged using lysine (Lys, K; indicated by $^{(+)}$) and a peptide backbone modified to be negatively charged using glutamic acid (Glu, E; indicated by $^{(-)}$) were constructed.

Each bioactive nucleic acid and each carrier peptide nucleic acid were hybridized to each other in DMSO, and as a result, complexes, each comprising the bioactive nucleic acid and the carrier peptide nucleic acid, were synthesized.

Example 2: Binding of Bioactive Nucleic Acid to Carrier Peptide Nucleic Acid and Analysis of Particle Size of Complexes with Various Electrical Properties The particle size of each of the bioactive peptide nucleic acid/carrier peptide nucleic acid complexes, prepared to have the structures shown in Table 2 above in Example 1, was analyzed.

Example 2-1: Field Emission Scanning Electron Microscopy (FE-SEM) Analysis

The particle sizes of the complexes produced in Example 1 were analyzed by field emission scanning electron microscopy. For emission scanning electron microscopy, 3 µl of each complex produced by hybridizing 250 nM of each carrier peptide nucleic acid with 250 nM of each bioactive nucleic acid was dropped onto a silicon wafer, and then frozen at −70° C. for 1 hour, followed by freeze drying for 20 minutes. The dried complex was coated on osmium for 10 minutes, and then analyzed by field emission scanning electron microscopy at 5 kV to 10 kV.

Example 2-2: Field Emission Scanning Electron Microscopy (FE-SEM) Analysis of Complex Structures with Various Electrical Properties Complexes with various electrical properties were produced according to the method of Example 1, and the particle sizes thereof were analyzed according to the method of Example 2-1.

As a result, as shown in FIG. 1, it was confirmed that the particle size of the complex produced by parallel binding of the bioactive nucleic acid and the carrier peptide nucleic acid, which had different electrical properties, was smaller than the particle size of the single-stranded bioactive nucleic acid. Furthermore, as shown in FIGS. 2a and 2b, the particle sizes of the following PNA duplexes (complexes) were analyzed: PNA duplex 1 composed of a bioactive peptide nucleic acid (SEQ ID NO: 6) and a carrier peptide nucleic acid (SEQ ID NO: 32); PNA duplex 2 composed of a bioactive peptide nucleic acid (SEQ ID NO: 5) and a carrier peptide nucleic acid (SEQ ID NO: 32) having three positive charges; PNA duplex 3 composed of a bioactive peptide nucleic acid (SEQ ID NO: 1) and a carrier peptide nucleic acid (SEQ ID NO: 37); and PNA duplex 4 composed of a non-charged bioactive peptide nucleic acid (SEQ ID NO: 1) and a carrier peptide nucleic acid (SEQ ID NO: 23). As the number of positive charges of the carrier peptide nucleic acid increased from 2 to 3, the particle size decreased, but when the number of positive charges exceeded 5, the particle size increased. In addition, regarding other factors that determine the particle size, it was confirmed that the particle size of the complex varied depending on the proper electrical properties of the carrier peptide nucleic acid and the bioactive peptide nucleic acid with the charges of the bioactive peptide nucleic acid of the complex.

Example 3: Analysis of Cell Permeability According to Characteristics of Carrier Peptide Nucleic Acid The cell permeability of each of the bioactive nucleic acid/carrier peptide nucleic acid complexes, prepared to have the structures shown in Table 2 above in Example 1, was analyzed.

Example 3-1: Cell Culture

Human uterine cancer cells (HeLa) obtained from the ATCC (American Type Culture Collection, USA) were cultured in DMEM medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$.

Example 3-2: Intracellular Introduction of Complex Comprising Bioactive Nucleic Acid and Carrier Peptide Nucleic Acid The HeLa cells ($5 \times 10^3$ cells/well) cultured in Example 3-1 were cultured in a 8-well plate for 24 hours under the same culture conditions, and then treated with 500 nM of the complex prepared by binding the bioactive peptide nucleic acid to the carrier peptide nucleic acid in Example 1. The treated cells were incubated at 37° C. under 5% (v/v) $CO_2$ for 24, 48, 72 and 96 hours, and then intracellular introduction of the complex was measured.

Example 3-3: Analysis of Intracellular Permeability of Complex Comprising Bioactive Nucleic Acid and Carrier Peptide Nucleic Acid The degree of intracellular introduction of the complex comprising the bioactive peptide nucleic acid and the carrier peptide nucleic acid was observed by confocal microscopy. The nucleus was stained with DAPI, and the bioactive peptide nucleic acid was labeled with Cy3 in order to confirm whether it would be introduced into cells.

Example 3-4: Analysis of Whether Complex of Bioactive Nucleic Acid and Carrier Peptide Nucleic Acid would be Separated in the Presence of Target Gene in Cells In order to examine whether the bioactive peptide nucleic acid and the carrier peptide nucleic acid are introduced into cells, meet a target gene and are separated from each other, whether the signal of the bioactive nucleic acid labeled with Cy3 would overlap with the signal of the carrier peptide nucleic acid labeled with Alexa488 was observed by confocal microscopy.

Example 3-5: Analysis of Intracellular Permeability of Single Antisense siRNA Using Carrier Peptide Nucleic Acid The degree of intracellular introduction of a complex comprising a bioactive single antisense siRNA bound to the carrier peptide nucleic acid was analyzed by confocal microscopy. The nucleus was stained with DAPI, and the bioactive single antisense siRNA was labeled with Cy3 in order to confirm whether it would be introduced into cells.

As a result, as shown in FIGS. 3a to 3c, it was confirmed that intracellular Cy3 fluorescence was the highest due to intracellular introduction of the complex composed of the charged bioactive peptide nucleic acid (SEQ ID NO: 14) and the carrier peptide nucleic acid (SEQ ID NO: 32), and that when the bioactive peptide nucleic acid and the carrier peptide nucleic acid did not form a duplex or the complex had no electric charge, the intracellular permeability of the complex composed of the bioactive peptide nucleic acid (SEQ ID NO: 1) and the carrier peptide nucleic acid (SEQ ID NO: 19) was low. In addition, it could be seen that the intracellular permeability of the complex varied depending on the electrical property thereof and the type of complex. As can be seen in FIG. 4, it was confirmed that the complex composed of the bioactive peptide nucleic acid (SEQ ID NO: 14) showing biological stability and the carrier peptide nucleic acid (SEQ ID NO: 32) showed high intracellular permeability and was also present in the cells for a long period of time. As shown in FIGS. 5a to 5f, it was observed that the complex composed of the bioactive nucleic acid (SEQ ID NO: 14) and the carrier peptide nucleic acid (SEQ ID NO: 39), which had the same charge, was present in a bound state after intracellular introduction, and then separated after 48 hours. As shown in FIGS. 6a to 6g, it was observed that the single siRNA having the same sequence as that of the bioactive nucleic acid shown in Table 2 did not permeate the cells by itself, but the complex composed of the carrier peptide nucleic acid (SEQ ID NO: 39) and the single siRNA permeated the cells with high efficiency.

Example 4: Inhibition of Expression of Target Gene in Tumor Cell Lines by Complex Comprising Bioactive Nucleic Acid and Carrier Peptide Nucleic Acid Using each of the bioactive peptide nucleic acid/carrier peptide nucleic acid complexes prepared to have the structures shown in Table 2 above in Example 1, the efficiency of inhibition of target gene expression in tumor cell lines by the complex was analyzed.

Example 4-1: Cell Culture

Human colorectal cancer cells (SW480) and human breast cancer cells (SK-BR-3), purchased from the ATCC, were cultured in RPMI 1640 medium (Roswell Park Memorial Institute, Welgene, Korea) containing 10% (v/v) fetal bovine serum, 100 units/ml penicillin and 100 µg/ml streptomycin at 37° C. under 5% (v/v) $CO_2$.

Example 4-2: Cell Culture and Intracellular Introduction of Complex Comprising Bioactive Nucleic Acid and Carrier Peptide Nucleic Acid Culture conditions for human cancer cells and a method of treating the cells with the complex comprising the bioactive peptide nucleic acid and the carrier peptide nucleic acid were as described in Example 3. However, $1 \times 10^5$ cells/well were cultured in 6-well plates and treated with the complex, and then incubated for 72 and 96 hours, after which expression of the target gene would be inhibited was examined.

Example 4-3: Analysis of Gene Expression by Western Blot Assay

From each cell line treated under the conditions described in Example 4-2, total protein was extracted and quantified by BCA (Bicinchoninic acid assay). The protein was separated by size on SDS-PAGE gel, and the separated protein on the gel was transferred to a membrane. The membrane was incubated with anti-survivin antibody (Cell Signaling, USA) and anti-CyclinD1 (SantaCruz, USA) rabbit antibody as primary antibodies and incubated with anti-rabbit antibody (SantaCruz, USA) as secondary antibody. Next, the membrane was treated with ECL (Enhanced chemiluminescence, Amersham, USA) solution. After completion of the antibody treatment and washing procedures, protein expression patterns of survivin and its downstream gene Cyclin D1 on the membrane were analyzed under LAS.

As a result, as shown in FIG. 7, PNA 1 and PNA 2 are complexes of a bioactive peptide nucleic acid, which has the same sequence as shown in Table 2 but have a different electrical property, and a carrier peptide nucleic acid having the same electrical property. Specifically, PNA 1 is a complex composed of a bioactive peptide nucleic acid (SEQ ID NO: 3) and a carrier peptide nucleic acid (SEQ ID NO: 32), and PNA 2 is a complex composed of a bioactive peptide nucleic acid (SEQ ID NO: 6) and a carrier peptide nucleic acid (SEQ ID NO: 32). It was confirmed that the complexes having different electrical properties inhibited expression of survivin and its downstream protein in expression pattern analysis, even though the time of inhibition of gene expression did differ depending on the electrical properties of the complexes.

Example 5: Inhibition of Target Gene Expression in Tumor Cell Line by Control of Complex Comprising Bioactive Nucleic Acid and Carrier Peptide Nucleic Acid Using control of bioactive peptide nucleic acid/carrier peptide nucleic acid complexes having various electrical properties, prepared to have the structures shown in Table 2 above in Example 1, the efficiency of inhibition of target gene expression in tumor cell lines by each complex was analyzed.

Example 5-1: Cell Culture and Intracellular Introduction of Complex Comprising Bioactive Nucleic Acid and Carrier Peptide Nucleic Acid Culture Conditions for SW480 and SK-BR-3 cells and a method of treating the cells with a complex comprising a bioactive peptide nucleic acid bound to a carrier peptide nucleic acid were as described in Example 2. However, $1 \times 10^5$ cells/well were cultured in 6-well plates and treated with the complex, and then incubated for 24, 48, 72 and 96 hours, after which expression of the target gene would be inhibited was examined.

Example 5-2: Analysis of Gene Expression by Western Blot Assay

An experiment was performed under the conditions of Example 4-1, and the efficiency of inhibition of target gene expression in the tumor cell line by control of the complex comprising the bioactive peptide nucleic acid and the carrier peptide nucleic acid was analyzed.

As a result, as shown in FIG. 8, the bioactive peptide nucleic acids and carrier peptide nucleic acids having the same sequences as shown in Table 2 above were used, but the complexes used were composed of the same positively charged carrier peptide nucleic acid and each of different bioactive peptide nucleic acids having various electrical properties. In FIG. 8, A represents a complex comprising a bioactive peptide nucleic acid (SEQ ID NO: 1); B represents a complex comprising a bioactive peptide nucleic acid (SEQ ID NO: 2); and C and D represent complexes comprising a bioactive peptide nucleic acid (SEQ ID NO: 12). The expression patterns of survivin protein and its downstream proteins by these complexes were analyzed. It was confirmed that the time of inhibition of expression of survivin and its downstream proteins changed depending on the structure of the bioactive peptide nucleic acid/carrier peptide nucleic acid complexes having different electrical properties.

Example 6: Analysis of Cell Viability in Tumor Cell Line Using Bioactive Peptide Nucleic Acid/Carrier Peptide Nucleic Acid Complexes Having Various Lengths Using various bioactive peptide nucleic acid/carrier peptide nucleic acid complexes having the same electrical property and different lengths, prepared to have the structures shown in Table 2 above in Example 1, the efficiency of inhibition of cell viability in a tumor cell line was analyzed.

Example 6-1: Cell Culture and Intracellular Introduction of Complex Comprising Bioactive Nucleic Acid and Carrier Peptide Nucleic Acid Culture conditions for the SW480 cell line and a method of treating the cells with the complex comprising the bioactive peptide nucleic acid bound to the carrier peptide nucleic acid were as described in Example 2 above. However, 6×10³ cells/well were cultured in 96-well plates and treated with the complex, and then incubated for 24, 48, 72 and 96 hours, after which cell viability after each incubation time was analyzed.

Example 6-2: Analysis of Cell Viability in Tumor Cell Line by MTT Assay

The cell line treated under the conditions of Example 6-1 was treated with 5 mg/mL of MTT (3-(4,5-dimethylthiazol-2-yl)-2,5-diphenyltetrazolium bromide) solution in 1×PBS, and 20 μL of the cell solution was added to each well and incubated for 4 hours, and then the OD (optical density) was measured by a spectrophotometer and analyzed.

As a result, as shown in FIGS. 9a and 9b, it was confirmed that the cell viability changed depending on the length of the complex comprising each of the bioactive peptide nucleic acids (SEQ ID NOs: 6 to 11) bound to each of the carrier peptide nucleic acids (SEQ ID NOs: 23 to 36).

Example 7: Evaluation of Anticancer Efficacy of Candidate Complex Comprising Survivin Gene-Targeting Bioactive Peptide Nucleic Acid and Carrier Peptide Nucleic Acid Using candidate complexes, each comprising a survivin gene-targeting bioactive peptide and a carrier peptide nucleic acid, prepared to have the structures shown in Table 2 above in Example 1, the inhibition of tumors by inhibition of target gene expression in animal models transplanted with tumor cells was analyzed.

Example 7-1: Cell Culture and Intracellular Introduction of Complex Comprising Bioactive Nucleic Acid and Carrier Peptide Nucleic Acid Culture conditions for the SW480 cell line, a method of treating the cells with the complex comprising the bioactive peptide nucleic acid bound to the carrier peptide nucleic acid, and the experimental contents were as described in Examples 4 and 5 above.

Example 7-2: Analysis of Cell Viability in Tumor Cell Line by MTT Assay

The cell line treated under the conditions of Example 6-1 was treated with 5 mg/mL of MTT (3-(4,5-dimethylthiazol-2-yl)-2,5-diphenyltetrazolium bromide) solution in 1×PBS, and 20 μL of the cell solution was added to each well and incubated for 4 hours, and then the OD (optical density) was measured by a spectrophotometer and analyzed.

Example 7-3: Analysis of Gene Expression by Western Blot Assay

Protein expression patterns of the cell line treated under the conditions of Example 4-1 were analyzed under the experimental conditions of Example 4-3.

Example 7-4: Evaluation of Anticancer Efficacy by Tail Vein Administration of Candidate Complex Comprising Bioactive Peptide Nucleic Acid and Carrier Peptide Nucleic Acid in Mice Transplanted with Human Colorectal Cancer Cell Line (SW480)

For evaluation of anticancer efficacy, human colorectal cancer cells (SW480) were cultured and adjusted to a cell concentration of 3×10⁷ cells/ml. 0.3 ml (9×10⁶ cells/mouse) of the cell culture was injected subcutaneously into the axillary region between the right scapular portion and chest wall of each of specific pathogen-free (SPF) BALB/C female nude mice (Nara Biotech Co, Korea). Each of candidate complex samples 1, 2 and 3 (1 and 2 mg/kg), each comprising the bioactive peptide nucleic acid and the carrier peptide nucleic acid, and a negative control (1 and 2 mg/kg), was administered into the tail vein of each mouse in an amount of 0.1 ml, twice a week (days 0, 3, 7, 10, 14 and 17). For all the animals, general conditions and body weight were measured at the start of injection and immediately before administration during the test period. After cancer cell transplantation, three directions (length×width×height) of each tumor were measured using Vernier calipers for each animal, a total of 9 times up to days 18 from a time point when the average tumor volume of each group reached 44.1 mm³, and then the tumor volume was calculated using the equation "length×width×height/2". On 18 days after the start of drug administration, blood was collected from the orbital vein by a heparin tube and centrifuged at 5000 rpm for 5 minutes, the supernatant plasma was isolated and dispensed in vials and stored at −70° C. Next, the mice were euthanized with $CO_2$ gas, and then the tumor was isolated and weighed in a chemical balance, and the tumor tissue was imaged.

Example 7-5: Analysis of Hepatotoxicity Marker in Blood from Mice Transplanted with Human Colorectal Cancer Cells (SW480)

Plasma was separated from the blood collected from the mice used in anticancer efficacy evaluation, and was diluted at a suitable ratio in the assay solution of an alanine aminotransferase (ALT) and aspartate aminotransferase (AST) assay kit (Biovision, USA), and 20 μL of the dilution was added to each well. In addition, standard materials that help quantify the amounts of alanine aminotransferase (ALT) and aspartate aminotransferase (AST) in serum were also prepared and added to each well. Next, a reaction solution (an enzyme/dye agent mixture including the assay solution) was prepared according to the method provided in the assay kit, and 100 μL of the reaction solution was added to each well and shaken well. Next, the OD at 570 nm was measured by a spectrophotometer.

As a result, as shown in FIGS. 10a and 10b, it was confirmed that the use of the candidate complex comprising the survivin gene-targeting bioactive peptide nucleic acid and the carrier peptide nucleic acid inhibited cell viability in the human colorectal cancer cells and also inhibited expression of the target gene survivin and its downstream proteins. As shown in FIGS. 11a to 11e, in the animal experiment by tail vein administration in the mice transplanted with the human colorectal cancer cells, unusual general conditions and a statistically significant loss in body weight were not observed in all the sample-administered groups, unlike the negative control group, during the test period from the day after administration to the last day. In addition, looking at the tumor volume on the last day (day 18), the groups administered with 1 mg/kg of samples 1, 2 and 3 showed tumor growth inhibition rates of 18.9% (p<0.01), 8.2% and 8.9%, respectively, compared to the group administered with 1 mg/kg of the negative control, and the groups administered with 2 mg/kg of samples 1, 2 and 3 showed tumor growth inhibition rates of 40.1% (p<0.001), 28.0% (p<0.001) and 31.7% (p<0.001), respectively, compared to the group administered with 2 mg/kg of the negative control. In the case of the tumor weight on the last day, the weight of the SW480 tumor isolated on 18 days after the start of drug administration was measured, and as a result, it could be seen that the groups administered with 1 mg/kg of samples 1, 2 and 3 showed tumor weight reductions of 18.9% (p<0.01), 8.9% and 8.5%, respectively, compared to the group administered with 1 mg/kg of the negative control, and the groups administered with 2 mg/kg of samples 1, 2 and 3 showed tumor weight reductions of 40.7% (p<0.001), 28.9% (p<0.001) and 32.7% (p<0.001), respectively, compared to the group administered with 2 mg/kg of the negative control. Finally, blood was collected in the mice used in anticancer efficacy evaluation, and the presence or absence of hepatotoxicity markers in the blood was analyzed. As a result, no specific hepatotoxicity marker was detected in all the groups administered with the samples.

Example 8: Evaluation of the Anticancer Pharmacological Effect of Novel Complex by Inhibition of Vascular Endothelial Growth Factor in Human Breast Cancer Cells and Lung Cancer Cells The vascular endothelial growth factor VEGF shown to be highly expressed in many kinds of cancer cells is known to induce vascular growth in cancer cells, the anticancer pharmacological effect by VEGF inhibition of the novel complex was evaluated.

Example 8-1: Cell Culture

Human breast cancer cells (MDA-MB-231) and human lung cancer cells (A549), obtained from the ATCC (American Type Culture Collection, USA), were cultured in DMEM medium (Dulbecco Modified Eagle Medium, Welgene, Korea) containing 10% (v/v) fetal bovine serum, 100 units/ml penicillin and 100 µg/ml streptomycin at 37° C. under 5% (v/v) $CO_2$.

Example 8-2: Cell Culture and Intracellular Introduction of Complex Comprising Bioactive Peptide Nucleic Acid and Carrier Peptide Nucleic Acid To produce a novel complex for inhibiting vascular endothelial growth factor, a bioactive peptide nucleic acid having a sequence (SEQ ID NO: 41) complementary to VEGF mRNA, a gene essential for vascular growth, was constructed, and carrier peptide nucleic acids (SEQ ID NOs: 42 and 43) complementary to the bioactive peptide nucleic acid were constructed. The bioactive peptide nucleic acid was hybridized with the same amount of each of the carrier peptide nucleic acids, thereby producing complexes (see Table 3). A method of treating cells with the complex comprising the bioactive peptide nucleic acid bound to the carrier peptide nucleic acid was as described in Example 2.

TABLE 3

Sequences of bioactive nucleic acid for inhibition of VEGF activity and carrier peptide nucleic acids

| Classification | SEQ ID NO | Nucleotide sequences | Monomer modification |
| --- | --- | --- | --- |
| Bioactive nucleic acid | SEQ ID NO: 41 | 5'-AT$^{(-)}$GA$^{(+)}$TTC$^{(-)}$TG$^{(+)}$CCC$^{(-)}$TCC-O-K-3'' | -+-+- |
| Carrier peptide nucleic acids | SEQ ID NO: 42 | 5'-K-O-GG$^{(+)}$AG$^{(+)}$G-3'' | ++ |
|  | SEQ ID NO: 43 | 5'-GGA$^{(+)}$GGGCA$^{(+)}$GAA$^{(+)}$TCAT-O-K-3' | +++ |

Example 8-3: Analysis of Cell Viability in Human Breast Cancer Cells and Lung Cancer Cells To analyze the extent to which vascular endothelial growth factor is inhibited by the novel complex, the cells cultured in Example 8-1 were added to each well of a 96-well plate at a cell density of $6×10^3$ cells/well, treated with the complex, and then incubated for 24, 48, 72 and 96 hours, after which the cell viability after each incubation time was analyzed under the experimental conditions of Example 6-2.

Example 8-4: Analysis of Gene Expression by Western Blot Assay

To analyze the extent to which vascular endothelial growth factor is inhibited by the novel complex, the cells cultured in Example 7-1 were added to each well of a 6-well plate at a cell density of $1×10^5$ cells/well, treated with the complex, and then incubated for 24, 48, 72 and 96 hours. Next, under the experimental conditions of Example 4-3, protein expression was analyzed using anti-VEGF antibody (SantaCruz, USA) and anti-p-Akt1 (Cell signaling, USA).

Example 8-5: Analysis of Apoptosis by Flow Cytometry (FACS)

In order to analyze whether the novel complex induces apoptosis by inhibiting vascular endothelial growth factor, the cells cultured in Example 7-1 were added to each well of a 6-well plate at a cell density of $1×10^5$ cells/well and cultured for 72 hours. Then, the cells were harvested and dissolved in 500 μL of the annexin V binding buffer of the FITC annexin V apoptosis detection kit (BD, USA), and then treated with 5 μL of each of FITC annexin V and propidium iodide staining solution. Next, the cell solution was transferred into a flow cytometry tube, and then analyzed by FACS Canto II (BD, USA).

Example 8-6: Evaluation of Anticancer Efficacy Using Zebra Fishes

Using zebra fish eggs obtained by 2 days of incubation in an incubator, the human breast cancer cells (MDA-MB-231) cultured in Example 8-1 were stained green with CellTracem CFSE (Thermoscientific, USA) for 30 minutes and collected. Then, 150 stained human breast cancer cells per zebra fish were injected into zebra fish larvae by microinjection. The zebra fishes injected with the human breast cancer cells were dispensed in a 96-well place containing an aqueous solution of the complex, and then incubated in an incubator for 4 days. After 4 days of incubation, the zebra fishes were anesthetized with 0.04% tricaine, and then analyzed with a fluorescence microscope (OLYMPUS, Japan).

As a result, as shown in FIGS. 12a to 12c, it was confirmed that the novel complex inhibited cell viability by inhibiting the vascular endothelial growth factor in the human breast cancer cells and lung cancer cells and also inhibited protein expression of the vascular endothelial growth factor VEGF and its downstream gene p-Akt1. In addition, in order to examine whether apoptosis would be induced by inhibition of the vascular endothelial growth factor, flow cytometry was performed. As a result, it was confirmed that the complexes, comprising the bioactive peptide nucleic acid and each of the carrier peptide nucleic acids having different lengths and charge properties, showed apoptosis rates of 3.2% and 2%, respectively. Finally, zebra fishes used as animal models for evaluating anticancer efficacy were transplanted with the human breast cancer cells, and then analyzed. As a result, as shown in FIG. 13, it could be seen that the complex exhibited the effect of inhibiting the growth of the transplanted breast cancer cells.

Example 9: Examination of the Inhibition of Vascular Endothelial Growth Factor in Human Retinal Pigment Epithelium Cells by Novel Complex Using the novel complex against the vascular endothelial growth factor VEGF in macula known to cause age-related macular degeneration, human retinal pigment epithelium cells were treated with the complex, and whether the complex would inhibit vascular formation was examined.

Example 9-1: Cell Culture

Human Retinal Pigment Epithelium Cells (ARPE-19), obtained from the ATCC (American Type Culture Collection, USA), were cultured in DMEM medium (Dulbecco Modified Eagle Medium/Nutrient Mixture F-12, gibco, USA) containing 10% (v/v) fetal bovine serum, 100 units/ml penicillin and 100 μg/ml streptomycin at 37° C. under 5% (v/v) $CO_2$.

Example 9-2: Cell Culture and Intracellular Introduction of Complex Comprising Bioactive Peptide Nucleic Acid and Carrier Peptide Nucleic Acid A novel complex for inhibiting vascular endothelial growth factor was used in the same manner as in Example 7-2, and a method of treating cells with the novel complex was as described in Example 2.

Example 9-3: Analysis of Cell Viability in Human Retinal Pigment Epithelium Cells To analyze the extent to which vascular endothelial growth factor is inhibited by the novel complex, the cells cultured in Example 9-1 were added to each well of a 96-well plate at a cell density of $6 \times 10^3$ cells/well, treated with the complex, and then incubated for 24, 48, 72, 96 and 120 hours, after which the cell viability after each incubation time was analyzed under the experimental conditions of Example 6-2.

Example 9-4: Analysis of Gene Expression by Western Blot Assay

To analyze the extent to which vascular endothelial growth factor is inhibited by the novel complex, the cells cultured in Example 9-1 were added to each well of a 6-well plate at a cell density of $1 \times 10^5$ cells/well, treated with the complex, and then incubated for 24, 48, 72, 96 and 120 hours. Next, under the experimental conditions of Example 4-3, protein expression was analyzed using anti-VEGF antibody (SantaCruz, USA), anti-p-Akt1 (Cell signaling, USA), and anti-p-ERK-1 (Cell signaling, USA).

As a result, as shown in FIGS. 14a and 14b, it was confirmed that treatment with the novel complex inhibited cell viability in the human retinal pigment epithelium cells and also inhibited protein expression of VEGF and its downstream genes, p-Akt-1 and p-ERK-1.

Example 10: Examination of Anti-Inflammatory Pharmacological Effect of Novel Complex Against Psoriasis In order to verify the effect of the novel complex against the skin disease psoriasis, whether the novel complex would exhibit an anti-inflammatory effect by inhibiting the target gene IFI16 (interferon gamma inducible protein 16) was examined.

Example 10-1: Cell Culture

Human epidermal keratinocytes (HaCaT), obtained from the CLS (Cell Line Service, Germany), were cultured in DMEM medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$.

Example 10-2: Cell Culture and Intracellular Introduction of Complex Comprising Bioactive Peptide Nucleic Acid and Carrier Peptide Nucleic Acid To produce a novel complex for inhibiting IFI16, bioactive peptide nucleic acids (SEQ ID NOs: 44 to 47) complementary to IFI16 mRNA were constructed, and a carrier peptide nucleic acid (SEQ ID NO: 48) complementary to the bioactive peptide nucleic acid was constructed. Each of the bioactive peptide nucleic acids was hybridized with the same amount of the carrier peptide nucleic acid, thereby constructing complexes (see Table 4). A method of treating cells with the complex comprising the bioactive peptide nucleic acid bound to the carrier peptide nucleic acid was as described in Example 2 above.

TABLE 4

Sequences of bioactive nucleic acids for inhibition of IFI16 activity and carrier peptide nucleic acid

| Classification | SEQ ID NO | Nucleotide sequences | Monomer modification |
|---|---|---|---|
| Bioactive nucleic acids | SEQ ID NO: 44 | 5'-T$^{(-)}$GTA$^{(+)}$TTT$^{(-)}$CAA$^{(+)}$CC$^{(-)}$AGG-O-K-3' | -+-+- |
| | SEQ ID NO: 45 | 5'-AA$^{(-)}$TCG$^{(+)}$TTGC$^{(-)}$TCA$^{(+)}$GT$^{(-)}$A-O-K-O-K-3' | -+-+- |
| | SEQ ID NO: 46 | 5'-AT$^{(-)}$GGC$^{(+)}$TTT$^{(-)}$GTTG$^{(+)}$TA$^{(-)}$C-O-K-3' | -+-+- |
| | SEQ ID NO: 47 | 5'-AT$^{(-)}$TCA$^{(+)}$CAT$^{(-)}$CAG$^{(+)}$CC$^{(-)}$AC-O-K-3' | -+-+- |
| Carrier peptide nucleic acid | SEQ ID NO: 48 | 5'-CG$^{(+)}$GT$^{(+)}$G-O-K-3' | ++ |

Example 10-3: Analysis of Cell Viability in Human Epidermal Keratinocytes

To analyze the degree of inhibition of IFI16, the cells cultured in Example 10-1 were cultured in a 96-well plate at a density of 6×10$^3$ cells/well for 24 hours, and treated with the complex comprising the bioactive peptide nucleic acid and the carrier peptide nucleic acid. Then, to induce an inflammatory reaction, the human epidermal keratinocytes were treated with 20 ng/mL of IL-17A and incubated for 72, 96 and 120 hours. Next, cell viability was analyzed under the experimental conditions of Example 6-2.

Example 10-4: Analysis of Gene Expression by Western Blot Assay

To analyze the extent to which IFI16 is inhibited by the novel complex, the cells cultured in Example 10-1 were added to each well of a 6-well plate at a cell density of 1×10$^5$ cells/well, treated with the complex, and then incubated for 72, 96, 120 and 144 hours. Next, under the experimental conditions of Example 4-3, protein expression was analyzed using anti-IFI16 antibody (Cell Signaling, USA) and anti-p-NF-kB (Cell signaling, USA).

Example 10-5: Induction of Balb/C Mouse Psoriasis Models by Imiquimod and Analysis of the Change in Phenotype of Imiquimod Psoriasis Models by Complex Comprising Bioactive Nucleic Acid and Carrier Peptide Nucleic Acid 20 mg of imiquimod was applied daily to the right ear of 6-week-old Balb/C male mice for 12 days to induce psoriasis. To the psoriasis-induced mouse models, the novel complex in a liquid or cream form was applied at 2-day intervals for 12 days (a total of 6 times). The thickness of the right ear was measured by a micrometer, and the right ear thickness before initial psoriasis induction and the difference in ear thickness between the group treated with the novel complex and the control group were analyzed.

Example 10-6: Inhibition of Gene Expression by Novel Complex in Balb/C Mouse Models with Imiquimod-Induced Psoriasis The novel complex was applied under the same conditions as described in Example 10-5, and then the mouse right ear was biopsied. Total protein was extracted from the biopsy tissue and quantified by BCA (Bicinchoninic acid assay), and protein expression was analyzed according to the method of Example 10-4.

Example 10-7: Inhibition of Abnormal Growth of Tissue Keratinocytes by Complex Comprising Bioactive Peptide Nucleic Acid and Carrier Peptide Nucleic Acid in Balb/C Mouse Models with Imiquimod-Induced Psoriasis The novel complex was applied under the same conditions as described in Example 10-5, and then the mouse right ear was biopsied, fixed in 4% paraformaldehyde solution, and embedded in paraffin. The paraffin block was sectioned with a microtome and deparaffinized. The deparaffinized tissue was mounted on slide glass and stained with hematoxylin-eosin.

As a result, as shown in FIGS. 15a and 15b, it was confirmed that treatment of the human epidermal keratinocytes with the novel complex targeting the target gene IFI16 reduced the cell viability and also inhibited protein expression of the target gene IFI16 and its downstream gene p-NF-kB. In addition, an animal experiment was performed to confirm the anti-inflammatory effect of the novel complex against psoriasis. As a result, as shown in FIG. 16, the thickness of the mouse right ear was larger in the positive control group with imiquimod-induced psoriasis than in the negative control group without psoriasis, and the ear thickness in the group treated with the novel complex targeting IFI16 decreased to a level similar to that in the negative control group. In addition, the tissue biopsied in the animal experiment was used to examine whether expression of the target gene would be inhibited. As a result, it was confirmed that the expression of IFI16 in the group treated with the novel complex decreased, unlike the positive control group in which the expression of IFI16 increased. Finally, the mouse biopsy tissue was stained with H&E, and as a result, it was confirmed that the proliferation of epidermal keratinocytes in the positive control group increased compared to that in the negative control group, and the proliferation of epidermal keratinocytes in the group administered with the novel complex decreased.

Example 11: Examination of the Immune Anticancer Effect of Novel Complex in Human Breast Cancer Cells It is known that PD-L1 gene which is expressed on the surface of many kinds of cancer cells is not killed by immune cells by binding to PD-1 of T cells and continues to induce the proliferation of cancer cells. Thus, whether a novel complex targeting PD-L1 in human breast cancer cells showing high expression of PD-L1 would exhibit an immune anticancer effect by inhibiting PD-L1 was examined.

Example 11-1: Cell Culture

Cells were cultured in the same manner as described in Example 8-1.

Example 11-2: Cell Culture and Intracellular Introduction of Complex Comprising Bioactive Peptide Nucleic Acid and Carrier Peptide Nucleic Acid To produce a novel complex for inhibiting PD-L1, a bioactive peptide nucleic acid having a sequence (SEQ ID NO: 49) complementary to PD-L1 mRNA which is expressed on the surface of cancer cells was constructed, and a carrier peptide nucleic acid (SEQ ID NO: 50) complementary to the bioactive peptide nucleic acid was constructed. Then, the carrier peptide nucleic acid was hybridized with the same amount of the bioactive peptide nucleic acid, thereby constructing a complex (see Table 5). A method of treating cells with the novel complex comprising the bioactive peptide nucleic acid bound to the carrier peptide nucleic acid was as described in Example 2.

Example 11-3: Analysis of Gene Expression by Western Blot Assay

To analyze the extent to which PD-L1 is inhibited by the novel complex, the cells cultured in Example 11-1 were added to each well of a 6-well plate at a cell density of $1 \times 10^5$ cells/well, treated with the complex, and then incubated for 96, 120 and 144 hours. Next, under the experimental conditions of Example 4-3, protein expression was analyzed using anti-PD-L1 antibody (Abcam, England).

As a result, as shown in FIG. 17, it could be confirmed that treatment with the novel complex inhibited protein expression of the target gene PD-L1 in the human breast cancer cells compared to the negative control group.

Example 12: Inhibition of Bacterial Growth by Novel Complex

Whether a novel complex would inhibit bacterial growth by targeting acpP known as a gene essential for bacterial growth was examined.

Example 12-1: Bacterial Culture

*E. coli* DH5α (Enzynomics, Korea) was inoculated into Luria-Bertani (LB) broth, and then cultured to $10^5$ CFU at 30° C.

Example 12-2: Construction of Novel Complex for Inhibition of Bacterial Growth To construct a novel complex for inhibiting bacterial growth, a bioactive nucleic acid having a sequence (SEQ ID NO: 51) complementary to acpP mRNA, a gene essential for bacterial growth, was constructed, and a carrier peptide nucleic acid (SEQ ID NO: 52) complementary to the bioactive nucleic acid was constructed. Then, the carrier peptide nucleic acid was hybridized with the same amount of the bioactive nucleic acid, thereby constructing a complex (see Table 6)

TABLE 5

Sequences of bioactive nucleic acid for inhibition of PD-L1 activity and carrier peptide nucleic acid

| Classification | SEQ ID NO | Nucleotide sequences | Monomer modification |
|---|---|---|---|
| Bioactive nucleic acid | SEQ ID NO: 49 | 5'-AT$^{(-)}$GA$^{(+)}$AAGC$^{(-)}$AA$^{(+)}$TGA$^{(-)}$T-O-K-3'' | -+-+- |
| Carrier peptide nucleic acid | SEQ ID NO: 50 | 5'-K-O-AT$^{(+)}$CA$^{(+)}$T-3'' | ++ |

TABLE 6

Sequences of bioactive nucleic acid for
inhibition of acpP activity and carrier peptide nucleic acid

| Classification | SEQ ID NO | Nucleotide sequences | Monomer modification |
|---|---|---|---|
| Bioactive nucleic acid | SEQ ID NO: 51 | 5'-GCT$^{(-)}$CATACT$^{(+)}$CTTAAATT$^{(-)}$TCC-O-K-3' | -+- |
| Carrier peptide nucleic acid | SEQ ID NO: 52 | 5'-CGAGT$^{(+)}$ATGAGA$^{(+)}$ATTTA$^{(+)}$AAGG-O-K-3 | +++ |

Example 12-3: Analysis of Inhibition of Bacterial Growth by Complex

To analyze the degree to which bacterial growth is inhibited by the complex, the bacterial cells cultured in Example 12-1 were treated with 1 µM of the complex of Example 12-2 for 24 hours. Then, the culture was diluted serially, dropped onto solid media in the same amount, and then observed for 12, 24 and 48 hours. As a result, as shown in FIG. 18, it was confirmed that the growth of the test group treated with the complex was inhibited compared to the growth of the test group treated with the single-stranded bioactive nucleic acid alone.

INDUSTRIAL APPLICABILITY

The nucleic acid complex represented by structural formula (1) according to the present invention comprises a bioactive nucleic acid and a carrier peptide nucleic acid, and can increase the stability of the bioactive nucleic acid, reduce the loss (such as precipitation due to self-aggregation) of the bioactive nucleic acid, increase the intracellular delivery efficiency of the bioactive nucleic acid, and easily regulate expression of a target gene.

In particular, the binding between the bioactive nucleic acid and the carrier peptide nucleic acid in the nucleic acid complex according to the present invention is dissociated only in the presence of the nucleotide sequence of a target gene which is targeted by the bioactive nucleic acid. Thus, intracellular introduction of the nucleic acid complex shows higher selectivity and specificity for the target gene than intracellular introduction of the bioactive nucleic acid alone. In addition, according to the present invention, a complex having a controlled binding affinity between the bioactive nucleic acid and the carrier peptide nucleic acid can be prepared using various structural combinations of the bioactive nucleic acid and the carrier peptide nucleic acid, and thus there is an advantage in that it is possible to control the time of intracellular (or extracellular) action of the bioactive nucleic acid.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A nucleic acid complex having a structure represented by the following structural formula (1):

[A≡C(+)],                    [Structural formula (1)]

Wherein

A represents a bioactive nucleic acid having either a sequence capable of binding to a target gene or a target gene sequence;

C represents a carrier peptide nucleic acid capable of binding to the bioactive nucleic acid;

'≡' represents complementary binding between the bioactive nucleic acid and the carrier peptide nucleic acid;

the bioactive nucleic acid represented by A is PNA (Peptide Nucleic Acid), and has a generally negative charge;

C(+) indicates that the carrier peptide nucleic acid is generally positively charged; and the carrier peptide nucleic acid comprises one or more modified peptide nucleic acid monomers such that the carrier peptide nucleic acid is generally positively charged.

2. The nucleic acid complex of claim 1, wherein each of the bioactive nucleic acid and the carrier peptide nucleic acid comprises 2 to 50 nucleic acid monomers.

3. The nucleic acid complex of claim 1, wherein the nucleic acid complex is generally positively charged.

4. The nucleic acid complex of claim 1, wherein the carrier peptide nucleic acid has a nucleotide sequence which is partially or completely complementary to the bioactive nucleic acid, wherein the carrier peptide nucleic acid having a nucleotide sequence which is partially complementary to the bioactive nucleic acid comprises one or more universal bases.

5. The nucleic acid complex of claim 1, wherein the modified peptide carrier nucleic acid monomer is a gamma- or alpha-backbone modified peptide nucleic acid monomer, wherein the gamma- or alpha-backbone-modified peptide nucleic acid monomers comprise one or more positively charged amino acids selected from the group consisting of lysine (Lys, K), arginine (Arg, R), histidine (His, H), diamino butyric acid (DAB), ornithine (Orn), and an amino acid analoguein in the backbone to be electrically positive.

6. The nucleic acid complex of claim 1, wherein the modified peptide carrier nucleic acid monomer is a gamma- or alpha-backbone modified peptide nucleic acid monomer, wherein the gamma- or alpha-backbone-modified peptide nucleic acid monomers comprise one or more negatively charged amino acids selected from the group consisting of glutamic acid (Glu, E), aspartic acid (Asp, D), and an amino acid analogue in the backbone.

7. The nucleic acid complex of claim 1, wherein the modified peptide carrier nucleic acid monomer is a gamma- or alpha-backbone modified peptide nucleic acid monomer, wherein the gamma- or alpha-backbone-modified peptide nucleic acid monomers comprise a larger number of monomers having a positively charged amino acid than monomers having a negatively charged amino acid such that the carrier peptide nucleic acid is generally positively charged.

8. The nucleic acid complex of claim 1, wherein the binding between the bioactive nucleic acid and the carrier peptide nucleic acid is antiparallel binding according to 5'-directionality and 3'-directionality of each of the nucleic acids.

9. The nucleic acid complex of claim 1, wherein the binding affinity (melting temperature (Tm)) between the bioactive nucleic acid and the carrier peptide nucleic acid is lower than the binding affinity between the bioactive nucleic acid and a gene targeted by the bioactive nucleic acid.

10. The nucleic acid complex of claim 1, wherein the bioactive nucleic acid and the carrier peptide nucleic acid are bound to each other by parallel binding or partial specific binding so that the binding affinity (melting temperature (Tm)) between the bioactive nucleic acid and the carrier peptide nucleic acid is lower than the binding affinity between the bioactive nucleic acid and a gene targeted by the bioactive nucleic acid.

11. The nucleic acid complex of claim 1, wherein the carrier peptide nucleic acid has a linker, a universal base, and at least one peptide nucleobase selected from peptide nucleobases which are not complementary to the corresponding bases of the bioactive nucleic acid so that the binding affinity (melting temperature (Tm)) between the bioactive nucleic acid and the carrier peptide nucleic acid is lower than the binding affinity between the bioactive nucleic acid and a gene targeted by the bioactive nucleic acid.

12. The nucleic acid complex of claim 1, wherein the time of separation between the bioactive nucleic acid and the carrier peptide nucleic acid and the time of binding between the bioactive nucleic acid and the target gene of the bioactive nucleic acid is controlled by controlling the binding affinity between the bioactive nucleic acid and the carrier peptide nucleic acid.

13. The nucleic acid complex of claim 1, wherein the bioactive nucleic acid and/or the carrier peptide nucleic acid is/are bound to one or more substances selected from the group consisting of a hydrophobic moiety, a hydrophilic moiety, a target antigen-specific antibody, an aptamer, a quencher, a fluorescent marker, and a luminescent marker, wherein the bond is a single covalent bond or a linker-mediated covalent bond.

14. The nucleic acid complex of claim 1, wherein the particle size of the nucleic acid complex is 5 to 300 nm.

15. The nucleic acid complex of claim 14, wherein the particle size of the nucleic acid complex is controlled by controlling the charge balance of the nucleic acid complex.

16. A method for preventing or treating diseases, wherein the method comprises:

administering the nucleic acid complex of claim 1.

17. The method of claim 16, wherein the diseases are cancers, inflammatory diseases, age-related macular degeneration, rare diseases and severe diseases, cardiovascular diseases, metabolic diseases, or skin diseases.

18. The method of claim 16, wherein a target gene, to which the bioactive nucleic acid contained in the nucleic acid complex binds, is any one or more selected from the group consisting of Survivin, VEGF, Androgen receptor, KRAS, Clusterin, TGFβR2, ERBB3, Transglutaminase 2, ABCB1, Hsp27, STAT3, PD-L1, IFI16, TLR6, TIEG1, PDE4B, Pellino-1, SMN2, ApoB-100, ICAM-1, ApoCIII, TTR, HTT, GHr, SOD1, ANGPTL3, PKK, miR-21, TMPRSS6, FMR1, and Connexin 26.

19. The nucleic acid complex of claim 1, wherein the binding between the bioactive nucleic acid and the carrier peptide nucleic acid is parallel binding according to 5'-directionality and 3'-directionality of each of the nucleic acids.

\* \* \* \* \*

SEQUENCE LISTING

<160> NUMBER OF SEQ ID NOS: 49

<210> SEQ ID NO 1
<211> LENGTH: 17
<212> TYPE: DNA
<213> ORGANISM: Artificial Sequence
<220> FEATURE:
<223> OTHER INFORMATION: cp1

<400> SEQUENCE: 1
ctttcctaag acattgc                                                17

<210> SEQ ID NO 2
<211> LENGTH: 19
<212> TYPE: DNA
<213> ORGANISM: Artificial Sequence
<220> FEATURE:
<223> OTHER INFORMATION: cp2

<400> SEQUENCE: 2
tcctttccta agacattgc                                              19

<210> SEQ ID NO 3
<211> LENGTH: 17
<212> TYPE: DNA
<213> ORGANISM: Artificial Sequence

```
<220> FEATURE:
<223> OTHER INFORMATION: cp3

<400> SEQUENCE: 3
ctttcctaag acattgc                                                    17

<210> SEQ ID NO 4
<211> LENGTH: 15
<212> TYPE: DNA
<213> ORGANISM: Artificial Sequence
<220> FEATURE:
<223> OTHER INFORMATION: cp4

<400> SEQUENCE: 4
ctttcctaag acatt                                                      15

<210> SEQ ID NO 5
<211> LENGTH: 15
<212> TYPE: DNA
<213> ORGANISM: Artificial Sequence
<220> FEATURE:
<223> OTHER INFORMATION: cp5

<400> SEQUENCE: 5
ctttcctaag acatt                                                      15

<210> SEQ ID NO 6
<211> LENGTH: 17
<212> TYPE: DNA
<213> ORGANISM: Artificial Sequence
<220> FEATURE:
<223> OTHER INFORMATION: cp6

<400> SEQUENCE: 6
ctttcctaag acattgc                                                    17

<210> SEQ ID NO 7
<211> LENGTH: 17
<212> TYPE: DNA
<213> ORGANISM: Artificial Sequence
<220> FEATURE:
<223> OTHER INFORMATION: cp7

<400> SEQUENCE: 7
ttctcagtgg ggcagtg                                                    17

<210> SEQ ID NO 8
<211> LENGTH: 16
<212> TYPE: DNA
<213> ORGANISM: Artificial Sequence
<220> FEATURE:
<223> OTHER INFORMATION: cp8

<400> SEQUENCE: 8
tctcagtggg gcagtg                                                     16

<210> SEQ ID NO 9
<211> LENGTH: 15
<212> TYPE: DNA
<213> ORGANISM: Artificial Sequence
<220> FEATURE:
<223> OTHER INFORMATION: cp9

<400> SEQUENCE: 9
tctcagtggg gcagt                                                      15
```

```
<210> SEQ ID NO 10
<211> LENGTH: 14
<212> TYPE: DNA
<213> ORGANISM: Artificial Sequence
<220> FEATURE:
<223> OTHER INFORMATION: cp10

<400> SEQUENCE: 10
ctcagtgggg cagt                                                         14

<210> SEQ ID NO 11
<211> LENGTH: 13
<212> TYPE: DNA
<213> ORGANISM: Artificial Sequence
<220> FEATURE:
<223> OTHER INFORMATION: cp11

<400> SEQUENCE: 11
ctcagtgggg cag                                                          13

<210> SEQ ID NO 12
<211> LENGTH: 17
<212> TYPE: DNA
<213> ORGANISM: Artificial Sequence
<220> FEATURE:
<223> OTHER INFORMATION: cp12

<400> SEQUENCE: 12
ctttcctaag acattgc                                                      17

<210> SEQ ID NO 13
<211> LENGTH: 17
<212> TYPE: DNA
<213> ORGANISM: Artificial Sequence
<220> FEATURE:
<223> OTHER INFORMATION: cp13

<400> SEQUENCE: 13
ctttcctaag acattgc                                                      17

<210> SEQ ID NO 14
<211> LENGTH: 17
<212> TYPE: DNA
<213> ORGANISM: Artificial Sequence
<220> FEATURE:
<223> OTHER INFORMATION: cp14

<400> SEQUENCE: 14
ctttcctaag acattgc                                                      17

<210> SEQ ID NO 15
<211> LENGTH: 17
<212> TYPE: DNA
<213> ORGANISM: Artificial Sequence
<220> FEATURE:
<223> OTHER INFORMATION: cp15

<400> SEQUENCE: 15
ctttcctaag acattgc                                                      17

<210> SEQ ID NO 16
<211> LENGTH: 17
<212> TYPE: DNA
<213> ORGANISM: Artificial Sequence
<220> FEATURE:
<223> OTHER INFORMATION: cp16
```

-continued

<400> SEQUENCE: 16
ctttcctaag acattgc                                                    17

<210> SEQ ID NO 17
<211> LENGTH: 19
<212> TYPE: DNA
<213> ORGANISM: Artificial Sequence
<220> FEATURE:
<223> OTHER INFORMATION: cp17

<400> SEQUENCE: 17
tcctttccta agacattgc                                                  19

<210> SEQ ID NO 18
<211> LENGTH: 19
<212> TYPE: DNA
<213> ORGANISM: Artificial Sequence
<220> FEATURE:
<223> OTHER INFORMATION: cp18

<400> SEQUENCE: 18
tcctttccta agacattgc                                                  19

<210> SEQ ID NO 19
<211> LENGTH: 17
<212> TYPE: DNA
<213> ORGANISM: Artificial Sequence
<220> FEATURE:
<223> OTHER INFORMATION: cp19

<400> SEQUENCE: 19
gaaaggattc tgtaacg                                                    17

<210> SEQ ID NO 20
<211> LENGTH: 17
<212> TYPE: DNA
<213> ORGANISM: Artificial Sequence
<220> FEATURE:
<223> OTHER INFORMATION: cp20

<400> SEQUENCE: 20
gaaaggattc tgtaacg                                                    17

<210> SEQ ID NO 21
<211> LENGTH: 16
<212> TYPE: DNA
<213> ORGANISM: Artificial Sequence
<220> FEATURE:
<223> OTHER INFORMATION: cp21

<400> SEQUENCE: 21
gaaaggattt gtaacg                                                     16

<210> SEQ ID NO 22
<211> LENGTH: 15
<212> TYPE: DNA
<213> ORGANISM: Artificial Sequence
<220> FEATURE:
<223> OTHER INFORMATION: cp22

<400> SEQUENCE: 22
gaaagattcg taacg                                                      15

<210> SEQ ID NO 23

```
<211> LENGTH: 17
<212> TYPE: DNA
<213> ORGANISM: Artificial Sequence
<220> FEATURE:
<223> OTHER INFORMATION: cp23

<400> SEQUENCE: 23
gaaaggattc tgtaacg                                                    17

<210> SEQ ID NO 24
<211> LENGTH: 16
<212> TYPE: DNA
<213> ORGANISM: Artificial Sequence
<220> FEATURE:
<223> OTHER INFORMATION: cp24

<400> SEQUENCE: 24
gaaaggattt gtaacg                                                     16

<210> SEQ ID NO 25
<211> LENGTH: 15
<212> TYPE: DNA
<213> ORGANISM: Artificial Sequence
<220> FEATURE:
<223> OTHER INFORMATION: cp25

<400> SEQUENCE: 25
gaaagattcg taacg                                                      15

<210> SEQ ID NO 26
<211> LENGTH: 17
<212> TYPE: DNA
<213> ORGANISM: Artificial Sequence
<220> FEATURE:
<223> OTHER INFORMATION: cp26

<400> SEQUENCE: 26
gaaaggattc tgtaacg                                                    17

<210> SEQ ID NO 27
<211> LENGTH: 16
<212> TYPE: DNA
<213> ORGANISM: Artificial Sequence
<220> FEATURE:
<223> OTHER INFORMATION: cp27

<400> SEQUENCE: 27
gaaaggattt gtaacg                                                     16

<210> SEQ ID NO 28
<211> LENGTH: 15
<212> TYPE: DNA
<213> ORGANISM: Artificial Sequence
<220> FEATURE:
<223> OTHER INFORMATION: cp28

<400> SEQUENCE: 28
gaaagattcg taacg                                                      15

<210> SEQ ID NO 29
<211> LENGTH: 17
<212> TYPE: DNA
<213> ORGANISM: Artificial Sequence
<220> FEATURE:
<223> OTHER INFORMATION: cp29

<400> SEQUENCE: 29
```

```
gaaaggattc tgtaacg                                                    17

<210> SEQ ID NO 30
<211> LENGTH: 16
<212> TYPE: DNA
<213> ORGANISM: Artificial Sequence
<220> FEATURE:
<223> OTHER INFORMATION: cp30

<400> SEQUENCE: 30
gaaaggattt gtaacg                                                     16

<210> SEQ ID NO 31
<211> LENGTH: 15
<212> TYPE: DNA
<213> ORGANISM: Artificial Sequence
<220> FEATURE:
<223> OTHER INFORMATION: cp31

<400> SEQUENCE: 31
gaaagattcg taacg                                                      15

<210> SEQ ID NO 32
<211> LENGTH: 17
<212> TYPE: DNA
<213> ORGANISM: Artificial Sequence
<220> FEATURE:
<223> OTHER INFORMATION: cp32

<400> SEQUENCE: 32
gaaaggattc tgtaacg                                                    17

<210> SEQ ID NO 33
<211> LENGTH: 16
<212> TYPE: DNA
<213> ORGANISM: Artificial Sequence
<220> FEATURE:
<223> OTHER INFORMATION: cp33

<400> SEQUENCE: 33
agagtcaccc cgtcac                                                     16

<210> SEQ ID NO 34
<211> LENGTH: 15
<212> TYPE: DNA
<213> ORGANISM: Artificial Sequence
<220> FEATURE:
<223> OTHER INFORMATION: cp34

<400> SEQUENCE: 34
agagtcaccc cgtca                                                      15

<210> SEQ ID NO 35
<211> LENGTH: 14
<212> TYPE: DNA
<213> ORGANISM: Artificial Sequence
<220> FEATURE:
<223> OTHER INFORMATION: cp35

<400> SEQUENCE: 35
gagtcacccc gtca                                                       14

<210> SEQ ID NO 36
<211> LENGTH: 13
<212> TYPE: DNA
```

```
<213> ORGANISM: Artificial Sequence
<220> FEATURE:
<223> OTHER INFORMATION: cp36

<400> SEQUENCE: 36
gagtcacccc gtc                                                        13

<210> SEQ ID NO 37
<211> LENGTH: 17
<212> TYPE: DNA
<213> ORGANISM: Artificial Sequence
<220> FEATURE:
<223> OTHER INFORMATION: cp37

<400> SEQUENCE: 37
gaaaggattc tgtaacg                                                    17

<210> SEQ ID NO 38
<211> LENGTH: 17
<212> TYPE: DNA
<213> ORGANISM: Artificial Sequence
<220> FEATURE:
<223> OTHER INFORMATION: cp38

<400> SEQUENCE: 38
gaaaggattc tgtaacg                                                    17

<210> SEQ ID NO 39
<211> LENGTH: 17
<212> TYPE: DNA
<213> ORGANISM: Artificial Sequence
<220> FEATURE:
<223> OTHER INFORMATION: cp39

<400> SEQUENCE: 39
gaaaggattc tgtaacg                                                    17

<210> SEQ ID NO 40
<211> LENGTH: 17
<212> TYPE: DNA
<213> ORGANISM: Artificial Sequence
<220> FEATURE:
<223> OTHER INFORMATION: cp40

<400> SEQUENCE: 40
gaaaggattc tgtaacg                                                    17

<210> SEQ ID NO 41
<211> LENGTH: 15
<212> TYPE: DNA
<213> ORGANISM: Artificial Sequence
<220> FEATURE:
<223> OTHER INFORMATION: cp41

<400> SEQUENCE: 41
atgattctgc cctcc                                                      15

<210> SEQ ID NO 42
<211> LENGTH: 15
<212> TYPE: DNA
<213> ORGANISM: Artificial Sequence
<220> FEATURE:
<223> OTHER INFORMATION: cp43

<400> SEQUENCE: 42
ggagggcaga atcat                                                      15
```

<210> SEQ ID NO 43
<211> LENGTH: 15
<212> TYPE: DNA
<213> ORGANISM: Artificial Sequence
<220> FEATURE:
<223> OTHER INFORMATION: cp44

<400> SEQUENCE: 43
tgtatttcaa ccagg                                                    15

<210> SEQ ID NO 44
<211> LENGTH: 15
<212> TYPE: DNA
<213> ORGANISM: Artificial Sequence
<220> FEATURE:
<223> OTHER INFORMATION: cp45

<400> SEQUENCE: 44
aatcgttgct cagta                                                    15

<210> SEQ ID NO 45
<211> LENGTH: 15
<212> TYPE: DNA
<213> ORGANISM: Artificial Sequence
<220> FEATURE:
<223> OTHER INFORMATION: cp46

<400> SEQUENCE: 45
atggctttgt tgtac                                                    15

<210> SEQ ID NO 46
<211> LENGTH: 15
<212> TYPE: DNA
<213> ORGANISM: Artificial Sequence
<220> FEATURE:
<223> OTHER INFORMATION: cp47

<400> SEQUENCE: 46
attcacatca gccac                                                    15

<210> SEQ ID NO 47
<211> LENGTH: 14
<212> TYPE: DNA
<213> ORGANISM: Artificial Sequence
<220> FEATURE:
<223> OTHER INFORMATION: cp49

<400> SEQUENCE: 47
atgaaagcaa tgat                                                     14

<210> SEQ ID NO 48
<211> LENGTH: 20
<212> TYPE: DNA
<213> ORGANISM: Artificial Sequence
<220> FEATURE:
<223> OTHER INFORMATION: cp51

<400> SEQUENCE: 48
gctcatactc ttaaatttcc                                               20

<210> SEQ ID NO 49
<211> LENGTH: 20
<212> TYPE: DNA
<213> ORGANISM: Artificial Sequence
<220> FEATURE:

<223> OTHER INFORMATION: cp52

<400> SEQUENCE: 49
cgagtatgag aatttaaagg                                                  20